United States Patent
Hsieh et al.

(10) Patent No.: US 10,174,350 B2
(45) Date of Patent: Jan. 8, 2019

(54) GENETICALLY MODIFIED MICROORGANISM FOR PRODUCING MEDIUM-CHAIN LAURIC ACID AND/OR DODECANEDIOIC ACID AND METHOD OF USING THEREOF

(71) Applicant: INDUSTRIAL TECHNOLOGY RESEARCH INSTITUTE, Hsinchu (TW)

(72) Inventors: Hsin-Ju Hsieh, Hsinchu (TW); Yu-Ju Lin, Zhubei (TW); Hwei-Jiung Wang, Taipei (TW); Chwan-Deng Hsiao, Taipei (TW); Cheng-Chung Lee, Taichung (TW); Ya-Wen Chen, New Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 15/394,047

(22) Filed: Dec. 29, 2016

(65) Prior Publication Data

US 2017/0191092 A1    Jul. 6, 2017

Related U.S. Application Data

(63) Continuation-in-part of application No. 14/802,282, filed on Jul. 17, 2015, now Pat. No. 9,695,404.

(60) Provisional application No. 62/026,428, filed on Jul. 18, 2014, provisional application No. 62/032,956, filed on Aug. 4, 2014.

(30) Foreign Application Priority Data

Jun. 30, 2015 (TW) .............................. 104121064 A

(51) Int. Cl.
  *C12N 9/16* (2006.01)
  *C12P 7/44* (2006.01)
  *C12P 7/64* (2006.01)

(52) U.S. Cl.
  CPC .............. *C12P 7/6409* (2013.01); *C12N 9/16* (2013.01); *C12P 7/44* (2013.01); *C12P 7/6418* (2013.01); *C12Y 301/02014* (2013.01); *C12Y 301/02021* (2013.01)

(58) Field of Classification Search
  None
  See application file for complete search history.

(56) References Cited

U.S. PATENT DOCUMENTS

| | | |
|---|---|---|
| 6,004,784 A | 12/1999 | Mobley et al. |
| 6,066,480 A | 5/2000 | Mobley et al. |
| 8,143,034 B2 | 3/2012 | Gross et al. |
| 8,158,391 B2 | 4/2012 | Gross et al. |
| 8,383,373 B2 | 2/2013 | Kamal et al. |
| 2010/0041115 A1 | 2/2010 | Nicaud et al. |
| 2011/0165637 A1 | 7/2011 | Pfleger et al. |
| 2013/0197247 A1 | 8/2013 | Franklin et al. |
| 2013/0267012 A1 | 10/2013 | Steen et al. |

FOREIGN PATENT DOCUMENTS

| | | |
|---|---|---|
| CN | 1928100 A | 3/2007 |
| CN | 102115766 A | 7/2011 |
| EP | 0 341 796 A1 | 11/1989 |
| TW | 593264 B | 6/2004 |
| TW | 200801197 A | 1/2008 |
| TW | 201343912 A | 11/2013 |

OTHER PUBLICATIONS

Agnew et al., "Engineering *Escherichia coli* for production of $C_{12}$—$C_{14}$ polyhydroxyalkanoate from glucose," Metabolic Engineering, vol. 14, Issue 6, Nov. 2012, pp. 1-21.

Beller et al., "Genes Involved in Long-Chain Alkene Biosynthesis in Micrococcus luteus," Applied and Environmental Microbiology, Feb. 2010 (published ahead of print on Dec. 28, 2009), vol. 76, No. 4, pp. 1212-1223.

Green et al., "Candida cloacae oxidation of long-chain fatty acids to dioic acids," Elsevier, Enzyme and Microbial Technology, vol. 27, Issues 3-5, Aug. 2000, pp. 205-211.

Hsieh et al., "Lauroyl-Acyl Carrier Protein Thioesterase: a Key Enzyme for Regulation of Medium-Chain Fatty Acid Synthesis in *E. coli*," 2013 2nd International Conference on Environment, Energy and Biotechnology, Jun. 8-9, 2013, vol. 51, No. 29, pp. 153-156.

Jing et al., "Phylogenetic and experimental characterization of an acyl-ACP thioesterase family reveals significant diversity in enzymatic specificity and activity," BMC Biochemistry, Aug. 10, 2011, vol. 12, No. 44, pp. 1-16.

Kalscheuer et al., "Microdiesel: *Escherichia coli* engineered for fuel production," Microbiology, Sep. 2006, vol. 152, Pt. 9, pp. 2529-2536.

Lennen et al., "A process for microbial hydrocarbon synthesis: Overproduction of fatty acids in *Escherichia coli* and catalytic conversion to alkanes," Biotechnol Bioeng., Jun. 1, 2010, vol. 106, No, 2, pp. 1-19.

Lu et al., "Biosynthesis of Monomers for Plastics from Renewable Oils," J. Am. Chem. Soc., 2010 (published on Web Oct. 11, 2010), vol. 132, No. 43, pp. 15451-15455.

Mäki-Arvela et al., "Catalytic Deoxygenation of Fatty Acids and Their Derivatives," Energy & Fuels, 2007 (published on Web Dec. 15, 2006), vol. 21, No. 1, pp. 30-41.

(Continued)

*Primary Examiner* — Iqbal H Chowdhury
(74) *Attorney, Agent, or Firm* — Birch, Stewart, Kolasch & Birch, LLP

(57) ABSTRACT

Described herein are genetically-modified microorganisms for producing medium chain lauric acid and/or dodecanedioic acid and methods of using the microorganisms. The microorganisms contain a nucleic acid encoding an *Umbellularia californica* lauroyl ACP-thioesterase (BTE) operably linked to a promoter.

10 Claims, 29 Drawing Sheets

Specification includes a Sequence Listing.

(56) References Cited

OTHER PUBLICATIONS

Mendez-Perez et al., "Modular Synthase-Encoding Gene Involved in α-Olefin Biosynthesis in *Synechococcus* sp. Strain PCC 7002," Applied and Environmental Microbiology, Jun. 2011 (published ahead of print on Apr. 29, 2011), vol. 77, No. 12, pp. 4264-4267.
Rehm et al., "Heterologous expression of the acyl-acyl carrier protein thioesterase gene from the plant *Umbellularia californica* mediates polyhydroxyalkanoate biosynthesis in recombinant *Escherichia coli*," Appl Microbial Biotechnol, 2001 (published online Feb. 9, 2001), vol. 55, Issue 2, pp. 205-209.
Reiser et al., "isolation of mutants of Acinetobacter calcoaceticus deficient in wax ester synthesis and complementation of one mutation with a gene encoding a fatty acyl coenzyme A reductase," Journal of Bacteriology, May 1997, vol. 179, No. 9, pp. 2969-2975.
Rude et al., "Terminal Olefin (1-Alkene) Biosynthesis by a Novel P450 Fatty Acid Decarboxylase from *Jeotgalicoccus* Species," Applied and Environmental Microbiology, Mar. 2011 (published ahead of print on Jan. 7; 2011), vol. 77, No. 5, pp. 1718-1727.
Schirmer et al., "Microbial Biosynthesis of Alkanes," Science, Jul. 30, 2010, vol. 329, Issue 5991, pp. 559-562 (5 pages).
Smit et al., "Preparation of dodecanol-tolerant strains of Yarrowia lipolytica," Biotechnology Letters, May 2004, vol. 26, Issue 10, pp. 849-854.
Smit et al., "α,ω-Dicarboxylic acid accumulation by acyl-CoA oxidase deficient mutants of Yarrowia lipolytica," Biotechnology Letters, Jun. 2005, vol. 27, issue 12, pp. 859-864.
Steen et al., "Microbial production of fatty-acid-derived fuels and chemicals from plant biomass," Nature, vol. 463, Jan. 28, 2010, pp. 559-562 (5 pages).
Taiwanese Office Action and Search Report, dated Oct. 25, 2016, for Taiwanese Application No. 104121064.
U.S. Office Action, dated Nov. 2, 2016, for U.S. Appl. No. 14/802,282.
Voelker et al., "Alteration of the specificity and regulation of fatty acid synthesis of *Escherichia coli* by expression of a plant medium-chain acyl-acyl carrier protein thioesterase," Journal of Bacteriology, Dec. 1994, vol. 176, No. 23, pp. 7320-7327 (9 pages).
Zibek et al., "Fermentative Herstellung der α,ω-Di-carbonsäure 1,18-Oktadecendisäure als Grundbaustein für biobasierte Kunststoffe," Chemie Ingenieur Technik, 2009 (first published: Sep. 2, 2009), vol. 81, No. 11, pp. 1797-1808 (14 pages), with an English abstract.

Space group: $P2_12_12_1$
Resolution: 1.9 Å

Catalytic residues: N201, H203 and C238

| | BTE |
|---|---|
| Data collection | |
|   Wavelength (Å) | 1.0 |
|   Space group | $P2_1$ |
|   Cell dimensions (Å,°) | $a=83.1, b=73.7, c=118.3$ |
| | $\alpha=90.0, \beta=102.6, \gamma=90.0$ |
|   Resolution (Å) | 20.0-1.85 (1.92-1.85) |
|   Unique reflections | 375,520 |
|   $R_{merge}$ (%) | 5.3 (70.0) |
|   $I/\sigma(I)$ | 20.8 (1.6) |
|   Completeness | 99.2 (100.0) |
|   Redundancy | 3.1 (3.1) |
| Refinement | |
|   Resolution (Å) | 20.0-1.85 |
|   No. of reflections $R_{work}/R_{free}$ | 14,337/751 |
|   $R_{work}/R_{free}$ | 17.1/20.9 |
| No. of non-hydrogen atoms/Avg B factor (Å$^2$) | |
|   Protein | 8,335/26.4 |
|   Water | 971/38.7 |
| RMSD | |
|   Bond lengths (Å) | 0.02 |
|   Bond angles (°) | 2.05 |
| Ramachandran statistics (%)[b] | |
|   Most favored | 95.2 |
|   Additionally allowed | 4.8 |
|   Generously allowed | 0.0 |
|   Disallowed | 0.5 |

[a] Values corresponding to the highest resolution shells are shown in parentheses.

[b] Stereochemistry of the model was validated with PROCHECK.

FIG. 22B

GENETICALLY MODIFIED MICROORGANISM FOR PRODUCING MEDIUM-CHAIN LAURIC ACID AND/OR DODECANEDIOIC ACID AND METHOD OF USING THEREOF

CROSS REFERENCE TO RELATED APPLICATION

This application is a Continuation-In-Part of application Ser. No. 14/802,282, filed on Jul. 17, 2015, which claims the benefit of provisional Application No. 62/026,428, filed on Jul. 18, 2014, provisional Application No. 62/032,956, filed on Aug. 4, 2014, and Taiwan Application Serial Number 104121064, filed on Jun. 30, 2015, the entirety of which are incorporated by reference herein.

INCORPORATION BY REFERENCE OF SEQUENCE LISTING

This application is being filed electronically via EFS-Web and includes an electronically submitted sequence listing in .txt format. The .txt file contains a sequence listing entitled "2017-03-10 0941-3467PUS1 ST25.txt" created on Mar. 10, 2017 and is 204,901 bytes in size. The sequence listing contained in this .txt file is part of the specification and is hereby incorporated by reference herein in its entirety.

TECHNICAL FIELD

The technical field relates to genetically modified microorganism.

BACKGROUND

Long-carbon-chain nylon is a high-performing and high-value chemical material due to its unique thermal, physical, chemical and mechanical properties. Nylon 12 is a specialty resin designated for making fuel lines and brake systems. For high-grade Nylon 12, the price is usually more than 15 euros/kg. Analysis of a fatal explosion at a German plant of the world's largest Nylon 12 supplier, Evonik, revealed that explosion caused by contact between a highly active catalyst (Et2AlCl) and water is a major risk factor. Thus, there is a need for a safe process for producing long-chain dicarboxylic acids.

SUMMARY

In one aspect, described herein is a genetically modified microorganism that contains a first nucleic acid encoding an *Umbellularia californica* lauroyl ACP-thioesterase (BTE) operably linked to a promoter or a second nucleic acid encoding a *Cocos nucifera* lauroyl ACP-thioesterase (FatB3) operably linked to a promoter. The microorganism produces an increased amount of long-chain dicarboxylic acids as compared to the unmodified parent of the microorganism. The genetically modified microorganism can be *Yarrowia lipolytica* or *Escherichia coli*.

The genetically modified microorganism can include one or more further modifications. In one embodiment, it contains one or more additional nucleic acids each operably linked to a promoter, each additional nucleic acid encoding a protein selected from the group consisting of an acetyl-CoA carboxylase (ACC), an acetyl-CoA carboxylase carboxyl transferase subunit α (AccA), an acetyl-CoA carboxylase biotin carboxyl carrier protein (AccB), an acetyl-CoA biotin carboxylase (AccC), an acetyl-CoA carboxylase transferase subunit β (AccD), a fatty acid synthase (FAS) subunit, a cytochrome P450 reductase (CPR), a long-chain alcohol oxidase (FAO1), a long-chain alcohol dehydrogenase (FADH), and an adenosine monophosphate-forming acetylcoenzyme A synthetase (AceCS). Alternatively or additionally, the genetically modified microorganism can include a loss-of-function mutation in or expresses a lower level of one or more genes selected from the group consisting of a palmitoyl-acyl carrier protein (ACP) thioesterase gene, an acyl-coenzyme A oxidase gene, a citric synthetase (gltA) gene, or an acyl-coenzyme A synthetase (acs) gene.

In another aspect, described herein is a method of producing a long-chain dicarboxylic acid. The method includes culturing the genetically modified microorganism in a culture medium containing glucose or glycerol at pH 6 to 8 under conditions that allow production of a long-chain dicarboxylic acid, whereby the microorganism produces the long-chain dicarboxylic acid. The method can further include collecting the long-chain dicarboxylic acid, e.g., C10-C18 dicarboxylic acid.

In still another aspect, described herein is a genetically modified microorganism that contains a nucleic acid encoding an *Umbellularia californica* lauroyl ACP-thioesterase (BTE) operably linked to a promoter. The microorganism produces an increased amount of medium-chain lauric acid and/or dodecanedioic acid as compared to the unmodified parent of the microorganism.

The genetically modified microorganism can include one or more further modifications. In one embodiment, it contains one or more additional nucleic acids each operably linked to a promoter, each additional nucleic acid encoding a protein selected from the group consisting of an acetyl-CoA carboxylase (ACC), an acetyl-CoA carboxylase carboxyl transferase subunit α (AccA), an acetyl-CoA carboxylase biotin carboxyl carrier protein (AccB), an acetyl-CoA biotin carboxylase (AccC), an acetyl-CoA carboxylase transferase subunit β (AccD), a fatty acid synthase (FAS) subunit, a cytochrome P450 reductase (CPR), a long-chain alcohol oxidase (FAO1), a long-chain alcohol dehydrogenase (FADH), and an adenosine monophosphate-forming acetylcoenzyme A synthetase (AceCS). Alternatively or additionally, the genetically modified microorganism can include a loss-of-function mutation in or expresses a lower level of one or more genes selected from the group consisting of a palmitoyl-acyl carrier protein (ACP) thioesterase gene, an acyl-coenzyme A oxidase gene, a citric synthetase (gltA) gene, or an acyl-coenzyme A synthetase (acs) gene.

Also described herein is a method of producing a medium-chain lauric acid and/or dodecanedioic acid. The method includes culturing the genetically modified microorganism in a culture medium containing glucose or glycerol at pH 6 to 8 under conditions that allow production of the medium-chain lauric acid and/or dodecanedioic acid, whereby the microorganism produces the medium-chain lauric acid and/or dodecanedioic acid.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein:

FIGS. 22A and 22B show the three dimensional (3D) structure and structural analysis of the modified lauroyl ACP-thioesterase (BTE 02), respectively.

DETAILED DESCRIPTION

Figure 1:
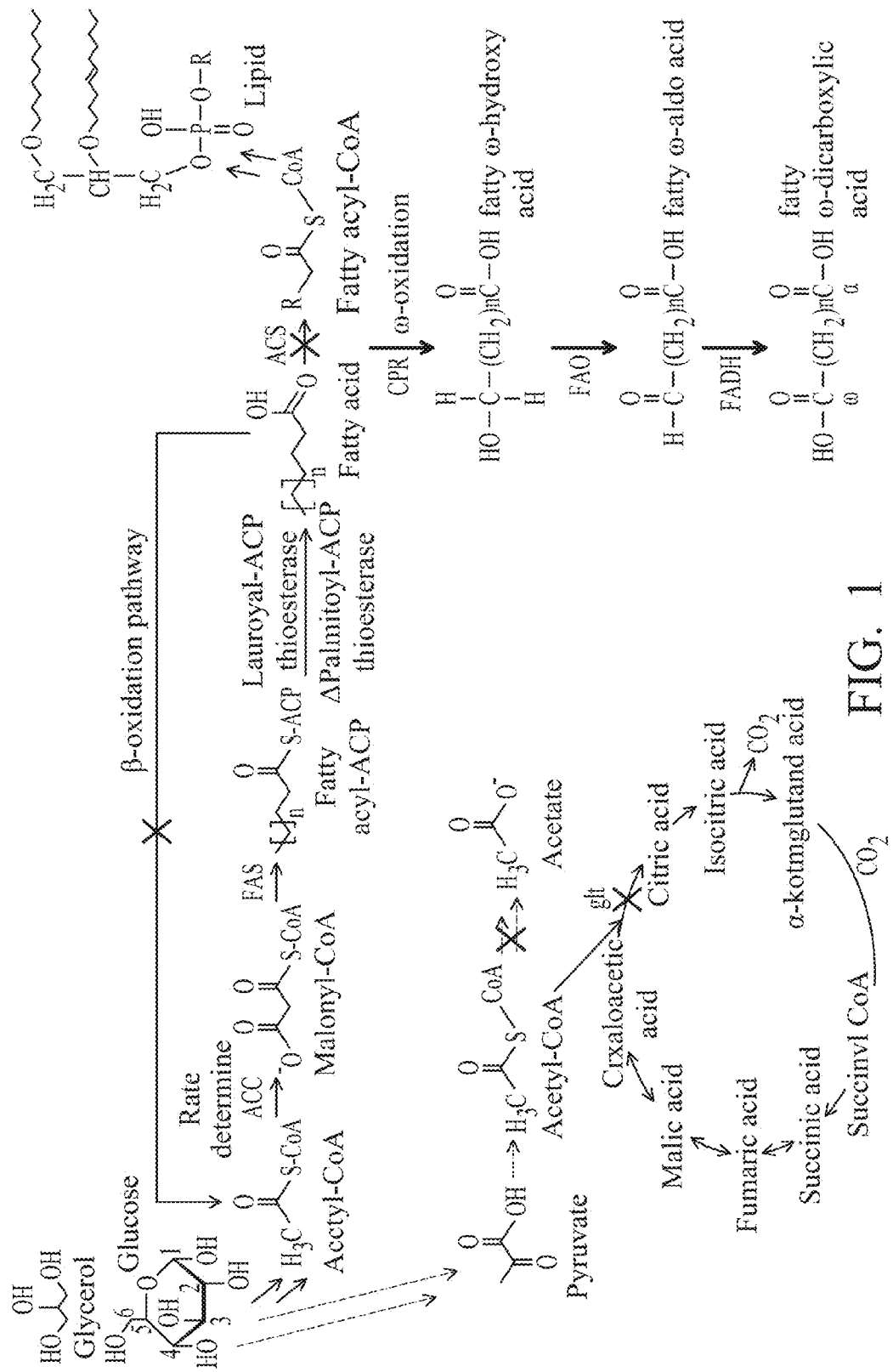
FIG. 1 is a schematic representation showing a modified α, ω-dicarboxylic acid metabolic pathway.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Described below are genetically-modified microorganisms for producing long-chain dicarboxylic acids and methods of using the microorganisms.

To improve production of dicarboxylic acids, one or more modifications can be introduced into the α, ω-dicarboxylic acid metabolic pathway of a microorganism. See FIG. 1. Such modifications can include, for example, increasing free fatty acid contents, enhancing substrate specificity of co-oxidation enzymes, increasing expression of key proteins in fatty acid synthesis (e.g., acetyl-CoA carboxylase and fatty acid synthase), knocking out a gene upstream of β-oxidation (e.g., acyl-CoA oxidase 2 (pox2), acyl-CoA oxidase 5 (pox5), or acyl-CoA synthetase (fadD)), decreasing fatty acid degradation, knocking out a citric synthetase gene (e.g., gltA), increasing fatty acid synthesis, knocking out an acyl-coenzyme A synthetase gene (e.g., acs), decreasing triglyceride accumulation, increasing expression of an adenosine monophosphate-forming acetyl-coenzyme A synthetase (AceCS), enhancing expression of a lauroyl-ACP thioesterases (e.g., *Cocos nucifera* FatB3 or *Umbellularia californica* BTE), decreasing or silencing expression of a palmitoyl-acyl carrier protein (ACP) thioesterase, and expressing co-oxidation metabolic pathway genes (e.g., cpr, fao1, and fadH).

Accordingly, a genetically-modified microorganism can contain a nucleic acid encoding an *Umbellularia californica* lauroyl ACP-thioesterase (BTE). It can alternatively or further include a nucleic acid encoding a *Cocos nucifera* lauroyl ACP-thioesterase (FatB3).

The genetically-modified microorganism can also have a nucleic acid that encodes an acetyl-CoA carboxylase (ACC), a fatty acid synthase (FAS) subunit, a cytochrome P450 reductase (CPR), a long-chain alcohol oxidase (e.g., FAO1), or a long-chain alcohol dehydrogenase (e.g., FADH).

Each of the above-described nucleic acid is operably linked to a suitable promoter for gene expression in the genetically-modified microorganism. If appropriate or necessary, the sequence of the nucleic acid can also be codon-optimized for expression in the genetically-modified microorganism.

Expression of one or more genes or proteins can also be decreased in the genetically-modified microorganism. For example, the expression of an ACP thioesterase gene, an acyl-coenzyme A oxidase gene (e.g., pox2, pox5, or fadD), a citric synthetase gene (gltA), or an acyl-coenzyme A synthetase gene (acs) can be decreased or silenced in the genetically-modified microorganism. Such a microorganism can have a loss-of-function mutation (e.g., deletion) in the gene or an expression construct that expresses an RNAi molecule targeting the gene.

As used herein, the term "promoter" refers to a nucleotide sequence containing elements that initiate the transcription of an operably linked nucleic acid sequence in a desired host cell. At a minimum, a promoter contains an RNA polymerase binding site. It can further contain one or more enhancer elements which, by definition, enhance transcription, or one or more regulatory elements that control the on/off status of the promoter. A promoter can be an inducible or constitutive promoter. Exemplary promoters include glyceraldehyde-3-phosphate dehydrogenase (GAP), fructose 1,6-bisphosphate aldolase intron (FBAin), beta-lactamase (bla, conferring ampicillin resistance), lac operon, T7, and SP6 promoters.

An expression cassette for expressing any of the genes described above can be introduced into a suitable host cell to produce a genetically modified microorganism using methods known in the art or described herein. Methods known in the art and described below can be used to knock-out a gene or decrease expression of a gene in a host cell to construct the genetically-modified microorganism.

Suitable host cells include, but are not limited to, *Candida tropicalis, Candida cloaceae, Escherichia coli*, and *Yarrowia lipolytica*.

The modified microorganism can then be cultured in a medium suitable for long chain dicarboxylic acid production. For example, the medium can contain glucose or glycerol as a carbon source. After a sufficient culturing period, dicarboxylic acids, in particular DCA12, can be isolated from the medium.

Moreover, also described herein is a genetically modified microorganism for producing medium-chain lauric acid and/or dodecanedioic acid and the method of using the microorganism.

Dodecanoic acid is also called lauric acid as a reactant in the ω-oxidation for producing dodecanedioic acid. There are two methods for industrial production of lauric acid: (1) saponifying or high-temperature and press-decomposing a natural vegetable oil; or (2) isolating lauric acid from synthesized fatty acid. In Japan, lauric acid is mainly extracted from coconut oil and palm kernel oil. The natural vegetable oils which can be used to extract lauric acid include coconut oil, *Litsea cubeba* kernel oil, and palm kernel oil. Other plants, such as palm kernel oil, sassafras seed oil, camphor seed oil, etc. also can be used to extract lauric acid. The C12 fraction left in the extraction process for lauric acid contains a large amount of dodecenoic acid which can be converted into lauric acid at a conversion rate of at least 86% at atmospheric pressure with the addition of hydrogen without a catalyst.

Figure 18:
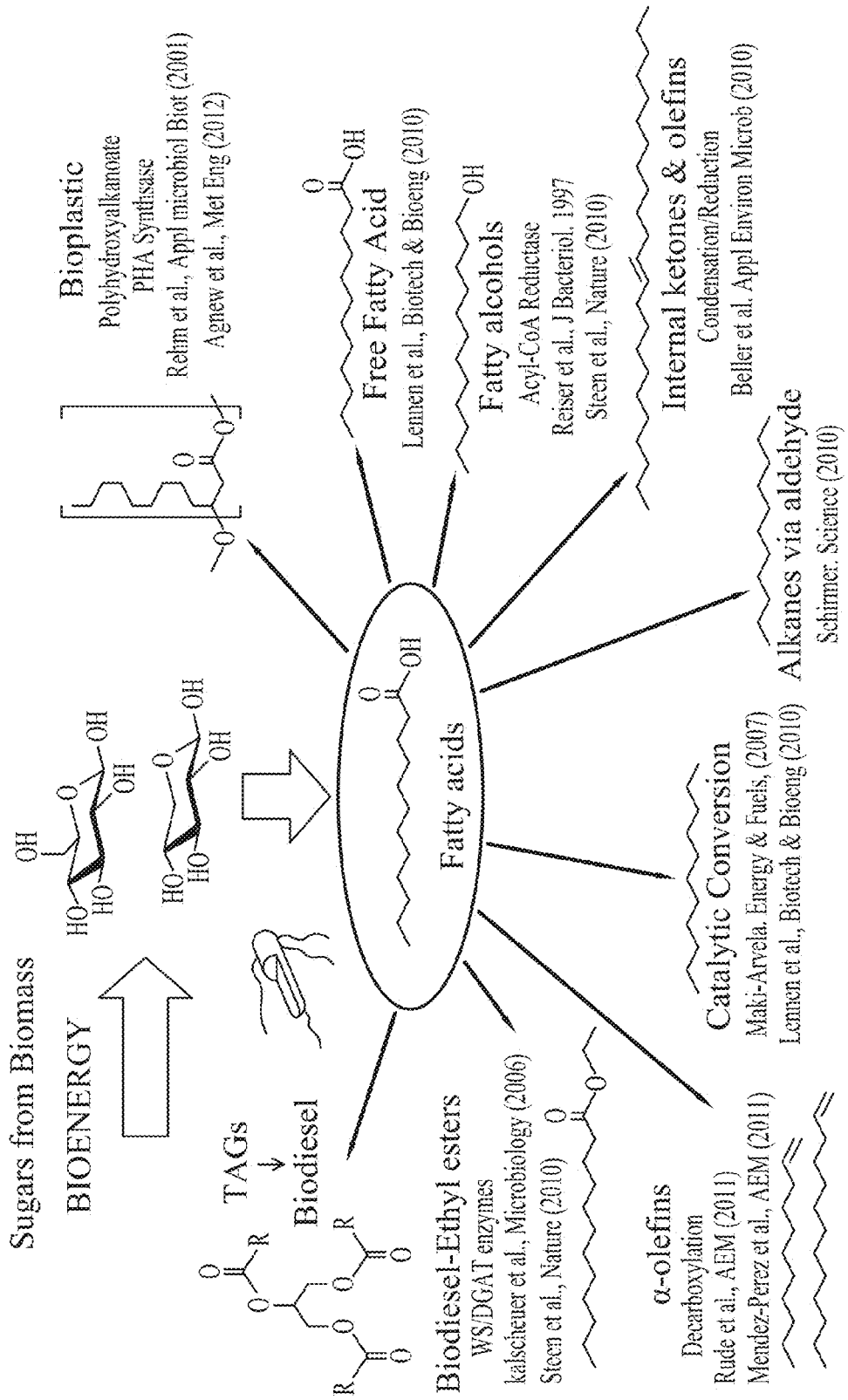
FIG. 18 is a schematic diagram showing application fields for lauric acid.

Application fields for lauric acid can refer to FIG. 18. Lauric acid is mainly used in the production of alkyd resins, wetting agents, detergents, pesticides, surfactants, food additives, and as raw materials for the perfume, pharmaceutical, and cosmetics industries. Lauric acid can also be applied toward the production of anti-corrosion additives for alkyd resins, chemical fiber oils, insecticides, synthetic perfumes, plastic stabilizers, petrol, and lubricants. Lauric acid is converted into glyceryl monolaurate when it is digested. Glyceryl monolaurate is an anti-virus and anti-bacterial compound which can used to resist lipid membrane bacteria in the human body. Lipid is a form of fat, and lauric acid in the form of glyceryl monolaurate can co-operate with lipids to destroy lipid membrane bacteria. A recent study by the University of Minnesota found that glyceryl monolaurate were effective in preventing immunodeficiency virus and AIDS virus (SIV) infection in female monkeys in an experiment using female monkeys as study subjects, as reported in the Journal "Nature".

Lauric acid can be used in the production of various types of surfactants such as cationic surfactants (such as laurylamine, lauronitrile, trilaurylamine, lauryldimethylamine, lauryltrimethylammonium salt, etc), anionic surfactants (such as sodium lauryl sulfate, lauryl sulfate, triethanolammonium lauryl sulfate, etc.), amphoteric surfactants (such as lauryl betaine, lauric acid imidazoline, etc.), and nonionic surfactants (such as poly-L-ol monolaurate, polyoxyethylene laurate, glyceryl laurate polyoxyethylene ether, lauric acid diethanolamide, etc.).

By using a biological manner, the amount of lauric acid produced in cells is increased in the present disclosure. In the present disclosure, the *Umbellularia californica* lauroyl ACP-thioesterase (BTE) encoded by the cell has been modified by protein engineering. Moreover, in the present disclosure a three dimensional (3D) structure of the lauroyl ACP-thioesterase (BTE) is analyzed. In addition, lauroyl ACP-thioesterase (BTE) with increased specificity and activity is also provided in the present disclosure.

The foregoing genetically modified microorganism can contain a nucleic acid encoding an *Umbellularia californica* lauroyl ACP-thioesterase (BTE) operably linked to a promoter. The microorganism produces an increased amount of medium-chain lauric acid and/or dodecanedioic acid as compared to the unmodified parent of the microorganism.

The *Umbellularia californica* lauroyl ACP-thioesterase (BTE) mentioned above can be a wild-type *Umbellularia californica* lauroyl ACP-thioesterase (BTE). Alternatively, the *Umbellularia californica* lauroyl ACP-thioesterase (BTE) mentioned above can be a modified *Umbellularia californica* lauroyl ACP-thioesterase (BTE).

The foregoing modified *Umbellularia californica* lauroyl ACP-thioesterase (BTE) may comprise residues 17-283 of a wild-type *Umbellularia californica* lauroyl ACP-thioesterase (BTE). It can further include a C-terminal His-tag fusion.

Alternatively, the foregoing modified *Umbellularia californica* lauroyl ACP-thioesterase (BTE) may comprise residues 17-295 of a wild-type *Umbellularia californica* lauroyl ACP-thioesterase (BTE). Also, it can further include a C-terminal His-tag fusion.

In one embodiment, the modified *Umbellularia californica* lauroyl ACP-thioesterase (BTE) may consist of residues 17-283 of a wild-type *Umbellularia californica* lauroyl ACP-thioesterase (BTE) and a C-terminal His-tag fusion. Furthermore, residue 124 of the wild-type *Umbellularia californica* lauroyl ACP-thioesterase (BTE), cysteine, can be further replaced with threonine.

In other embodiment, the modified *Umbellularia californica* lauroyl ACP-thioesterase (BTE) may consist of residues 17-295 of a wild-type *Umbellularia californica* lauroyl ACP-thioesterase (BTE) and a C-terminal His-tag fusion. Furthermore, residue 124 of the wild-type *Umbellularia californica* lauroyl ACP-thioesterase (BTE), cysteine, can be further replaced with threonine.

The genetically-modified microorganisms can also have a nucleic acid that encodes an acetyl-CoA carboxylase (ACC), an acetyl-CoA carboxylase carboxyl transferase subunit α (AccA), an acetyl-CoA carboxylase biotin carboxyl carrier protein (AccB), an acetyl-CoA biotin carboxylase (AccC), an acetyl-CoA carboxylase transferase subunit β (AccD), a fatty acid synthase (FAS) subunit, a cytochrome P450 reductase (CPR), a long-chain alcohol oxidase (e.g., FAO1), a long-chain alcohol dehydrogenase (e.g., FADH) or an adenosine monophosphate-forming acetyl-coenzyme A synthetase (AceCS).

Each of the above-described nucleic acid is operably linked to a suitable promoter for gene expression in the genetically-modified microorganism. If appropriate or necessary, the sequence of the nucleic acid can also be codon-optimized for expression in the genetically-modified microorganism.

Expression of one or more genes or proteins can also be decreased in the genetically-modified microorganism. For example, the expression of an ACP thioesterase gene, an acyl-coenzyme A oxidase gene (e.g., pox2, pox5, or fadD), a citric synthetase gene (gltA), or an acyl-coenzyme A synthetase gene (acs) can be decreased or silenced in the genetically-modified microorganism. Such a microorganism can have a loss-of-function mutation (e.g., deletion) in the gene or an expression construct that expresses an RNAi molecule targeting the gene.

In one embodiment, the genetically modified microorganism may (1) contain a loss-of-function mutation in or expresses a lower level of an acyl-coenzyme A oxidase gene and (2) contain additional nucleic acids each encoding a CPR, a FAO1, and a FADH, respectively.

In a specific embodiment, the genetically modified microorganism which contains a modified *Umbellularia californica* lauroyl ACP-thioesterase (BTE) comprising residues 17-283 of a wild-type *Umbellularia californica* lauroyl ACP-thioesterase (BTE) mentioned above may further (1) contain a loss-of-function mutation in or expresses a lower level of an acyl-coenzyme A oxidase gene and (2) contain additional nucleic acids each encoding a CPR, a FAO1, and a FADH, respectively. The acyl-coenzyme A oxidase gene may be fadD.

The term "promoter" used herein refers to a nucleotide sequence containing elements that initiate the transcription of an operably linked nucleic acid sequence in a desired host cell. At a minimum, a promoter contains an RNA polymerase binding site. It can further contain one or more enhancer elements which, by definition, enhance transcription, or one or more regulatory elements that control the on/off status of the promoter. A promoter can be an inducible or constitutive promoter. Exemplary promoters include glyceraldehyde-3-phosphate dehydrogenase (GAP), fructose 1,6-bisphosphate aldolase intron (FBAin), beta-lactamase (bla, conferring ampicillin resistance), lac operon, T7, and SP6 promoters.

An expression cassette for expressing any of the genes described above can be introduced into a suitable host cell to produce a genetically modified microorganism using methods known in the art or described herein. Methods known in the art and described below can be used to knock-out a gene or decrease expression of a gene in a host cell to construct the genetically-modified microorganism.

Suitable host cells include, but are not limited to, *Escherichia coli* and *Yarrowia lipolytica*.

The modified microorganism can then be cultured in a culture medium at pH 6 to 8 suitable for medium-chain lauric acid and/or dodecanedioic acid production. For example, the culture medium can contain glucose or glycerol as a carbon source. After a sufficient culturing period, medium-chain lauric acid and/or dodecanedioic acid can be isolated from the medium.

Exemplary nucleic acid and amino acid sequences of the proteins described herein are provided in the sequence listing: *Y. lipolytica* acetyl-CoA carboxylase (ACC) (SEQ ID NOs:1 and 2), *E. coli* acetyl-CoA carboxylase carboxyl transferase subunit α (AccA) (SEQ ID NOs: 3 and 4), *E. coli* acetyl-CoA carboxylase biotin carboxyl carrier protein (AccB/BCCP) (SEQ ID NOs:5 and 6), *E. coli* acetyl-CoA biotin carboxylase (AccC) (SEQ ID NOs:7 and 8), *E. coli* acetyl-CoA carboxylase transferase subunit β (AccD) (SEQ ID NOs:9 and 10), *Y. lipolytica* fatty acid synthase subunit α (FASA) (SEQ ID NOs:11 and 12), *Y. lipolytica* fatty acid synthase subunit β (FASB) (SEQ ID NOs:13 and 14), *Y. lipolytica* acetyl-CoA carboxylase transferase subunit β (AccD) (SEQ ID NOs:15 and 16), *Y. lipolytica* fatty acid synthase subunit alpha-active site 1 (FASA-1) (SEQ ID NOs:17 and 18), *Y. lipolytica* codon-optimized *Umbellularia californica* lauroyl ACP-thioesterase (BTE) (SEQ ID NOs: 19 and 20), *E. coli* codon-optimized BTEΔNC (SEQ ID NOs:21 and 22), *Y. lipolytica* codon-optimized *Cocos nucifera* lauroyl palmitoyl-acyl carrier protein (ACP) thioesterase (FatB3) (SEQ ID NOs:23 and 24), *E. coli* codon-optimized FatB3ΔNC (SEQ ID NOs:25 and 26), *Y. lipolytica* ACP thioesterase (SEQ ID NOs:27 and 28), *Candida tropicalis* cytochrome P450 reductase (CPR/CTP 00485) (SEQ ID NOs:29 and 30), *E. coli* codon-optimized *Candida tropicalis* CPR nucleic acid sequence (SEQ ID NO: 31), *Candida albicans* fatty alcohol oxgenase (FAO1) (SEQ ID NOs:32 and 33), *E. coli* codon-optimized *Candida albicans* FAO1 nucleic acid sequence (SEQ ID NO:34), *Candida albicans* fatty aldehyde hydrogenase (FADH) (SEQ ID Nos:35 and 36), *E. coli* codon-optimized *Candida albicans* FADH (SEQ ID NO:37), *Y. lipolytica* acyl-coenzyme A oxidase (POX2) (SEQ ID NOs:38 and 39), *Y. lipolytica* acyl-coenzyme A oxidase (POX5) (SEQ ID NOs:40 and 41), *E. coli* acyl-coenzyme A oxidase (FadD) (SEQ ID NOs:42 and 43), *E. coli* adenosine monophosphate-forming acetyl-CoA synthetase (AceCS) (SEQ ID NOs:44 and 45), *E. coli* acyl-CoA synthetase (ACS) (SEQ ID NOs:46 and 47), *E. coli* citric synthetase (gltA) (SEQ ID NOs:48 and 49), *E. coli* codon-optimized modified *Umbellularia californica* lauroyl ACP-thioesterase (BTE01) (SEQ ID NOs: 54 and 55), and *E. coli* codon-optimized modified *Umbellularia californica* lauroyl ACP-thioesterase (BTE02) (SEQ ID NOs:56 and 57).

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent.

Modified *Y. lipolytica* Strains

Figure 2:
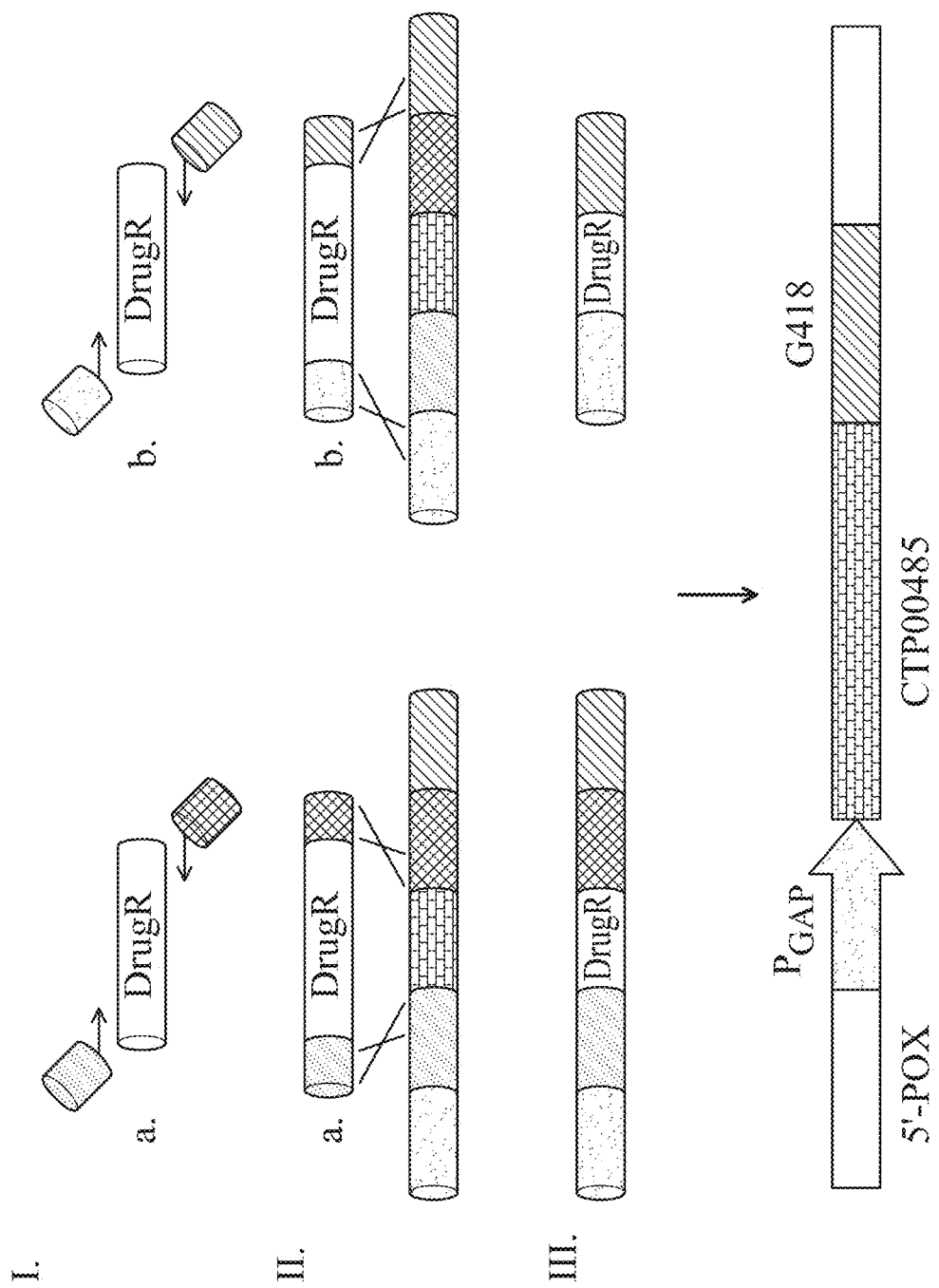
FIG. 2 is a schematic diagram showing construction of a modified *Y. lipolytica* strain.

Since *Yarrowia* and *Pichia* expression systems are similar, the *Yarrowia* expression system used in this study was design based on a *Pichia pastoris* expression system. A construct for single/double-crossover homologous recombination was designed to insert a co-oxidation gene into the acyl coenzyme A oxidase gene (pox1-5) of a *Yarrowia* strain in order to knock out the β-oxidation activity of the strain. Geneticin was used as the selectable marker. A schematic diagram of the construct is shown in FIG. 2.

Splice overlap extension (SOE) polymerase chain reaction (PCR) was used to generate a fusion construct containing pox2 or pox5 and a selectable marker (Kan::G418). See FIG. 2. The fusion construct was cloned into the pUC19 vector. The fusion construct was used to generate pox2- and pox5-deficient strains. Our analysis showed that this strategy significantly reduced unnecessary strain replication and DNA purification steps. The PCR product was used directly to efficiently transform a strain.

The electroporation method was used to introduce constructs into cells. First, *Y. lipolytica* cells were incubated in TE/LiAc/H$_2$O for 30 minutes, and then washed with Sorbitol to obtain competent *Y. lipolytica* cells. Constructs were then introduced into the cells via electroporation. 50-500 g/mL Geneticin was used to select for antibiotic-resistant transformants.

Activity of lauroyl-acyl carrier protein (ACP) thioesterase (BTE) was analyzed by the following procedure. Thioesterase activity was measured by following the increase in A$_{412}$, when free CoASH generated during deacylation of acyl-CoA reacted with DTNB. In short, each assay contained 100 mM Tris/HCl (pH 7.6), 0.4 mM DTNB and 100 μM acyl-CoA. The reaction was started by adding an aliquot of enzyme (1.5 μg) to a final volume of 0.5 mL. The contents were incubated at 37° C., and the change in absorbance was measured at 1 minute intervals for 5 minutes.

Three dimensional (3D) structure analysis of lauroyl-acyl carrier protein (ACP) thioesterase (BTE) was performed according to the following steps. Purified BTE was concentrated to 6-8 mg/ml in a buffer solution of 50 mM Tris-base, pH 7.6, 250 mM NaCl, 0.28 mM Lauryldimethylamine-N-oxide (LDAO) and crystallized at 18° C. by the sitting-drop vapor diffusion method. The BTE crystals were obtained in a reservoir solution of 5% 2-Methyl-2,4-pentanediol (MPD), 8% (w/v) PEG 3350, 0.1 M Tris-base, pH 8.5. X-ray experiments were performed at synchrotron beamline (National Synchrotron Radiation Research Center, NSRRC) BL15A. X-ray diffraction data were collected using the wavelength of 1.000 Å, recorded at cryogenic temperatures with cryoprotectant solution of 15% glycerol. The diffraction data were processed and scaled using the program HKL2000. BTE crystal structure was determined by molecular replacement using the program Phaser of the Phenix software package. The acyl-ACP thioesterase (PDB code: 4GAK) from bacteria *Spirosoma linguale* was used as the initial search model. BTE was crystallized in space group P2$_1$, with unit cells of a=83.1 Å, b=73.7 Å, c=118.3 Å, α=90°, β=102.6°, γ=90°, four molecules per asymmetric unit. Throughout the refinement, 5% of randomly selected data were set aside for cross validation with Rfree values. Manual modifications of the models were performed using the program Coot. Difference Fourier (Fo-Fc) maps were calculated to locate solvent molecules. All crystal structures were refined using Refmac5, including individual isotropic B-factor refinement. The molecular figures were produced using UCSF Chimera.

*Y. lipolytica* cells were cultured under various conditions in different media, i.e., YNB medium (0.17% YNB without amino acid, 0.5% ammonium sulphate, glucose or glycerol, 0.15% Yeast extract, 0.5% NH$_4$Cl, 0.01% Uracil, 2% Casamino acids, and 0.02% Tween-80) and NL medium (10% Glucose, 0.85% Yeast extract, and 0.3% Peptone). The cells and culturing media were collected for analysis using gas chromatography (GC) or high-performance liquid chromatography (HPLC).

For GC, a 5 mL culture sample was adjusted to pH 10.0 and then centrifuged. The supernatant was collected and the pH was adjusted to pH 2.0. The pellet was also collected. 14% BF3-Methanol (0.1 mL) and 0.2 mL Hexane was added to the sample and heated at 80-90° C. for 60 minutes. 0.2 mL of saline solution was added, and then 0.5 mL Hexane was added. GC analysis was then performed on the sample.

Figure 3:
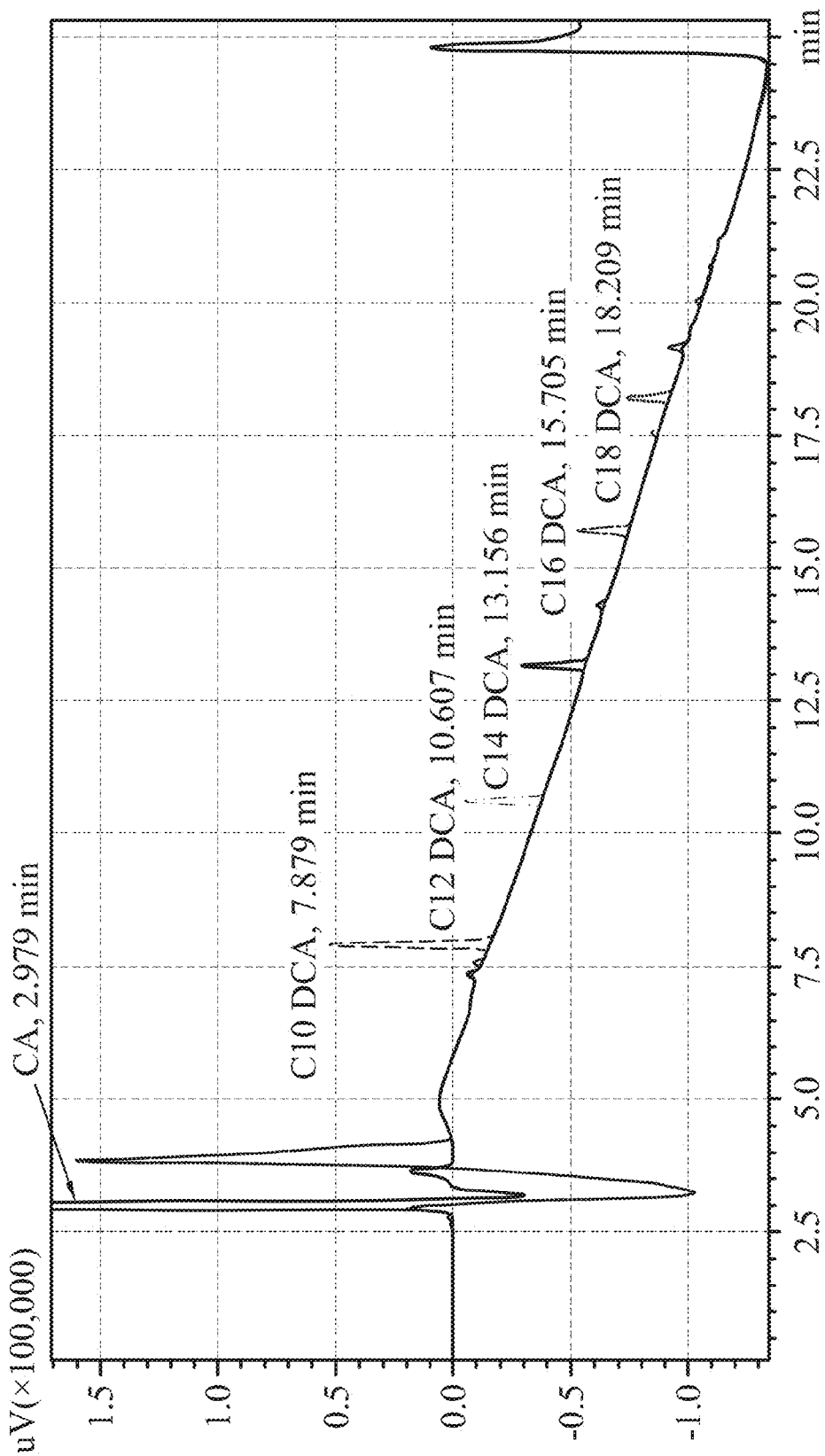
FIG. 3 is a graph showing HPLC analysis of dicarboxylic acid samples.

For HPLC, 5 mL of ethyl acetate was added to 5 mL of culture. The culture was then subjected to a Beatbeader sonicator for about one minute to break the cells and then centrifuged at 6000 rpm. The supernatant was collected. The solvent was allowed to evaporate from the supernatant. 1 mL of 99.5% ethanol was added to dissolve the extract. The sample was then analyzed by HPLC. See FIG. 3.

| Instrument: | Shimadzu 20ALC | | |
|---|---|---|---|
| Column: | Vercogel 120-5 C8, 5 μm, 4.6 × 250 mm (Vercopak no. 15835) | | |
| Eluent: | A: 0.1% TFA in H$_2$O | | |
| | B: AeCN | | |
| | Time | % A | % B |
| Gradient: | 0 | 70 | 30 |
| | 20 | 0 | 100 |
| | 22 | 70 | 30 |
| Flow rate: | 1.0 ml/min | | |
| Column oven: | 30° C. | | |
| Detection: | UV 220 nm | | |
| Samples: | Citric acid (CA), Sebacic acid (C10 DCA), Dodecanedioic acid (C12 DCA), Tetradecanedioic acid (C14 DCA), Hexadecanedioic acid (C16 DCA), Octanedecanedioic acid (C18 DCA) | | |
| Injection: | 10 μl | | |

Figure 4:
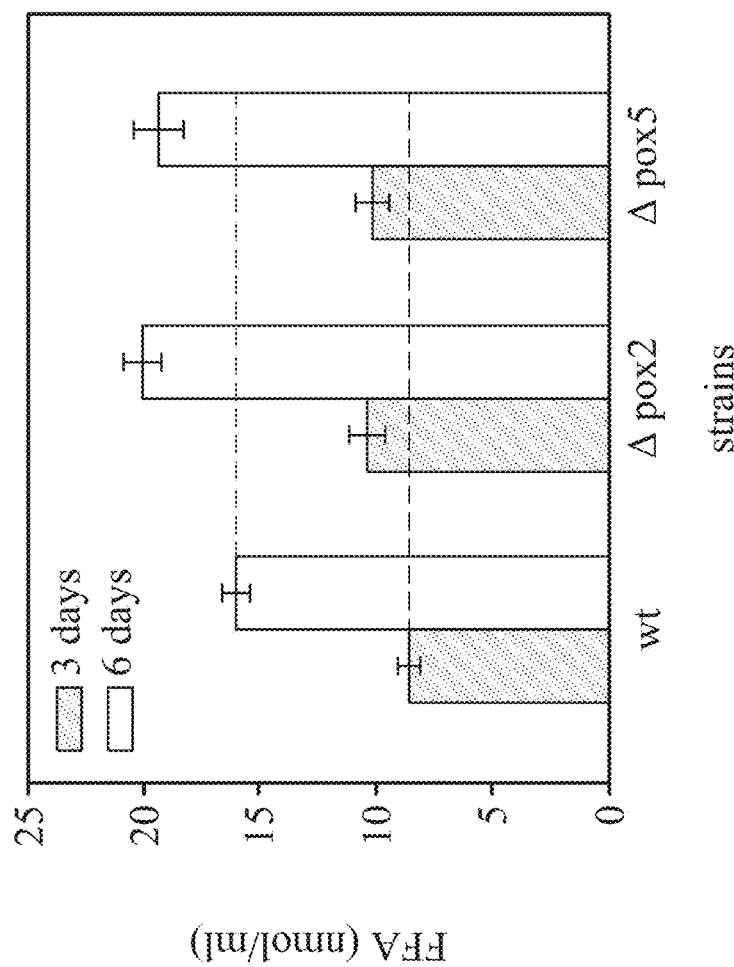
FIG. 4 is a graph showing the fatty acid contents of Δpox2 and Δpox5 mutants.

Our data showed that a pox2-deficient *Y. lipolytica* mutant accumulated more fatty acids than a pox5-deficient *Y. lipolytica* mutant. There was a 20% increase as compared to the wild-type. See FIG. 4.

Wild-type *Y. lipolytica* was cultured in YPD medium for one day, and then inoculated into 250 ml of YNB medium (10% glucose or glycerol) at an initial pH of 6.18 or 6.42. The cells were then cultured in a shaker bottle for 5 days without controlling the pH. Dicarboxylic acid production was measured. See Table 1.

TABLE 1

| Day | pH | | C10DCA (g/L) | C12DCA (g/L) | C14DCA (g/L) | C16DCA (g/L) |
|---|---|---|---|---|---|---|
| | | Residual glu (g/L) | | | | |
| D5 | 3.38 | 0 | 0.40 | — | 0.25 | — |
| | | Residual gly (g/L) | | | | |
| D5 | 3.19 | 0 | 0.47 | — | — | — |

Figure 5:
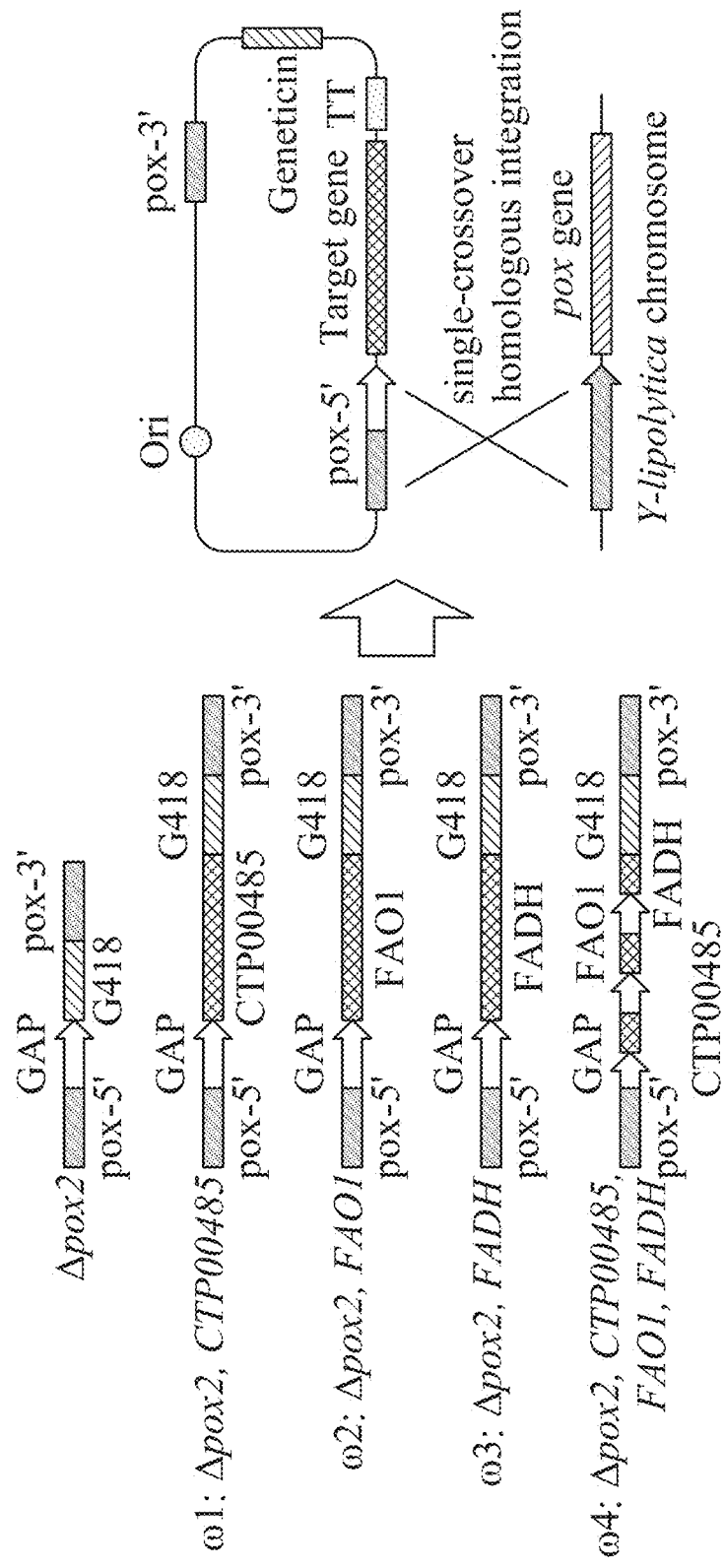
FIG. 5 is a schematic diagram showing construction of various modified *Y. lipolytica* strains.

Four *Y. lipolytica* strains (ω1, ω2, ω3, and ω4) were constructed using the targeted gene knockout method described above. See FIG. 5.

Strain ω04 was cultured in YPD medium for one day, inoculated into 500 ml of NL medium at an initial pH of 5.0, and then cultured in a fermenter without controlling the pH. Dicarboxylic acid production was measured. See Table 2.

TABLE 2

| Day | pH | | C10DCA (g/L) | C12DCA (g/L) | C14DCA (g/L) | C16DCA (g/L) |
|---|---|---|---|---|---|---|
| | | Residual glu (g/L) | | | | |
| D2 | 4.22 | 84.3 | 0.28 | 0.37 | 1.02 | — |
| D3 | 3.19 | 45.0 | 0.45 | 0.40 | 1.02 | — |
| D4 | 3.34 | 0 | 0.37 | 0.49 | 0.88 | — |
| D5 | 4.91 | 0 | 0.43 | 0.52 | 1.09 | — |

TABLE 2-continued

| Day | pH | C10DCA (g/L) | C12DCA (g/L) | C14DCA (g/L) | C16DCA (g/L) |
|---|---|---|---|---|---|
| | | Residual gly (g/L) | | | |
| D2 | 3.45 | 94 | 0.24 | 0.08 | 1.06 | — |
| D3 | 2.37 | 37 | 0.23 | 0.57 | 0.85 | — |

Figure 6:
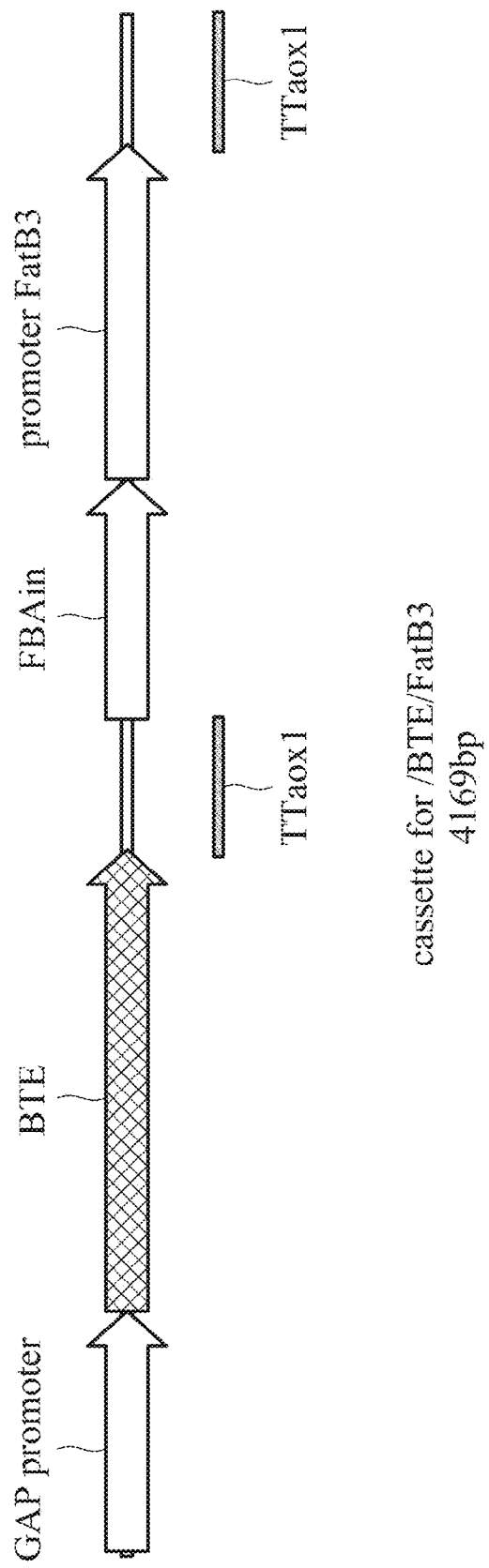
FIG. 6 is a schematic diagram showing an expression cassette for expressing an *Umbellularia californica* lauroyl ACP-thioesterase (BTE) and a *Cocos nucifera* lauroyl ACP-thioesterase (FatB3).

We constructed three additional *Y. lipolytica* strains, each expressing a lauroyl ACP-thioesterase (BTE, from *Umbellularia californica*), a lauroyl ACP-thioesterase (FatB3, from *Cocos nucifera*), or both. See FIG. 6.

TABLE 3

| | Relative fatty acid content (%) | | | | | | | | |
|---|---|---|---|---|---|---|---|---|---|
| Sample | C8:0 | C10:0 | C12:0 | C14:0 | 16:0 | 18:0 | 18:1 | 18:2 | 18:3 |
| Wild-type[1] | — | 7.1 | 6.3 | 5.9 | 19.2 | 28.6 | 23.1 | 5.6 | 2.1 |
| WT-B[1] | — | 7.1 | 6.8 | 7.5 | 19.5 | 26.9 | 22.3 | 5.8 | 2.5 |
| WT-F[1] | — | 6.9 | 7.1 | 7.8 | 18.5 | 27.1 | 21.8 | 6.4 | 2.4 |
| WT-B/F[1] | — | 7 | 13.5 | 6.8 | 16.5 | 23.7 | 19.5 | 5.4 | 3.2 |
| Wild-type[2] | — | 6.5 | 8.1 | 5.8 | 21.2 | 26.5 | 22.1 | 5.1 | 3.2 |
| WT-B[2] | — | 7.6 | 10.25 | 8.1 | 17.5 | 23.5 | 21.5 | 6.1 | 3.7 |
| WT-F[2] | — | 7.2 | 15.2 | 7.8 | 15.6 | 20.1 | 20.3 | 7.1 | 2.4 |
| WT-B/F[2] | — | 6.9 | 24.6 | 6.8 | 13.5 | 18.5 | 19.2 | 5.7 | 3.3 |
| Wild-type[3] | — | 6.6 | 10.2 | 5.9 | 20.5 | 25.6 | 21.1 | 4.9 | 3.9 |
| WT-B[3] | — | 6.3 | 16.5 | 8.9 | 16.2 | 20.5 | 21.5 | 5.6 | 3.7 |
| WT-F[3] | — | 7.5 | 21.5 | 7.5 | 13.4 | 17.6 | 20.7 | 6.7 | 3.2 |
| WT-B/F[3] | — | 7.1 | 29.5 | 5.9 | 10.2 | 15.9 | 20.3 | 7.1 | 3.3 |

WT-B: expresses BTE,
WT-F: expresses FatB3,
WT-B/F: expresses BTE and FatB3,
[1]NL medium;
[2]BMGY medium at day 3;
[3]BMGY medium at day 7

The strains were cultured in YPD medium for one day, inoculated into 250 ml of NL or BMGY medium (2% Peptone, 1% yeast extract, 100 mM potassium phosphate pH 6.0, 1.34% yeast nitrogen base (w/o amino acids), 0.4 µg/mL biotin, and 1% glycerol), and then cultured in a shaker bottle for 7 days. Free fatty acid production was then measured. See Table 3.

We also constructed strain ω5 (deposited at the Bioresource Collection and Research Center in Taiwan on Dec. 10, 2014 as BCRC 920096) by introducing the BTE and FatB3 genes into strain ω4. Strain ω5 was cultured in YNB medium at an initial pH of 6.18, and then cultured in a fermenter for 6 days without controlling the pH. Dicarboxylic acid production was then measured. See Table 4.

TABLE 4

| Day | pH | Residual glu (g/L) | C10DCA (g/L) | C12DCA (g/L) | C14DCA (g/L) | C16DCA (g/L) |
|---|---|---|---|---|---|---|
| D2 | 6.16 | 94.7 | 0.50 | — | 0.86 | — |
| D3 | 3.17 | 11.8 | 0.30 | — | 0.73 | — |
| D4 | 3.71 | 0 | 0.36 | 0.31 | 0.68 | — |
| D5 | 3.75 | 0 | 0.31 | 0.27 | 0.51 | — |
| D6 | 3.38 | 0 | 0.64 | 0.53 | 0.99 | — |

Figure 7:
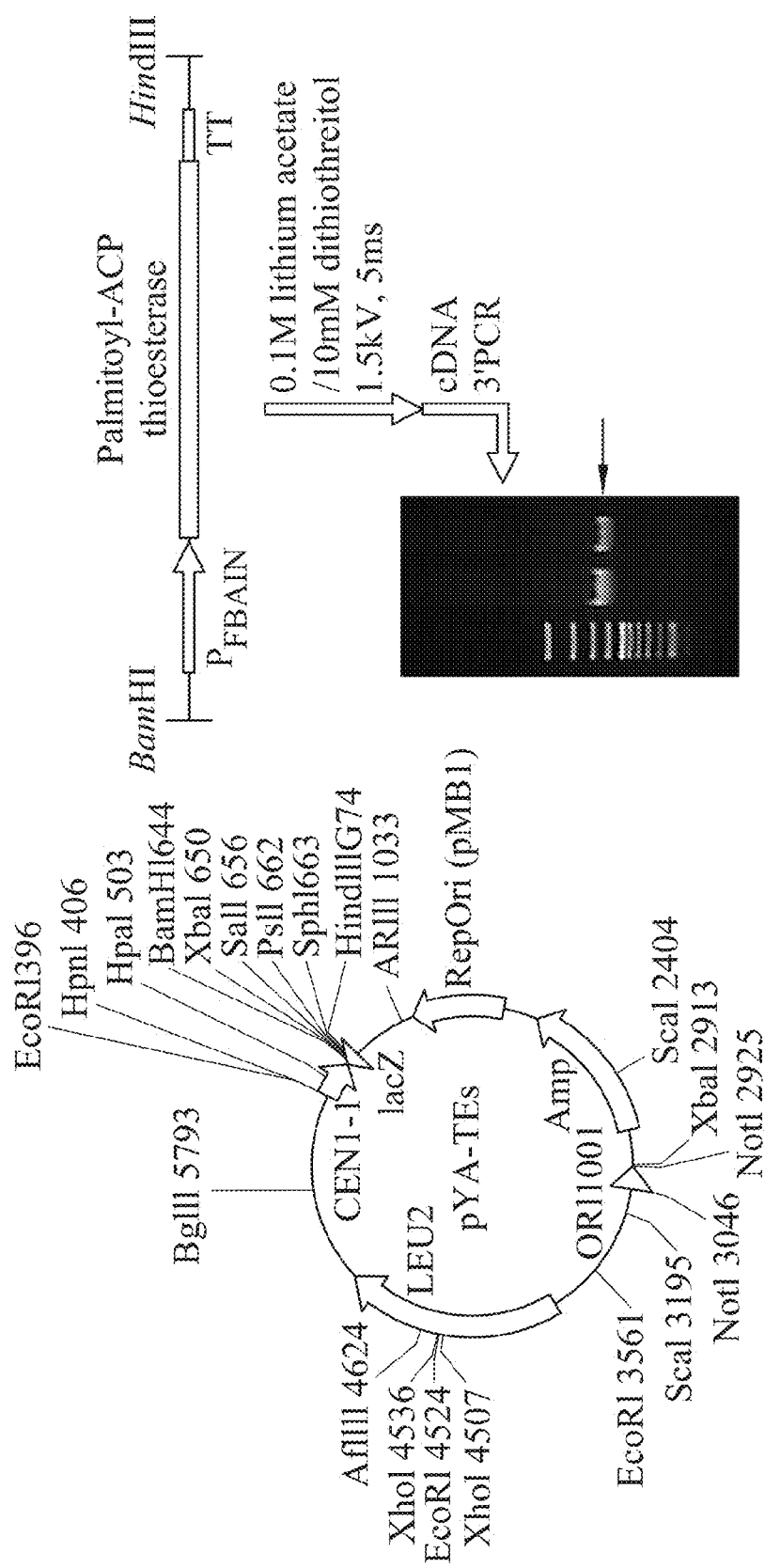
FIG. 7 is a schematic diagram showing construction of an RNAi expression cassette for silencing expression of the palmitoyl-acyl carrier protein (ACP) thioesterase gene.

In order to decrease DCA12 degradation, we constructed strain ω6 (ω5::Δ palmitoyl ACP-thioesterase; deposited at the Bioresource Collection and Research Center in Taiwan on Dec. 10, 2014 as BCRC 920097) using RNA interference. See FIG. 7.

TABLE 5

| Day | pH | Residual glu (g/L) | C10DCA (g/L) | C12DCA (g/L) | C14DCA (g/L) | C16DCA (g/L) |
|---|---|---|---|---|---|---|
| D2 | 4.24 | 58 | 1.90 | — | — | — |
| D3 | 3.35 | 0.2 | 0.50 | — | — | — |
| D4 | 2.85 | 0 | 0.52 | — | — | — |
| D5 | 3.85 | 0 | 0.71 | 0.58 | — | — |

Strain ω6 was cultured in YNB medium at an initial pH of 6.18, and then cultured in a shaker bottle for 5 days without controlling the pH. Dicarboxylic acid production was measured. See Table 5.

Figure 8:
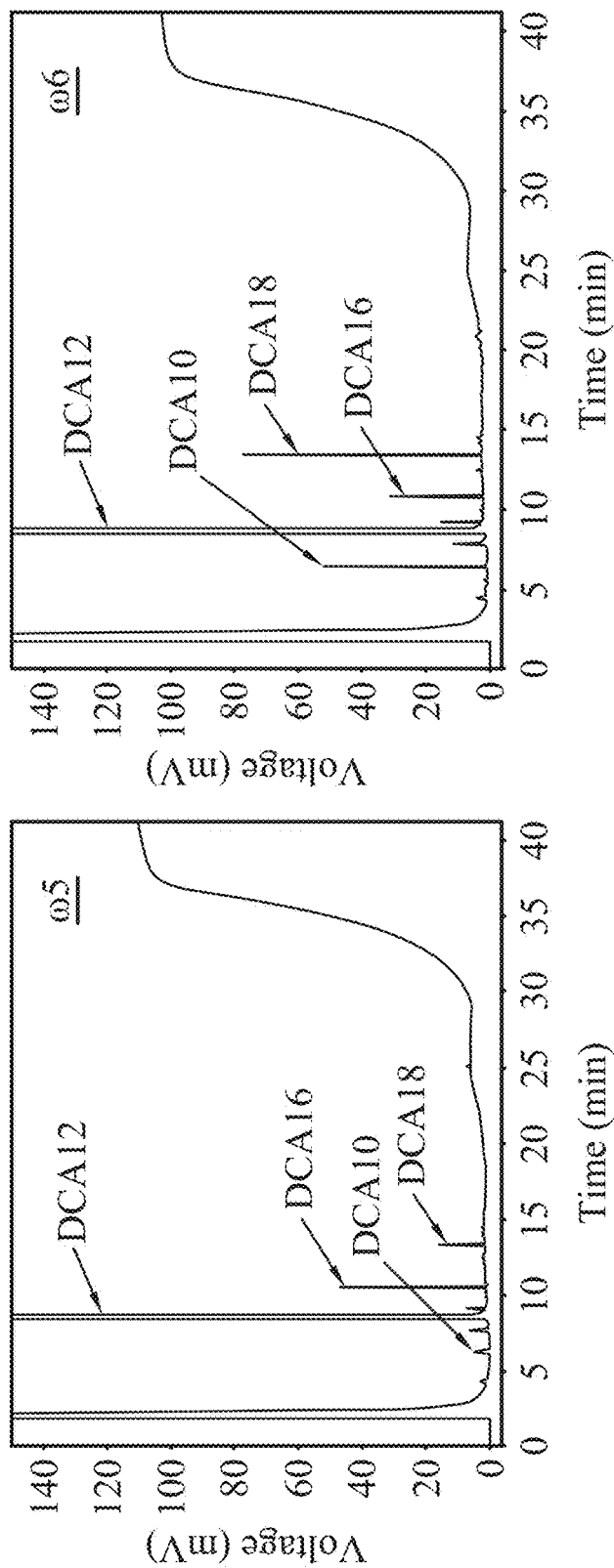
FIG. 8 is a set of graphs showing dicarboxylic acids produced by two modified *Y. lipolytica* strains.

Strains ω5 and ω6 were cultured in YPD medium for one day, and then inoculated into 250 ml of YNB medium (2% glucose) in a shaker bottle. The pH was maintained at 6.0 for two days. Additional 2% glucose was then added every 6 hours to maintain the pH at 7.5 for 5 days. For strain ω5, production of DCA12 increased from 12.9% to 51.2% (1.23 g/L) as compared to strain ω4. For strain ω6, DCA12 production was increased to 59.8% (2.35 g/L). See FIG. 8 and Table 6.

TABLE 6

| Strain | C10DCA | C12DCA | C14DCA | C16DCA |
|---|---|---|---|---|
| ω5 | 9.2 | 51.2 | 23.7 | 15.9 |
| ω6 | 11.1 | 59.8 | 10.9 | 18.2 |

We constructed strain ω7 (ω6::AccD::FASA-1; deposited at the Bioresource Collection and Research Center in Taiwan on Dec. 10, 2014 as BCRC 920098). Strain ω7 was cultured in YNB medium for 6 days without controlling the pH. Dicarboxylic acid production was measured. See Table 7.

TABLE 7

| Day | pH | Residual glu (g/L) | C10DCA (g/L) | C12DCA (g/L) | C14DCA (g/L) | C16DCA (g/L) |
|---|---|---|---|---|---|---|
| D2 | 4.24 | 93 | 1.69 | — | 0.29 | 0.27 |
| D3 | 3.35 | 21 | 0.15 | — | 0.41 | 0.73 |
| D4 | 2.85 | 0 | 0.49 | 0.46 | 0.62 | 0.48 |

TABLE 7-continued

| Day | pH | Residual glu (g/L) | C10DCA (g/L) | C12DCA (g/L) | C14DCA (g/L) | C16DCA (g/L) |
|---|---|---|---|---|---|---|
| D5 | 3.85 | 0 | 0.53 | 0.47 | 0.62 | 0.48 |
| D6 | 5.47 | 0 | 0.52 | 0.58 | 0.62 | 0.46 |

Strain ω7 was cultured in YNB medium in a fermentor under 1 vvm aeration and at 300 rpm. The pH was maintained at 6.0 for the first two days, and then every 6 hours, additional 2% glucose was added to maintain the pH at 6.0 for additional 5 days.

Dicarboxylic acid production was measured. See Table 8.

TABLE 8

| Day | C10DCA (g/L) | C12DCA (g/L) | C14DCA (g/L) | C16DCA (g/L) | C18DCA (g/L) |
|---|---|---|---|---|---|
| D0 | 0.24 | 0.21 | 0.15 | 0.17 | 0.10 |
| D1 | 0.45 | 0.38 | 0.18 | 0.26 | 0.18 |
| D2 | 0.77 | 0.45 | 0.27 | 0.35 | 0.16 |
| D3 | 0.53 | 0.72 | 0.32 | 0.39 | 0.17 |
| D4 | 0.48 | 1.11 | 0.41 | 0.43 | 0.15 |
| D5 | 0.32 | 1.19 | 0.49 | 0.45 | 0.21 |

Strain ω7 was cultured in YNB medium in a fermentor under 1 vvm aeration and at 300 rpm. The pH was maintained at 6.0 for the first two days, and then every 6 hours, additional 2% glucose was added to maintain the pH at 7.5 for additional 5 days. Dicarboxylic acid production was measured. See Table 9.

TABLE 9

| Day | C10DCA (g/L) | C12DCA (g/L) | C14DCA (g/L) | C16DCA (g/L) | C18DCA (g/L) |
|---|---|---|---|---|---|
| D0 | 0.27 | 0.26 | 0.12 | 0.18 | 0.14 |
| D1 | 0.30 | 0.49 | 0.23 | 0.15 | 0.12 |
| D2 | 0.76 | 1.01 | 0.53 | 0.14 | 0.22 |
| D3 | 0.84 | 1.51 | 0.74 | 0.21 | 0.32 |
| D4 | 0.67 | 2.23 | 1.26 | 0.27 | 0.34 |
| D5 | 0.60 | 2.78 | 1.47 | 0.43 | 0.41 |

Modified E. coli Strains

Modified E. coli strains were constructed using expression vectors to express certain proteins. To eliminate the β-oxidation activity of the strains, the fadD gene was deleted. The ΔfadD strain was used as the host strain to construct strains E1, E2, E3, E4, E5, and E6.

Figure 9:
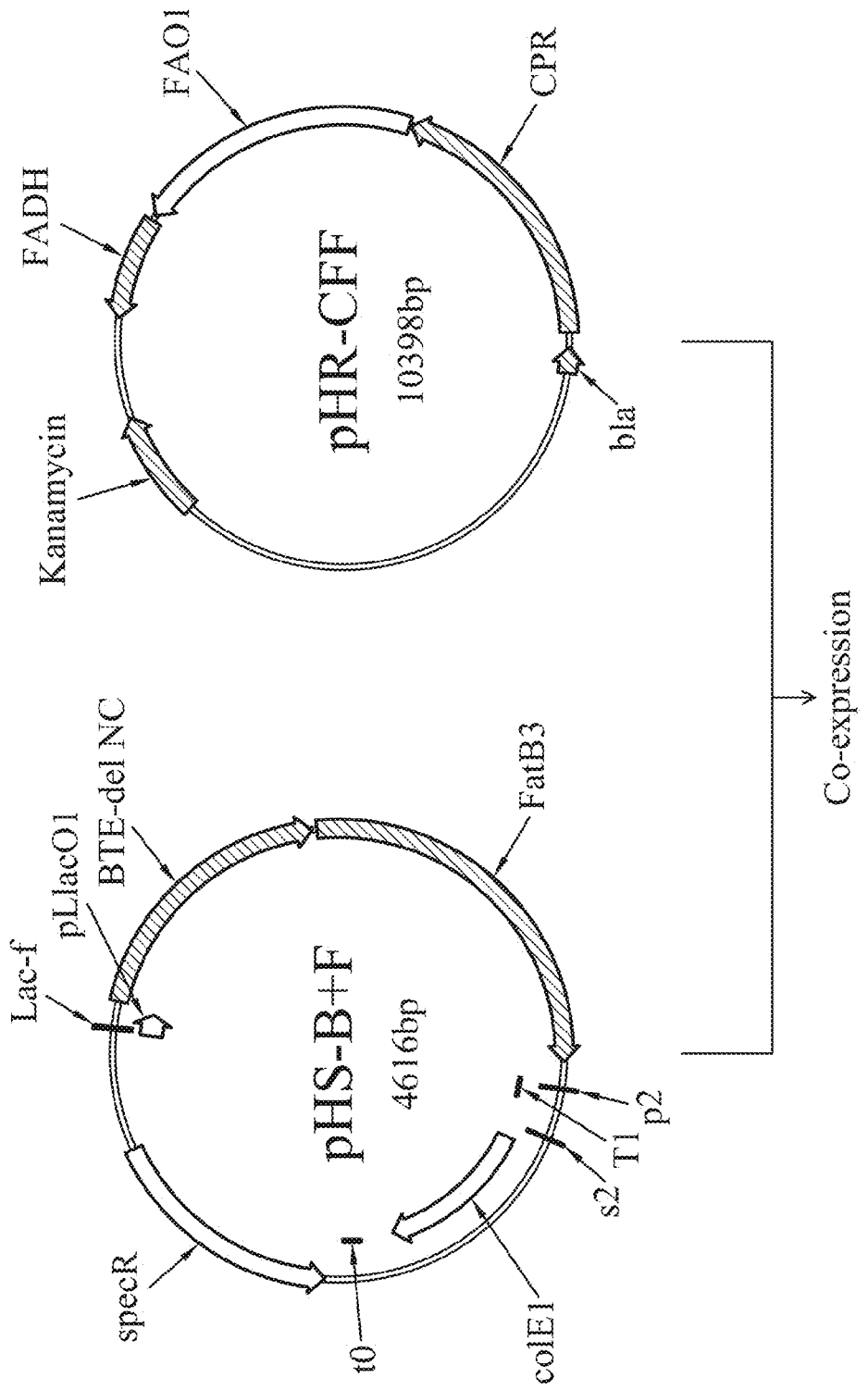
FIG. 9 is a schematic diagram showing expression constructs for generating modified *E. coli* strain E1.

We constructed strain EI (ΔfadD::BTEΔNC::FatB3::CPR::FAO::FADH). The BTEΔNC and FatB3 genes were inserted into the Acc65I/SalI and HindIII/BamHI sites in the pHS vector, respectively. The CPR, FAO, and FADH CPR, FAO, and FADH genes were inserted into the BamHI/EcoRI, SalI/HindIII, and XhoI sites in the pHR vector, respectively. The resulting expression constructs (pHS-B+F and pHR-CFF) were introduced into host E. coli cells to generate strain E1. See FIG. 9.

Figure 10:
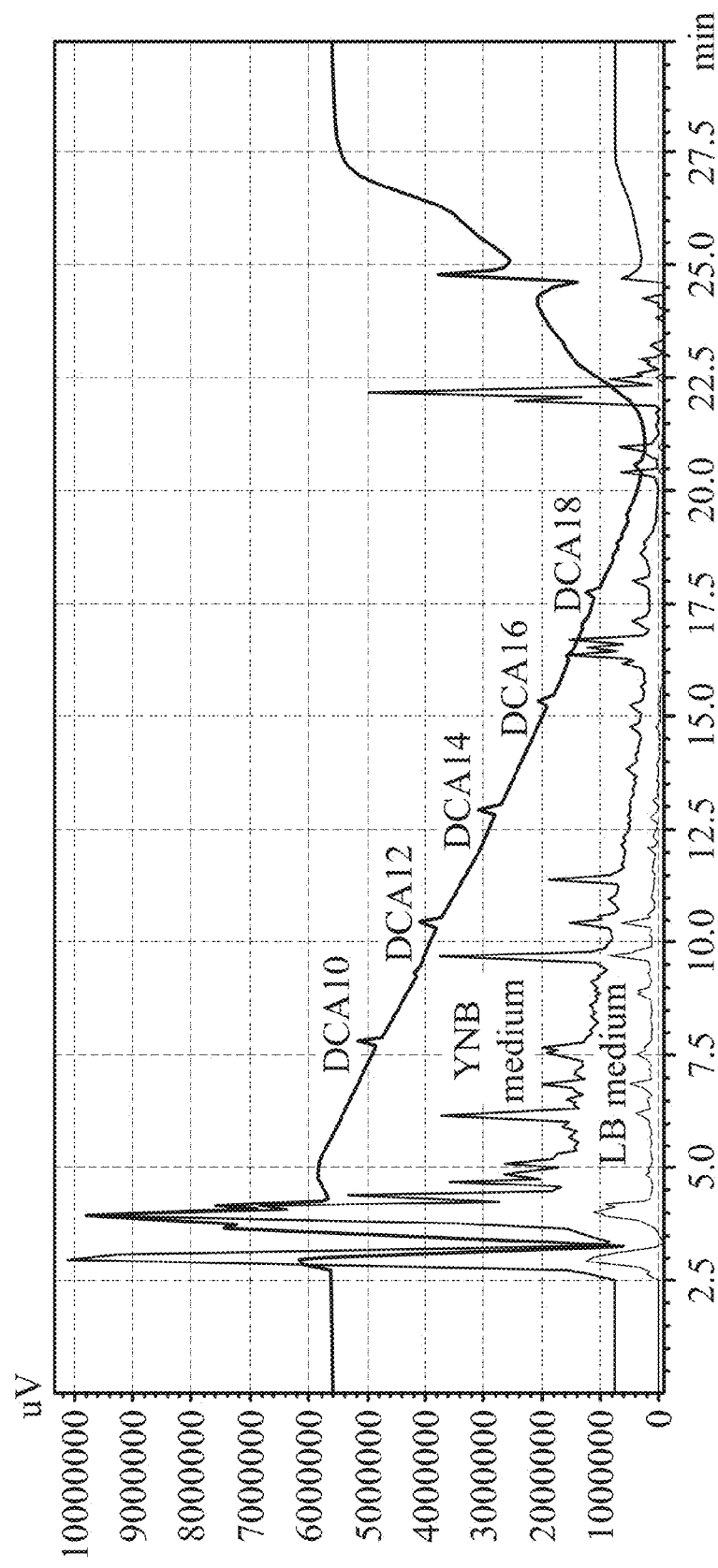
FIG. 10 is a graph showing HLPC analysis of dicarboxylic acid production of strain E1.

Strain E1 was cultured in YNB or LB medium in a fermentor under 1 vvm aeration and at 300 rpm. The pH was maintained at 6.0 for 1 day. Every 6 hours thereafter, additional 1% glucose was added to maintain the pH at 7.5 for two days. Dicarboxylic acid production was measured. See FIG. 10. As shown in FIG. 10, production reached 0.2 g.

Figure 11:
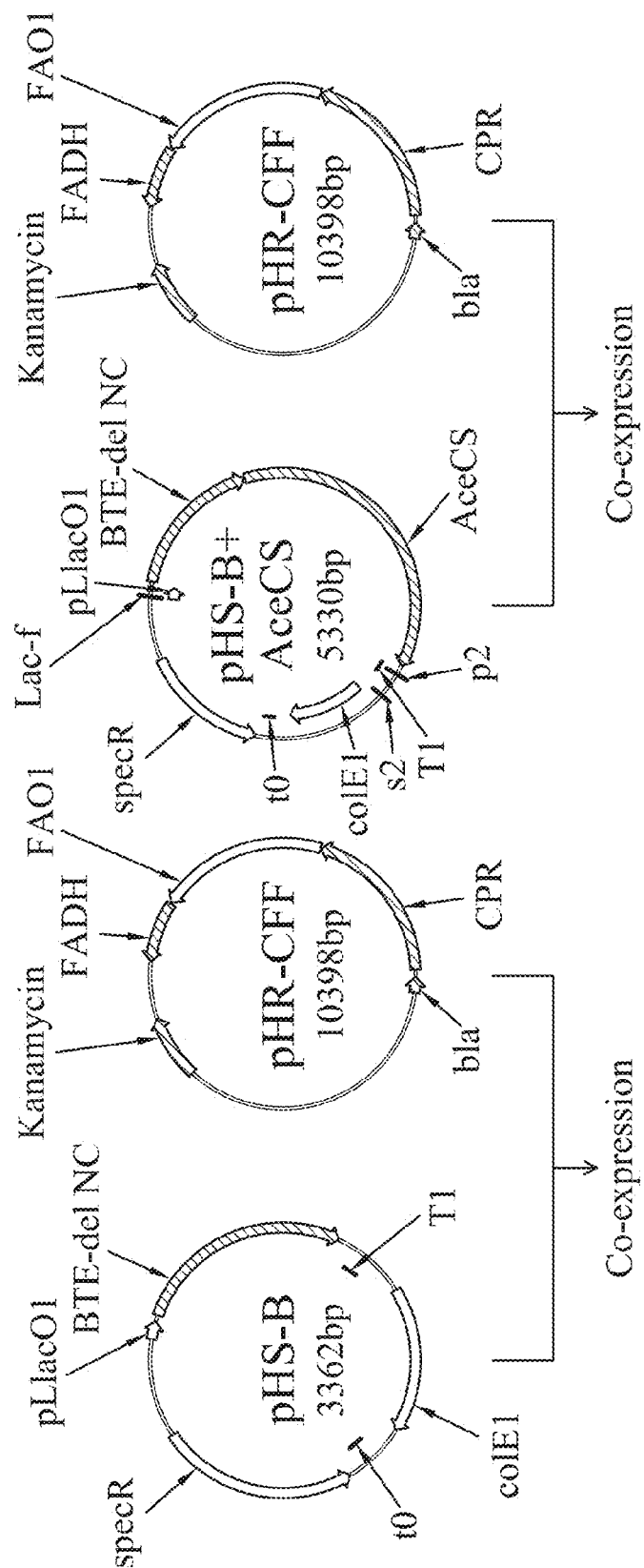
FIG. 11 is a schematic diagram showing expression constructs for generating modified *E. coli* strains E2 and E3.

We also constructed strains E2 (ΔfadD::BTEΔNC::CPR::FAO::FADH) and E3 (ΔfadD::BTEΔNC::AceCS::CPR::FAO::FADH). See FIG. 11. As shown in FIG. 11, construct pHS-B was generated by inserting the BTEΔNC gene into the pHS vector at the Acc65I/BamHI sites. Construct pHS-B+AceCS was generated by inserting the BTEΔNC and FatB3 genes into the Acc65I/SalI and HindIII/BamHI sites of the pHS vector, respectively. pHS-B and pHR-CRR were introduced into host E. coli cells to generate strain E2 and pHS-B+AceCS and pHR-CFF were introduced into host E. coli cells to generate strain E3.

Figure 12:
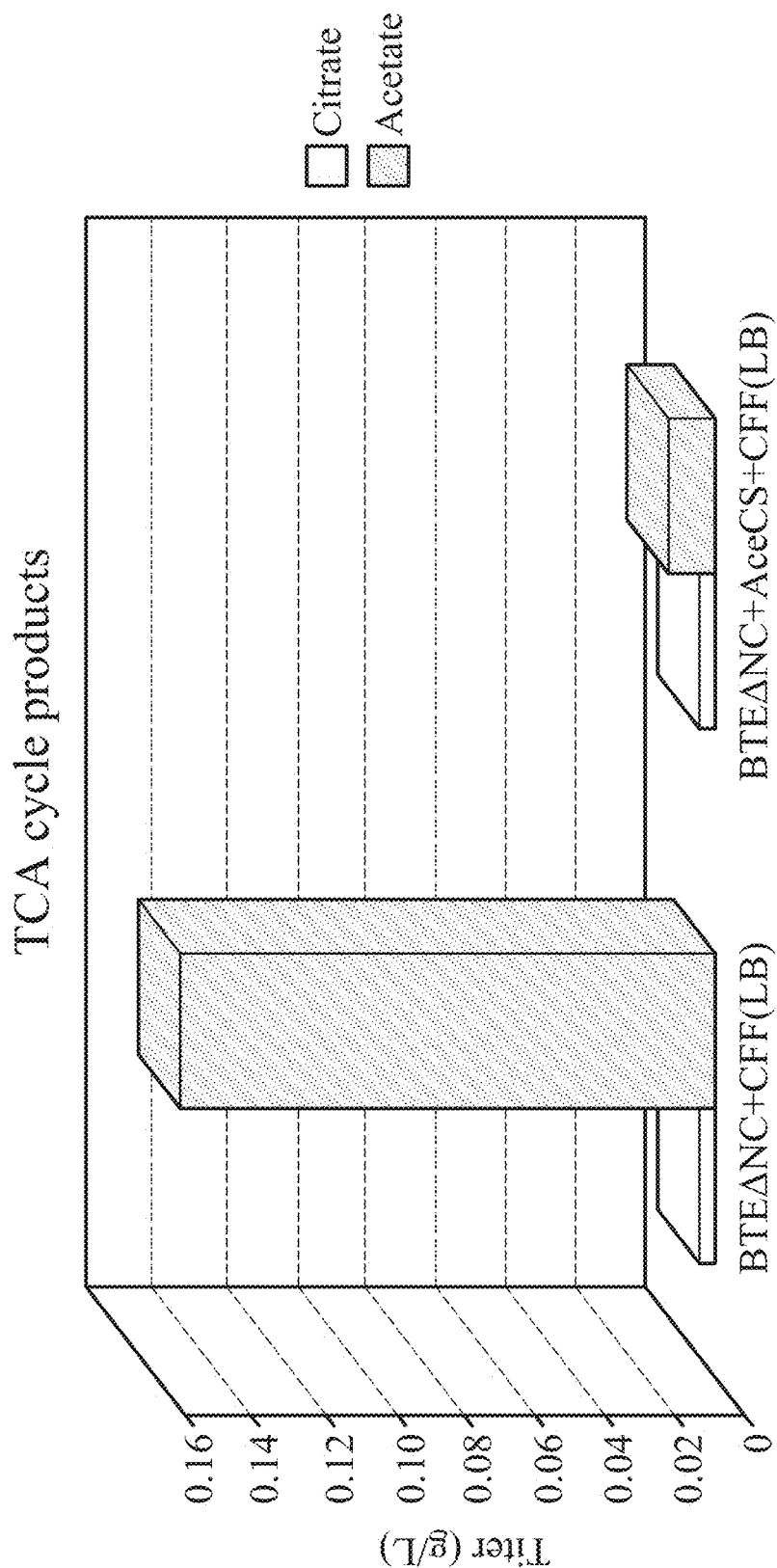
FIG. 12 is a bar graph showing citrate and acetate productions of strains E2 and E3.

Strains E2 and E3 were cultured in LB medium in a fermentor under 1 vvm aeration and at 300 rpm. The pH was maintained at 6.0 for 1 day. Every 6 hours thereafter, additional 1% glucose was added to maintain the pH at 7.5 for two days. Acetate production was measured. As shown in FIG. 12, strain E3 produced less acetate than strain E2.

Figure 13:
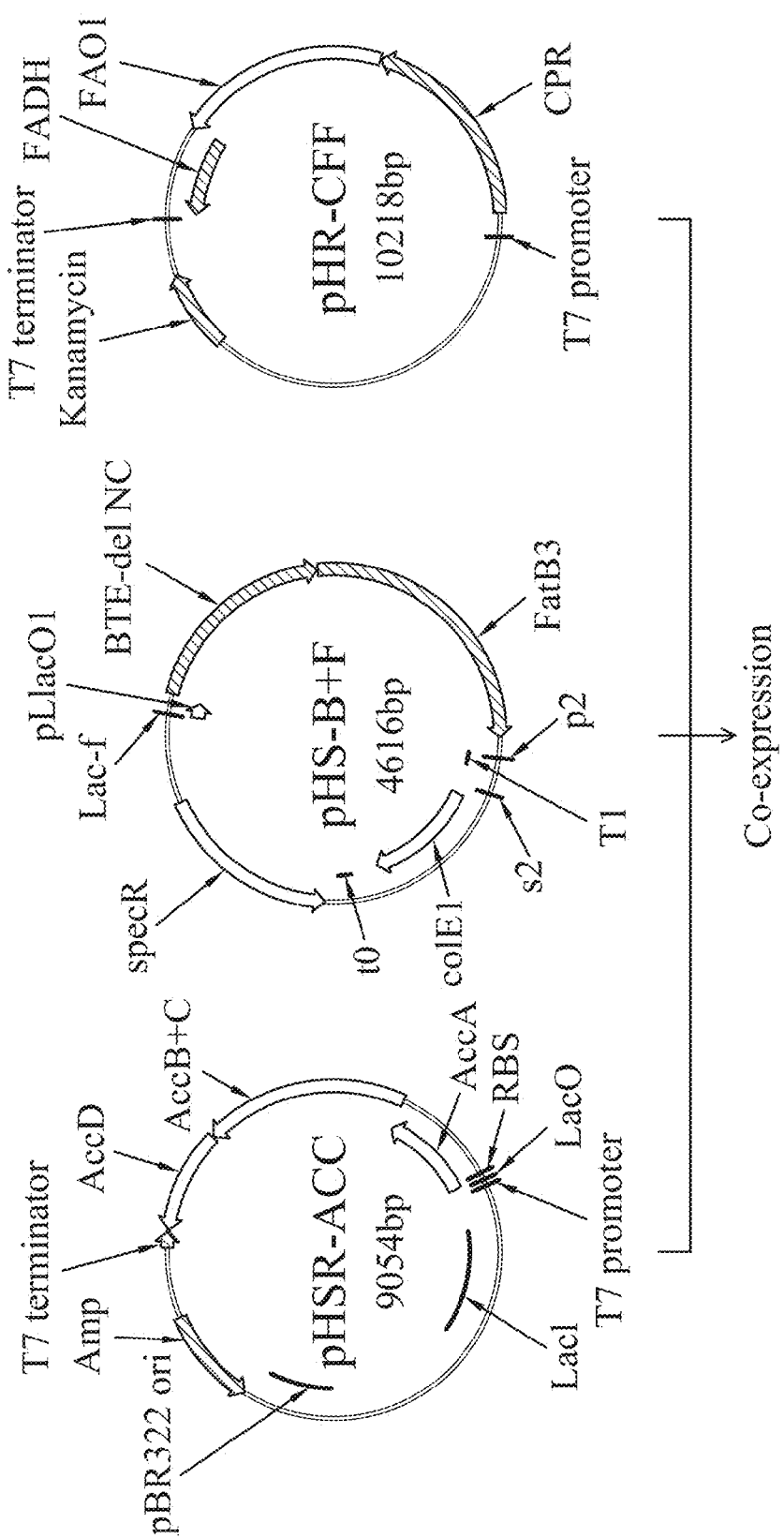
FIG. 13 is a schematic diagram showing expression constructs for generating modified *E. coli* strain E4.

Strain E4 (ΔfadD::ACC::BTEΔNC:: FatB3::CPR::FAO::FADH) was constructed. See FIG. 13. Construct pHSR-ACC was generated by inserting the AccA, AccBC, and AccD genes into the NdeI/SpeI, SpeI/EagI, and EagI/XhoI sites of the pHSR vector, respectively. Constructs pHSR-ACC, pHS-B+F, and pHR-CFF were introduced into host E. coli cells to generate strain E4.

Figure 14:
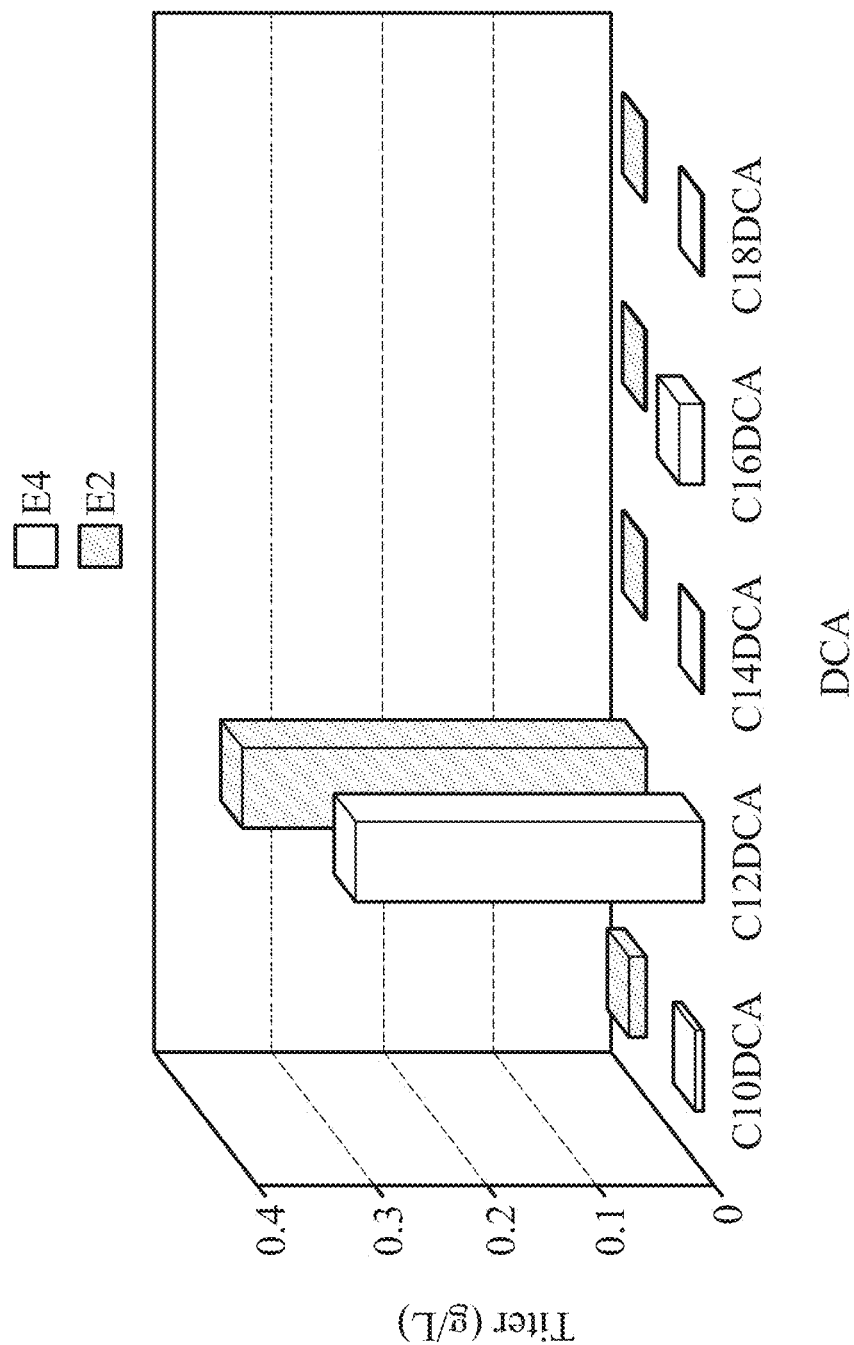
FIG. 14 is a bar graph showing dicarboxylic acid productions of strains E2 and E4.

Strain E2 and E4 were cultured in LB medium in a fermentor under 1 vvm aeration and at 300 rpm. The pH was maintained at 6.0 for 1 day. Every 6 hours thereafter, additional 1% glucose was added to maintain the pH at 7.5 for two days. Dicarboxylic acid production was measured. As shown in FIG. 14, C12DCA production reached 0.36 g/L.

Figure 15:
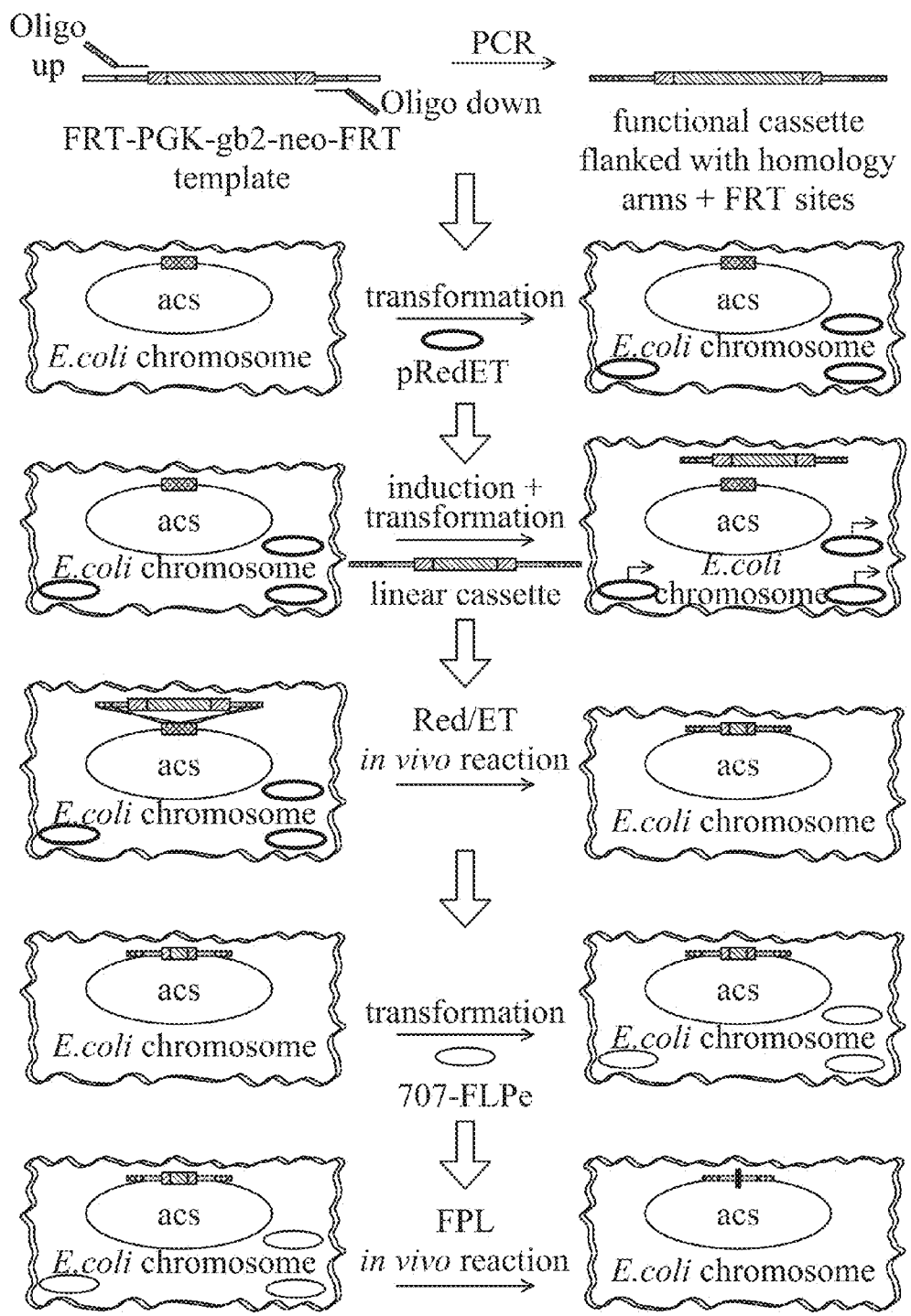
FIG. 15 is a schematic diagram showing construction of *E. coli* strain E5.

Strain E5 (Δacs::CPR::FAO::FADH) was constructed. See FIG. 15. As shown in FIG. 15, a cassette (for knocking out the acs gene) including FRT sites flanked by homology arms were created using PCR using acs forward primer (SEQ ID NO:50) and reverse primer (SEQ ID NO:51). E. coli cells were transformed with pRedET followed by induction and transformation with the linear cassette. The linear cassette was then inserted into the target locus. Construct pHR-CFF was introduced into the Δacs strain.

Figure 16:
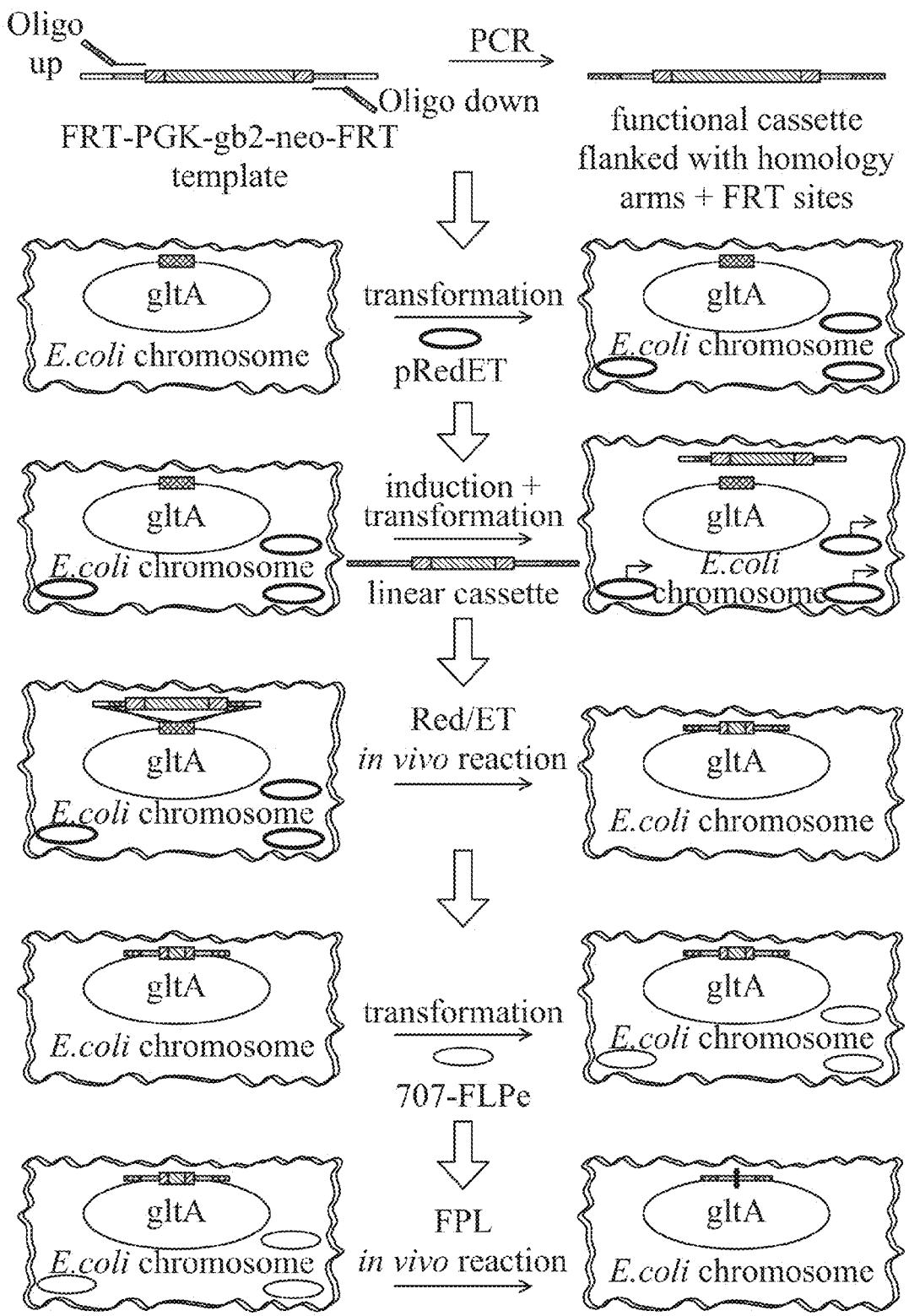
FIG. 16 is a schematic diagram showing construction of *E. coli* strain E6.

Strain E6 (ΔfadD::ΔgltA::CPR::FAO::FADH) was constructed using the same method. See FIG. 16. The functional cassette was generated using PCR using gltA forward primer (SEQ ID NO:52) and gltA reverse primer (SEQ ID NO:53). Construct pHR-CFF was introduced into the ΔgitA strain.

Figure 17:
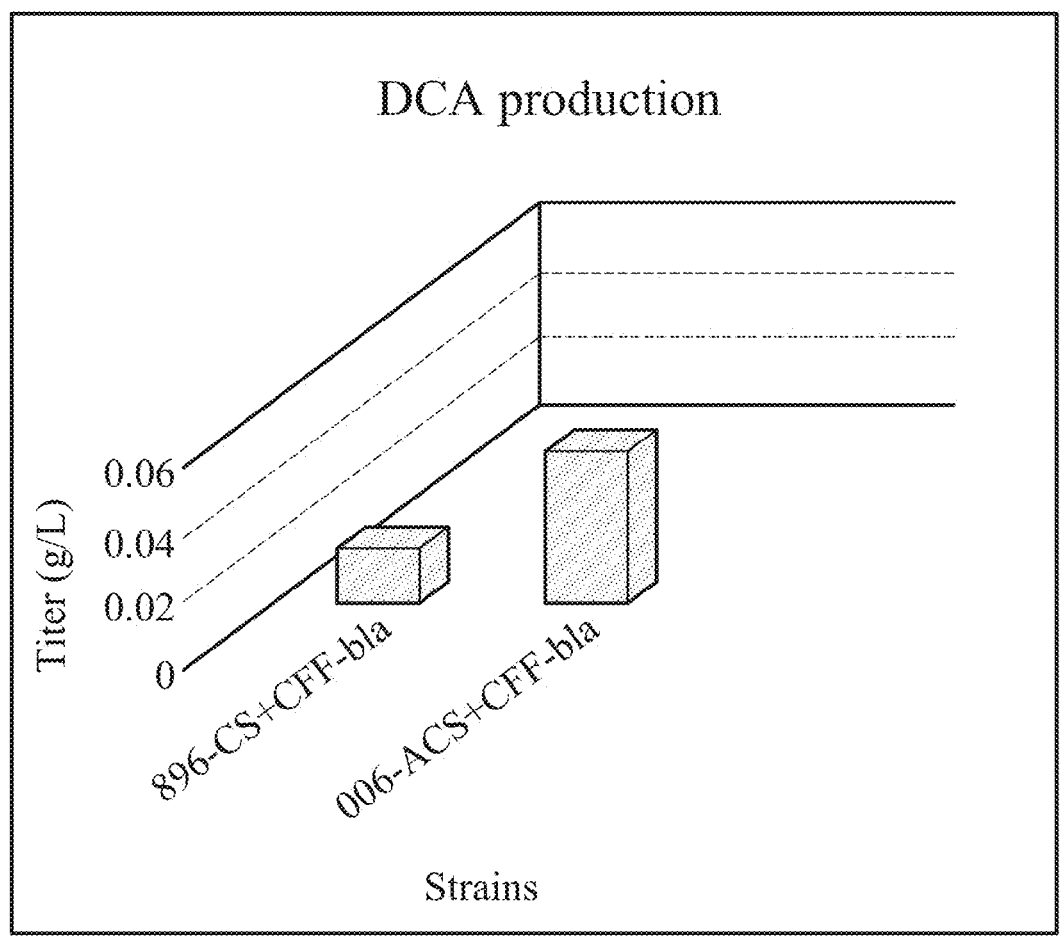
FIG. 17 is a bar graph showing dicarboxylic acid productions of strains E5 and E6.

Strains E5 and E6 were cultured in LB medium in a fermentor under 1 vvm aeration and at 300 rpm. The pH was maintained at 6.5 for 1 day. Every 6 hours thereafter, additional 1% glucose was added to maintain the pH at 7.5 for two days. Dicarboxylic acid production was measured. As shown in FIG. 17, C12DCA production reached 0.02 g/L and 0.05 g/L.

Figure 19:
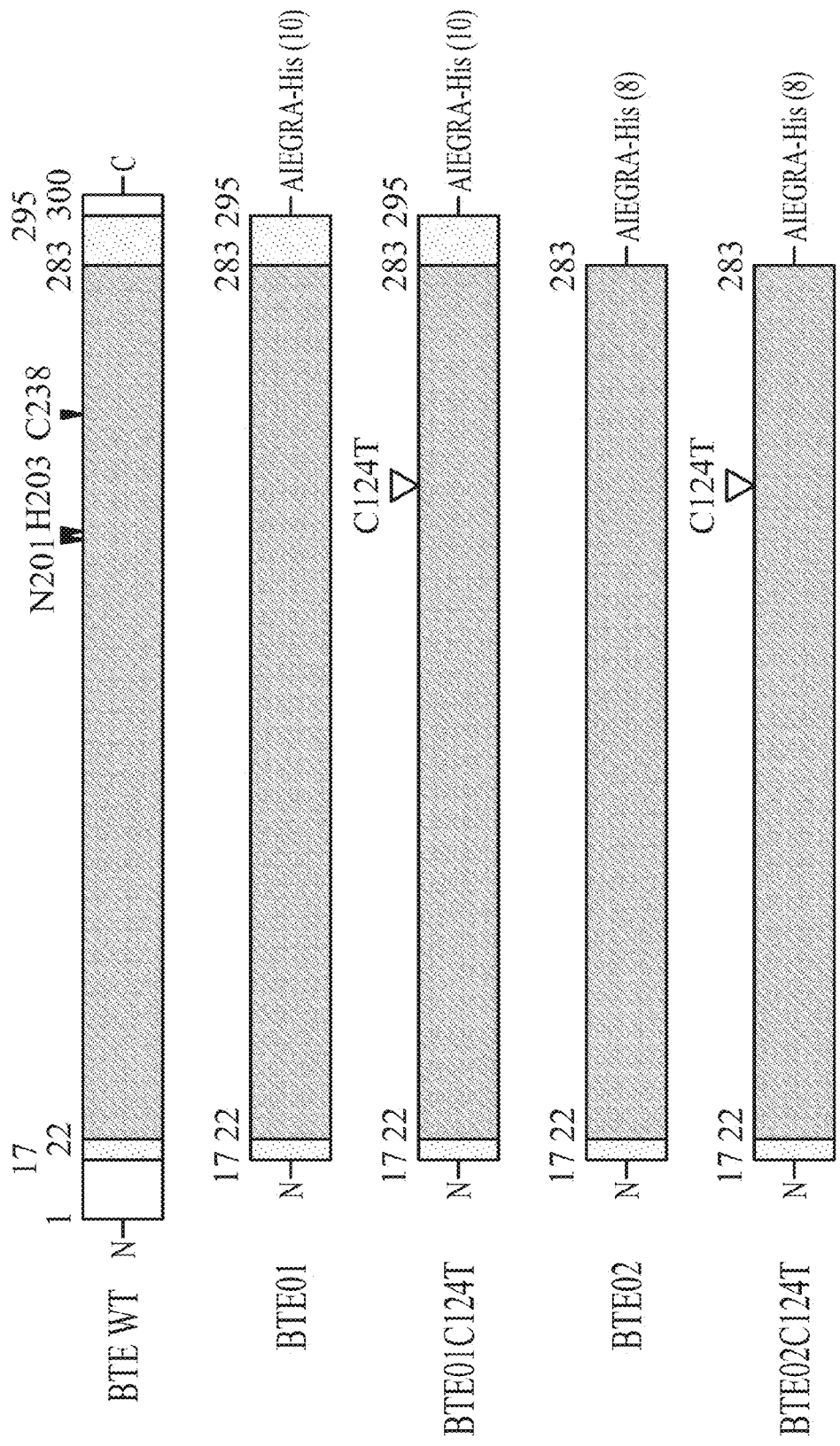
FIG. 19 is a schematic diagram showing the sequence difference between the wild-type BTE and the modified BTEs (BTE 01, BTE01C124T, BTE 02, and BTE02C124T).

The schematic diagram which shows the sequence difference between the wild-type BTE and the modified BTEs (BTE 01, BTE01C124T, BTE 02, and BTE02C124T) is shown in FIG. 19. The enzymes above were synthesized on a codon-optimized basis of the E. coli translational system.

Figure 20B:
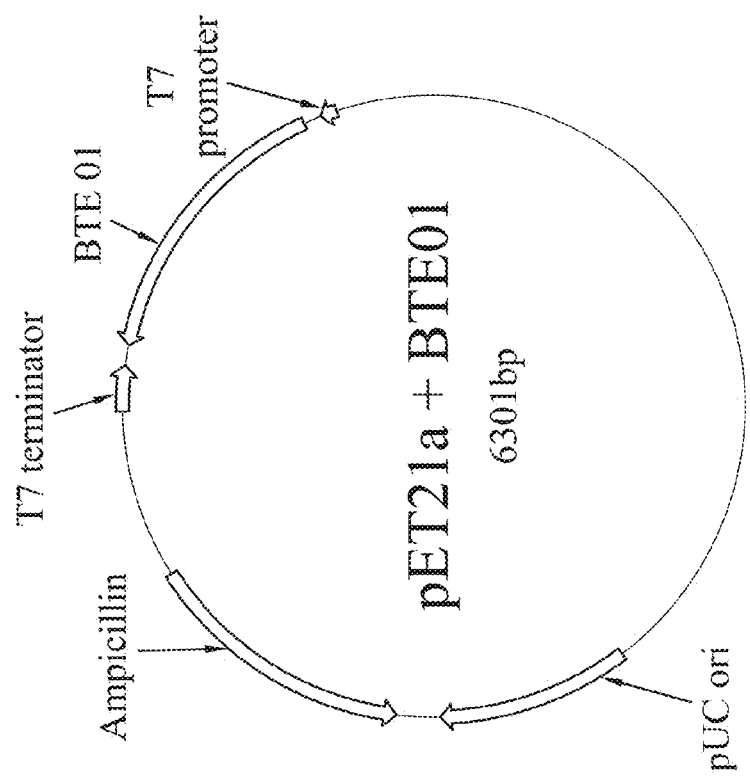
FIGS. 20A-20C are schematic diagrams showing expression cassettes for expressing wild-type lauroyl ACP-thioesterase (BTE WT) in *E. coli* strain E7, expressing modified lauroyl ACP-thioesterase (BTE 01) in *E. coli* strain E8, and expressing modified lauroyl ACP-thioesterase (BTE 02) in *E. coli* strain E9, respectively.
Figure 20A:
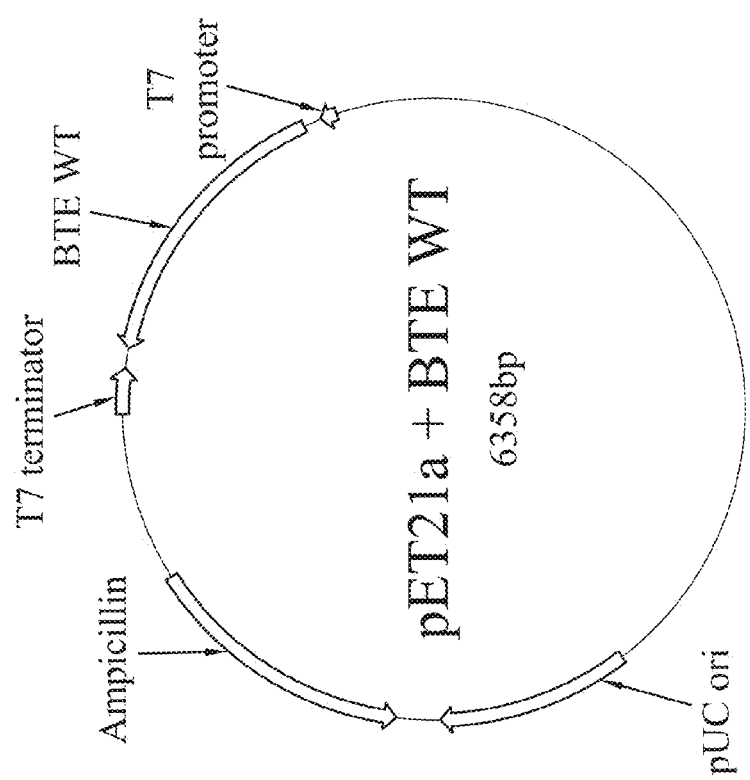
Figure 20C:
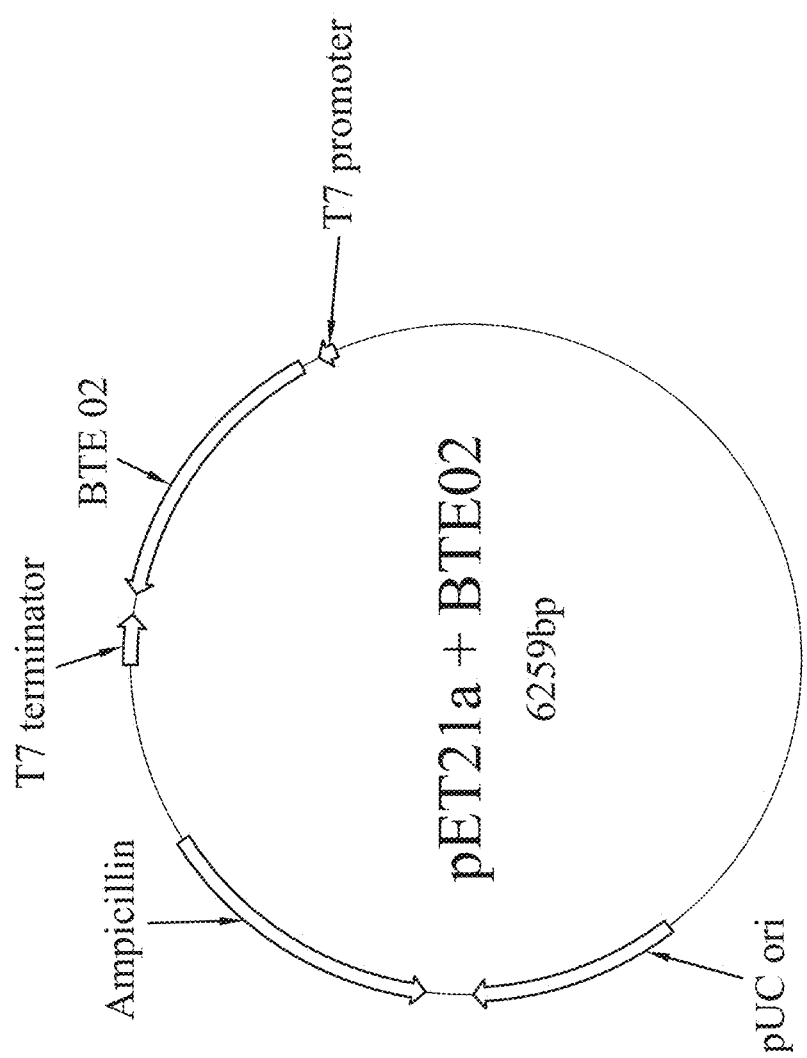

Strain E7 (ΔfadD::ΔgltA::BTE WT), Strain E8 (ΔfadD::ΔgltA::BTE 01) and Strain E9 (ΔfadD::ΔgltA::BTE 02) were constructed. FIG. 20A shows an expression cassette for expressing wild-type lauroyl ACP-thioesterase (BTE WT) in Strain E7, FIG. 20B shows an expression cassette for expressing a modified lauroyl ACP-thioesterase (BTE 01) in Strain E8, and FIG. 20C shows an expression cassette for expressing a modified lauroyl ACP-thioesterase (BTE 02) in Strain E9. In short, the gene of wild-type BTE, and the gene of modified BTE, BTE 01, and the gene of modified BTE, BTE 02, were inserted into pET21a(+) expression vectors at a NdeI/BamHI site and then introduced into E. coli to construct Strain E7, Strain E8 and Strain E9, respectively.

Strain E7, Strain E8 and Strain E9 were cultured in LB medium in a 250 ml shaker bottle at 200 rpm. Wild-type lauroyl ACP-thioesterase was expressed in Strain E7. The modified enzyme (residues 17-295 of wild-type lauroyl ACP-thioesterase) with C-terminal His-tag fusion was expressed in Strain E8 and the modified enzyme (residues 17-283 of wild-type lauroyl ACP-thioesterase) with C-terminal His-tag fusion was expressed in Strain E9, and the modified enzymes were purified using affinity chromatography with the nickel-nitrilotriacetic acid (Ni-NTA) agarose resin.

Figure 21A:
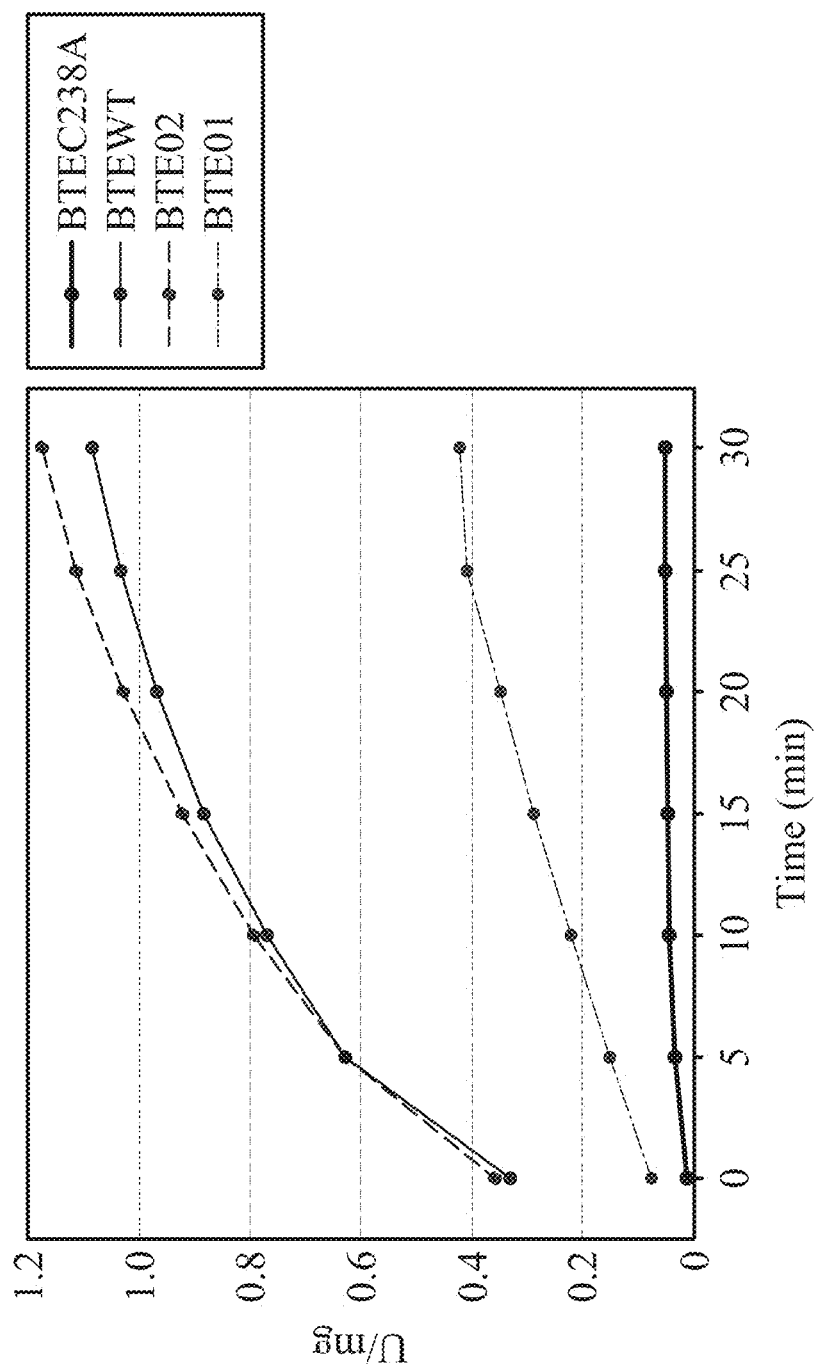
FIGS. 21A and 21B are schematic diagrams showing hydrolysis activities and specificities of the wild-type and modified lauroyl ACP-thioesterases, respectively. BTEC238A is a modified BTE in which cysteine at position 238 is replaced with alanine to lose the enzyme activity, and is used as a negative control. C4, C6, C8, C10 and C12 represent the substrate with 4, 6, 8, 10 or 12 carbons for lauroyl ACP-thioesterases (C4: Succinyl coenzyme A sodium salt; C6: Hexanoyl coenzyme A sodium salt; C8: Octanoyl coenzyme A sodium salt; C10: Decanoyl coenzyme A sodium salt; C12: Lauroyl coenzyme A sodium salt).
Figure 21B:
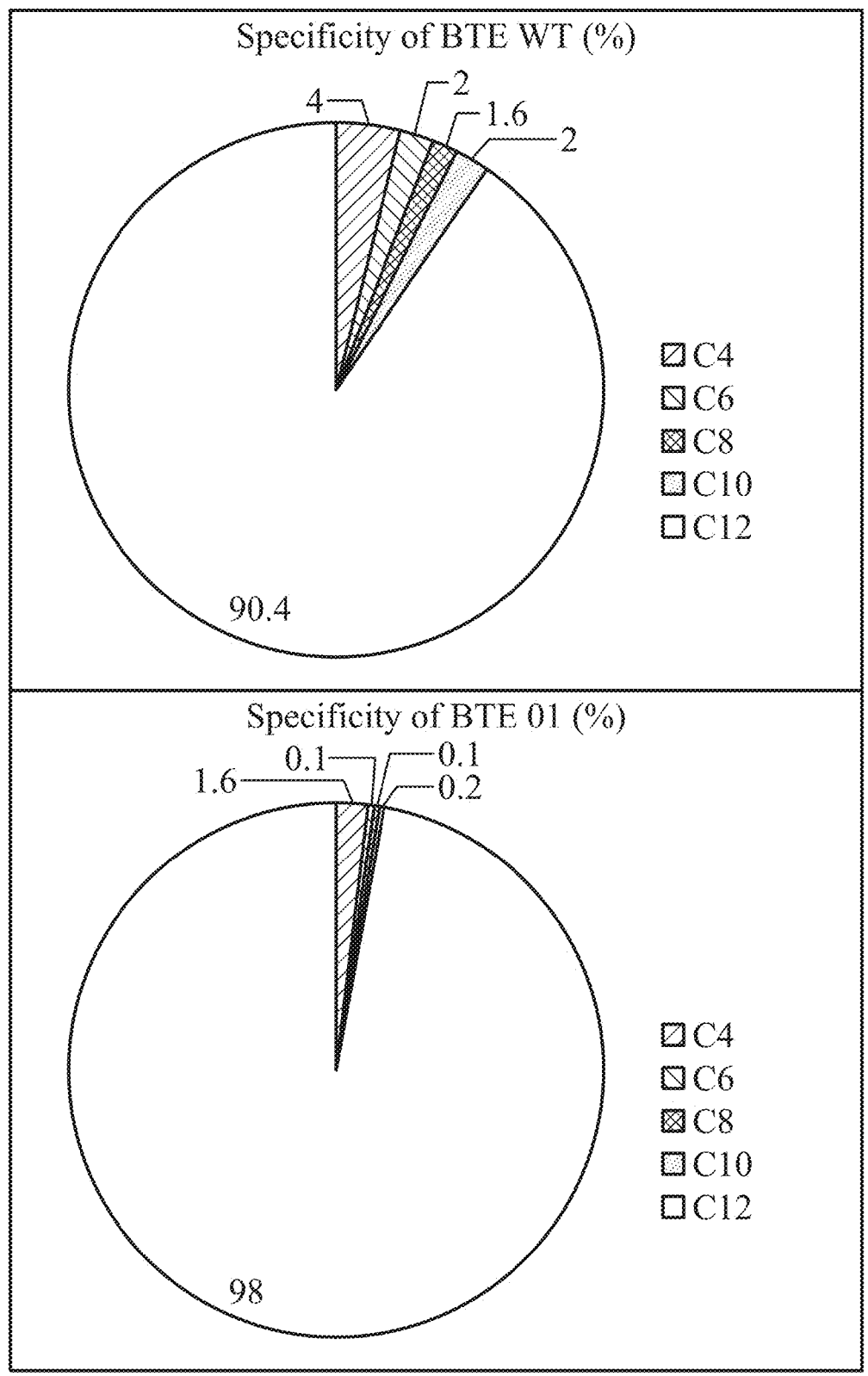
Figure 22A:
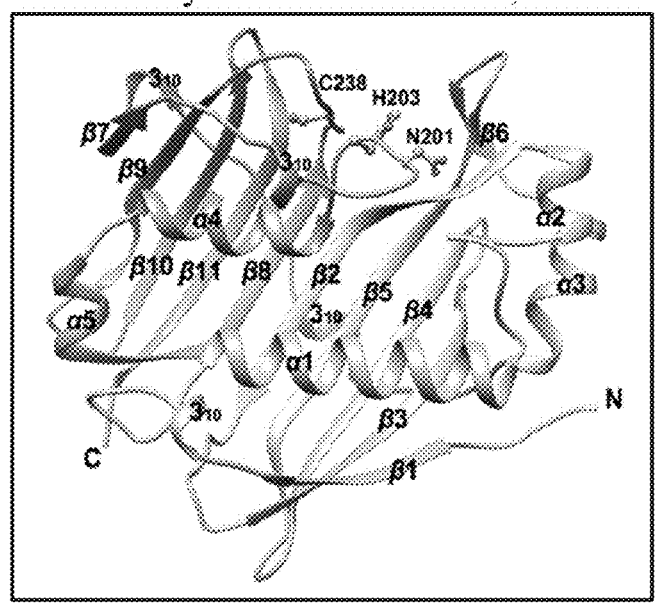
Figure 23:
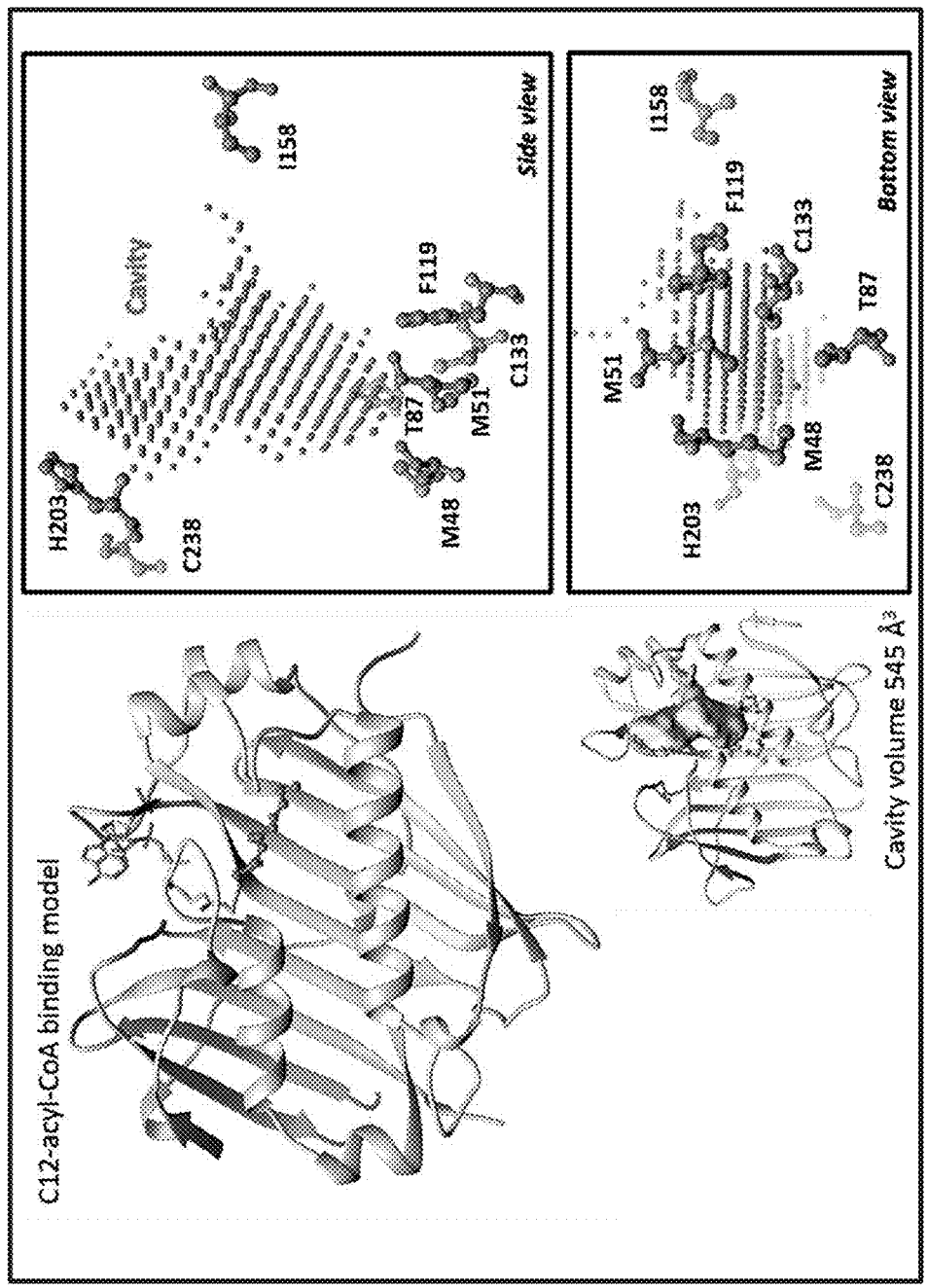
FIG. 23 is a schematic diagram showing the affinity between the modified lauroyl ACP-thioesterase (BTE 02) and C12-acyl-CoA.
Figure 24:
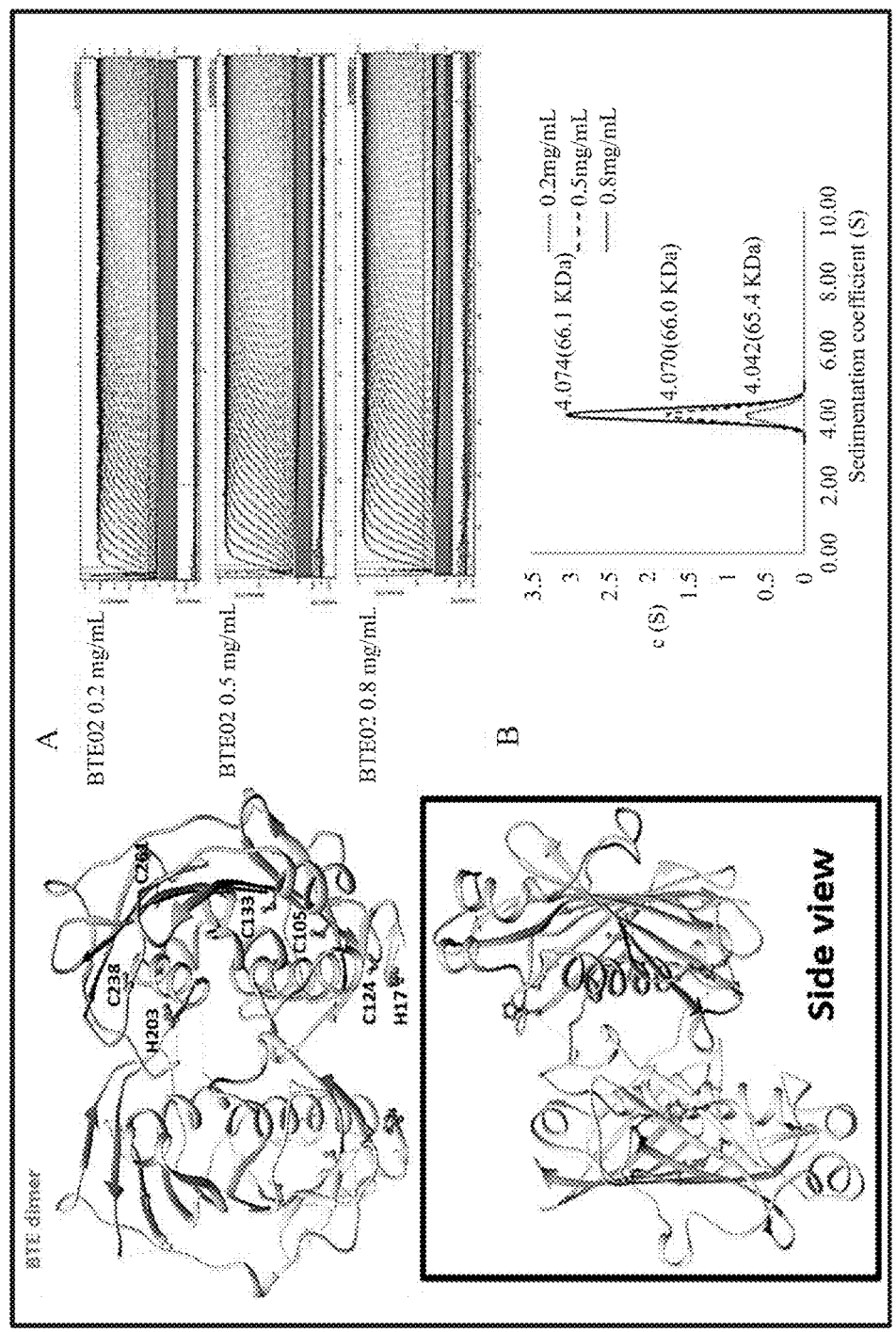
FIG. 24 shows the three dimensional (3D) structure (left part) and sedimentation velocity experiment results of a dimer of the modified lauroyl ACP-thioesterase (BTE 02) (right part). Section A of the right part shows the sedimentation velocity experiment results of BTE02 with concentrations of 0.2 mg/mL, 0.5 mg/mL, and 0.8 mg/mL, in which the results are obtained by sedimentation velocity analytical ultracentrifugation (SV-AUC) assay. Section B of the right part shows the merge data of continuous distribution c(s) of BTE02 with concentrations of 0.2 mg/mL, 0.5 mg/mL, and 0.8 mg/mL.

The enzyme activities of the purified wild-type and modified BTEs were analyzed to compare the activities and specificities of the wild-type and modified BTEs. See FIG. 21A and FIG. 21B.

Figure 25:
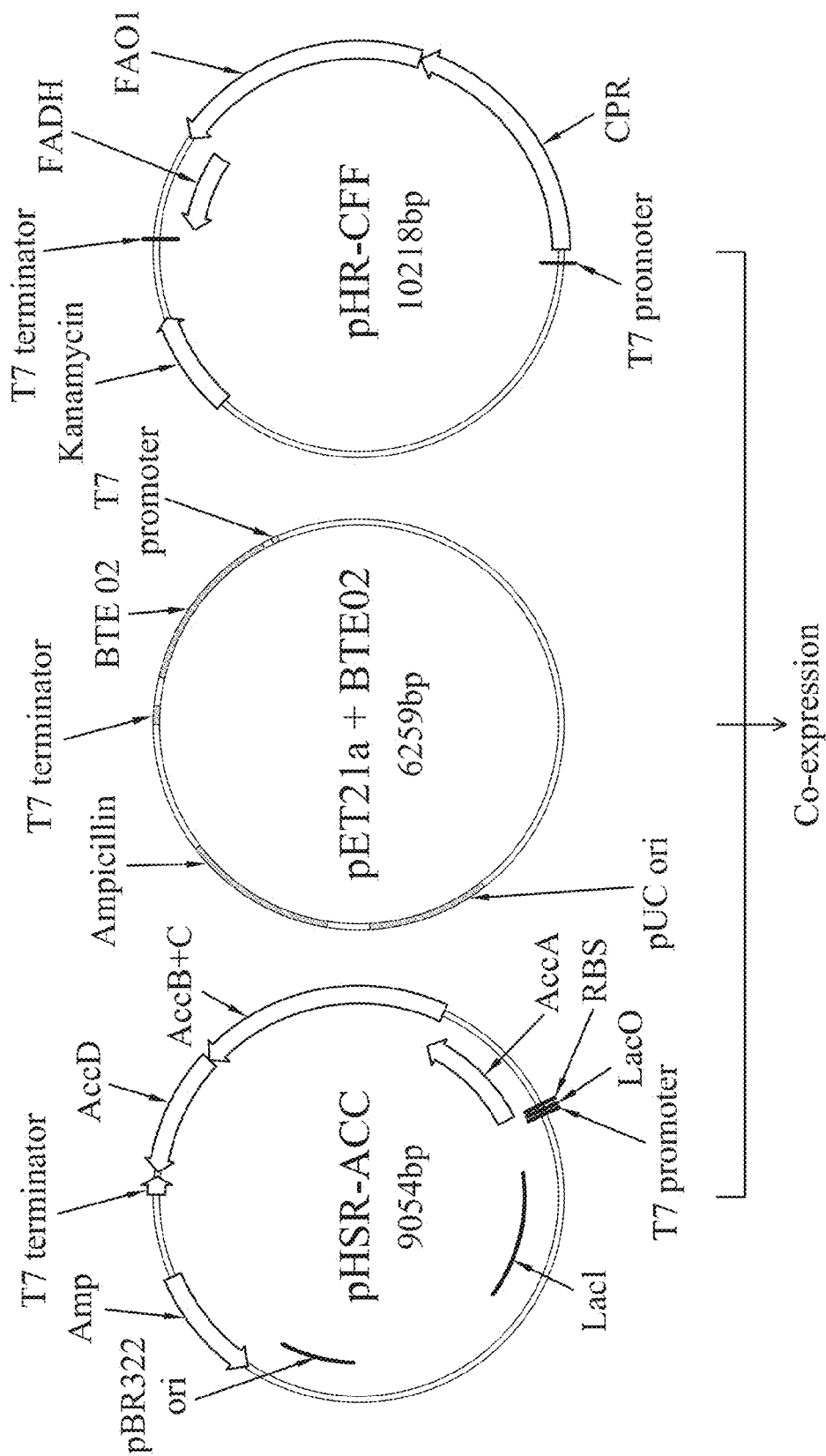
FIG. 25 is a schematic diagram showing an expression cassette for expressing the modified lauroyl ACP-thioesterase (BTE 02) in *E. coli* strain E10.

Strain E10 (ΔfadD::ACC::BTE02::CPR::FAO::FADH) was constructed. See FIG. 25. Construct pHSR-ACC was generated by inserting the AccA, AccBC, and AccD genes into the NdeI/SpeI, SpeI/EagI, and EagI/XhoI sites of the pHSR vector, respectively. Constructs pHSR-ACC, pHS-B+F, and pHR-CFF were introduced into host $E.\ coli$ cells to generate strain E10.

Figure 26:
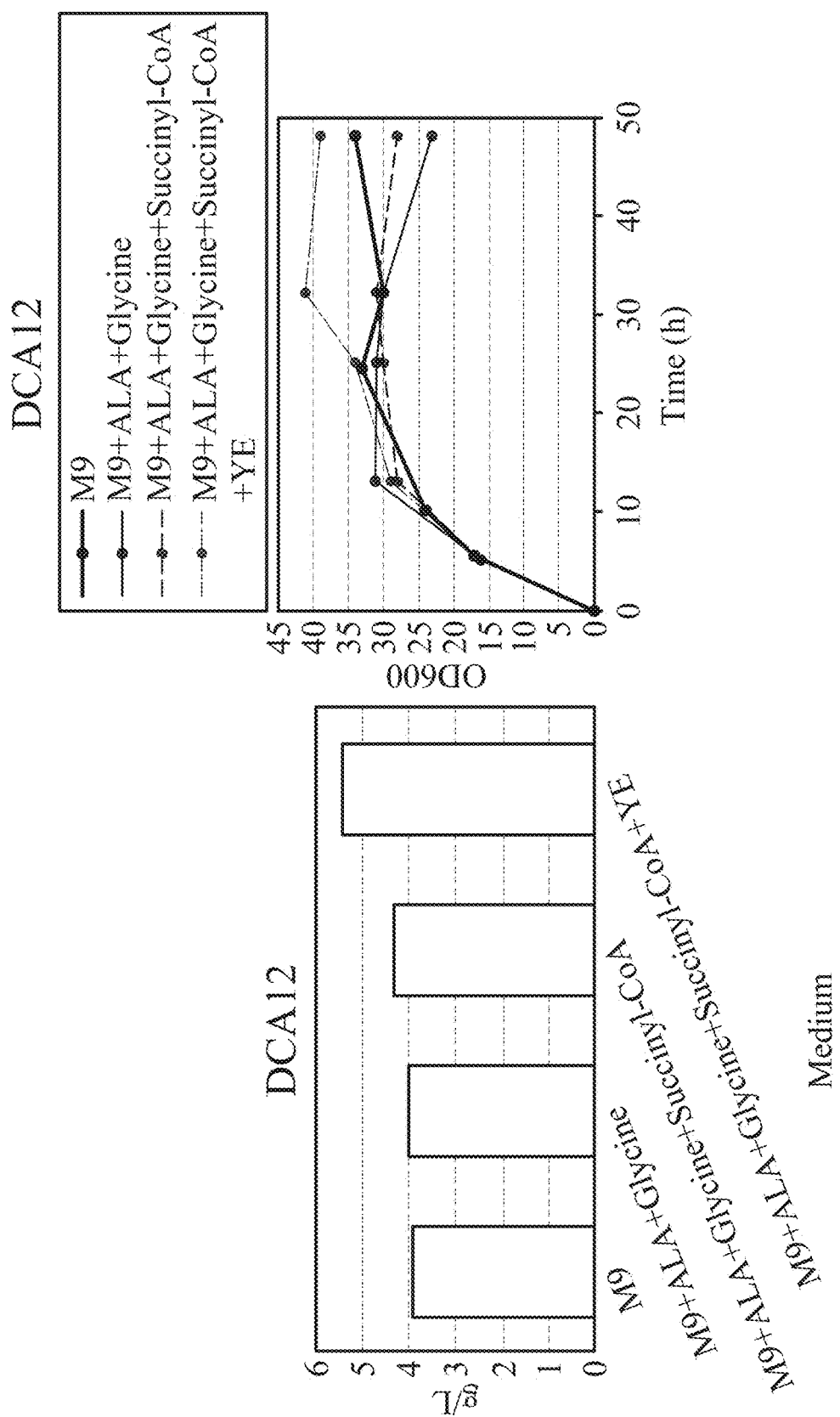
FIG. 26 shows dodecanedioic acid production of *E. coli* strain E10.

Strain E10 was cultured in a M9 minimal medium which contains micronutrient components, without or with additional ingredients (ALA (5-aminolevulinic acid hydrochloride) (0.012 g/L)+glycine (0.075 g/L), ALA (0.012 g/L)+glycine (0.075 g/L)+succinyl-CoA (0.01 g/L), or ALA (0.012 g/L)+glycine (0.075 g/L)+succinyl-CoA (0.01 g/L)+yeast extract (30 g/L)) in a 250 ml shaker bottle at 200 rpm. The ingredients of M9 minimal medium are shown in Table 10, and the micronutrient components are shown in Table 11. Every 6 hours thereafter, additional 1% glucose was added for 2 days. Strain E10 expressed the modified BTE, BTE 02, and the DCA12 production reached 5.4 g/L. See FIG. 26.

TABLE 10

M9 Minimal Medium

| Ingredient | Concentration |
|---|---|
| $Na_2HPO_4 \cdot 7H_2O$ | 12.8 g/L |
| $KH_2PO_4$ | 3 g/L |
| NaCl | 0.5 g/L |
| $NH_4Cl$ | 1 g/L |

TABLE 11

Micronutrient components added to M9 Minimal Medium

| Stock Concentration | Micronutrient | Final Concentration |
|---|---|---|
| 1M | $MgSO_4$ | 1 mM |
| 1M | $CaCl_2$ | 100 μM |
| 3 mM | $(NH_4)_6Mo_7O_{24} \cdot 4H_2O$ | $3 \times 10^{-9}$ M |
| 400 mM | $H_3BO_3$ | $4 \times 10^{-7}$ M |
| 30 mM | $CoCl_2 \cdot 6H_2O$ | $3 \times 10^{-8}$ M |
| 10 mM | $CuSO_4 \cdot 5H_2O$ | $1 \times 10^{-8}$ M |
| 80 mM | $MnCl_2 \cdot 4H_2O$ | $8 \times 10^{-8}$ M |
| 10 mM | $ZnSO_4 \cdot 7H_2O$ | $1 \times 10^{-8}$ M |
| 8 mM | $FeSO_4 \cdot 7H_2O$ | $1 \times 10^{-6}$ M |

Three dimensional (3D) structure analysis of the modified lauroyl-acyl carrier protein (ACP) thioesterase (BTE 02)

The crystal structure of BTE displays the "double-hot-dog fold". The continuous polypeptide chain starts at residue 17 and terminates at residue 283, with five α helices, eleven β strands and four $3_{10}$ helices. Residues 17-161 and 186-283 fold into the N-terminal and C-terminal hot-dog folds, respectively. Two individual folds come together to create an extended β-sheet centered on a pseudo-two-fold axis. Residues 162-185 make up a loop connecting two core domains that contact the extended β-sheet opposite the side containing the wrapped α-helices. The large surface area buried (1500 Å$^2$, PISA calculated) between the monomer indicates the dimerization of BTE, which was confirmed by sedimentation velocity (SV) analysis. The major signal appeared at a sedimentation coefficient (S) value of 4.07 with different protein concentrations (0.2, 0.5 and 0.8 mg mL$^{-1}$), corresponding to a molecular mass of 66.1 kDa for the dimeric assembly of BTE. Two dyad-related monomers were associated into a dimer via hydrogen bonds, salt bridges and hydrophobic interactions between helices α1, α4, and α5 from each monomer, as well as the $3_{10}$ helices and contacting loops. Without bound substrates, the catalytic pocket was initially predicted by structural superimposition with a known hTHEM2/undecan-2-one-CoA complex structure, thioesterase hTHEM2 from the Homo (PDB code: 3F50). When the BTE core structure was superimposed onto the hTHEM2 dimer structure, the two structures were superimposed well by a root-mean-square deviation (r.m.s.d.) of 0.761 Å for 64 pairs of α-carbon atoms. In the catalytic pocket, the three positions that could potentially serve as the general base or acid for chemical reaction include residues N201, H203 and C238. See FIGS. 22A and 22B, FIG. 23 and FIG. 24.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A genetically modified microorganism, comprising a nucleic acid encoding an *Umbellularia californica* lauroyl acyl carrier protein (ACP)-thioesterase (BTE) operably linked to a promoter, wherein the microorganism produces an increased amount of medium-chain lauric acid and/or dodecanedioic acid as compared to the unmodified parent of the microorganism, wherein the *Umbellularia californica* lauroyl ACP-thioesterase (BTE) is a modified *Umbellularia californica* lauroyl ACP-thioesterase (BTE), and the modified *Umbellularia californica* lauroyl ACP-thioesterase (BTE) consists of residues 17-283 of a wild-type *Umbellularia californica* lauroyl ACP-thioesterase (BTE) or consists of residues 17-283 of a wild-type *Umbellularia californica* lauroyl ACP-thioesterase (BTE) and a C-terminal His-tag fusion, wherein the amino acid sequence of the wild-type *Umbellularia californica* is the sequence of SEQ ID NO: 20.

2. The genetically modified microorganism of claim 1, further comprising one or more additional nucleic acids each operably linked to a promoter, each additional nucleic acid encoding a protein selected from the group consisting of an acetyl-CoA carboxylase (ACC), an acetyl-CoA carboxylase carboxyl transferase subunit α (AccA), an acetyl-CoA carboxylase biotin carboxyl carrier protein (AccB), an acetyl-CoA biotin carboxylase (AccC), an acetyl-CoA carboxylase transferase subunit β (AccD), a fatty acid synthase (FAS) subunit, a cytochrome P450 reductase (CPR), a long-chain alcohol oxidase (FAO1), a long-chain alcohol dehydrogenase (FADH), and an adenosine monophosphate-forming acetyl-coenzyme A synthetase (AceCS).

3. The genetically modified microorganism of claim 1, further comprising additional nucleic acids each encoding a CPR, a FAO1, and a FADH, respectively.

4. The genetically modified microorganism of claim 1, further comprising a loss-of-function mutation in or expressing a lower level of one or more genes selected from the group consisting of a palmitoyl-acyl carrier protein (ACP) thioesterase gene, an acyl-coenzyme A oxidase gene, a citric synthetase (gltA) gene, or an acyl-coenzyme A synthetase (acs) gene.

5. The genetically modified microorganism of claim 1, further comprising a loss-of-function mutation in or expressing a lower level of an acyl-coenzyme A oxidase gene.

6. The genetically modified microorganism of claim 5, wherein the acyl-coenzyme A oxidase gene is acyl-CoA oxidase 2 (pox2), acyl-CoA oxidase 5 (pox5), or acyl-CoA synthetase (fadD).

7. The genetically modified microorganism of claim 1, wherein the microorganism (1) contains a loss-of-function mutation in or expresses a lower level of an acyl-coenzyme A oxidase gene and (2) contains additional nucleic acids each encoding a CPR, a FAO1, and a FADH, respectively.

8. The genetically modified microorganism of claim 7, wherein the acyl-coenzyme A oxidase gene is fadD.

9. The genetically modified microorganism of claim 1, wherein the microorganism is *Yarrowia lipolytica* or *Escherichia coli*.

10. A method of producing a medium-chain lauric acid and/or dodecanedioic acid, the method comprising:
   providing the genetically-modified microorganism of claim 1; and
   culturing the microorganism in a culture medium containing glucose or glycerol at pH 6 to 8 under conditions that allow production of the medium-chain lauric acid and/or dodecanedioic acid;
   whereby the microorganism produces the medium-chain lauric acid and/or dodecanedioic acid.

* * * * *

SEQUENCE LISTING

<160> NUMBER OF SEQ ID NOS: 53

<210> SEQ ID NO 1

```
<211> LENGTH: 6801
<212> TYPE: DNA
<213> ORGANISM: Yarrowia lipolytica
<220> FEATURE:
<221> NAME/KEY: misc_feature
<223> OTHER INFORMATION: biotin carboxylase

<400> SEQUENCE: 1
atgcgactgc aattgaggac actaacacgt cggtttttca gtatggcttc aggatcttca      60
acgccagatg tggctcccct ggtggacccc aacattcaca aaggtctcgc ctctcatttc     120
tttggactca attctgtcca cacagccaag ccctcaaaag tcaaggagtt tgtggcttct     180
cacggaggtc atacagttat caacaaggtc ctcatcgcta acaacggtat tgccgcagta     240
aaggagatcc gttcagtacg aaaatgggcc tacgagacct ttggcgacga gcgagcaatc     300
tcgttcaccg tcatggccac ccccgaagat ctcgctgcca cgccgactga cattagaatg     360
gccgatcagt acgtcgaggt gcccggagga accaacaaca caactacgc caacgtcgag      420 ctgattgtcg acgtggctga gcgattcggc gtcgatgccg tgtgggccgg atggggccat     480
gccagtgaaa tcccctgct ccccgagtcg ctagcggcct ctccccgcaa gattgtcttc      540
atcggccctc ccggagctgc catgagatct ctgggagaca aaatttcttc taccattgtg     600
gcccagcacg caaaggtccc gtgtatcccg tggtctggaa ccggagtgga cgaggttgtg     660
gttgacaaga gcaccaacct cgtgtccgtg tccgaggagg tgtacaccaa gggctgcacc     720
accggtccca agcagggtct ggagaaggct aagcagattg gattcccgt gatgatcaag      780 gcttccgagg gaggaggagg aaagggtatt cgaaaggttg agcgagagga ggacttcgag     840
gctgcttacc accaggtcga gggagagatc cccggctcgc ccatcttcat tatgcagctt     900
gcaggcaatg cccggcattt ggaggtgcag cttctggctg atcagtacgg caacaatatt     960
tcactgtttg tcgagattg ttcggttcag cgacggcatc aaaagattat tgaggaggct     1020
cctgtgactg tggctggcca gcagaccttc actgccatgg agaaggctgc cgtgcgactc     1080
ggtaagcttg tcggatatgt ctctgcaggt accgttgaat atctgtattc ccatgaggac     1140
gacaagttct acttcttgga gctgaatcct cgtcttcagg tcgaacatcc taccaccgag     1200
atggtcaccg gtgtcaacct gccgctgcc cagcttcaga tcgccatggg tatccccctc      1260
gatcgaatca aggacattcg tctcttttac ggtgttaacc ctcacaccac cactccaatt     1320
gatttcgact ctcgggcga ggatgctgat aagacacagc gacgtcccgt ccccgaggt       1380 cacaccactg cttgccgaat cacatccgag gaccctggag agggtttcaa gccctccgga     1440
ggtactatgc acgagctcaa cttccgatcc tcgtccaacg tgtggggtta cttctccgtt     1500
ggtaaccagg gaggtatcca ttcgttctcg gattcgcagt ttggtcacat cttcgccttc     1560
ggtgagaacc gaagtcgtc tcgaaagcac atggttgttg ctttgaagga actatctatt      1620
cgaggtgact tccgaaccac cgtcgagtac ctcatcaagc tgctggagac accggacttc     1680
gaggacaaca ccatcaccac cggctggctg atgagctta tctccaacaa gctgactgcc      1740
gagcgacccg actcgttcct cgctgttgtt tgtggtgctg ctaccaaggc ccatcgagct     1800
tccgaggact ctattgccac ctacatggct tcgctagaga agggccaggt ccctgctcga     1860
gacattctca agaccctttt ccccgttgac ttcatctacg agggccagcg gtacaagttc     1920
accgccaccc ggtcgtctga ggactcttac acgctgttca tcaacggttc tcgatgcgac     1980
attggagtta gacctctttc tgacggtggt attctgtgtc ttgtaggtgg agatcccac      2040 aatgtctact ggaaggagga ggttggagcc acgcgactgt ctgttgactc caagacctgc     2100
```

```
cttctcgagg tggagaacga ccccactcag cttcgatctc cctctcccgg taagctggtt    2160
aagttcctgg tcgagaacgg cgaccacgtg cgagccaacc agccctatgc cgagattgag    2220
gtcatgaaga tgtacatgac tctcactgct caggaggacg gtattgtcca gctgatgaag    2280
cagcccggtt ccaccatcga ggctggcgac atcctcggta tcttggccct tgatgatcct    2340
tccaaggtca agcatgccaa gccctttgag ggccagcttc ccgagcttgg accccccact    2400
ctcagcggta caagcctca tcagcgatac gagcactgcc agaacgtgct ccataacatt    2460
ctgcttggtt tcgataacca ggtggtgatg aagtccactc ttcaggagat ggttggtctg    2520
ctccgaaacc ctgagcttcc ttatctccag tgggctcatc aggtgtcttc tctgcacacc    2580
cgaatgagcg ccaagctgga tgctactctt gctggtctca ttgacaaggc caagcagcga    2640
ggtggcgagt ttcctgccaa gcagcttctg cgagcccttg agaaggaggc gagctctggc    2700
gaggtcgatg cgctcttcca gcaaactctt gctcctctgt ttgaccttgc tcgagagtac    2760
caggacggtc ttgctatcca cgagcttcag gttgctgcag gccttctgca ggcctactac    2820
gactctgagg cccggttctg cggacccaac gtacgtgacg aggatgtcat tctcaagctt    2880
cgagaggaga accgagattc tcttcgaaag gttgtgatgg cccagctgtc tcattctcga    2940
gtcggagcca agaacaacct tgtgctggcc cttctcgatg aatacaaggt ggccgaccag    3000
gctggcaccg actctcctgc ctccaacgtg cacgttgcaa agtacttgcg acctgtgctg    3060
cgaaagattg tggagctgga atctcgagct tctgccaagg tatctctgaa agcccgagag    3120
attctcatcc agtgcgctct gccctctcta aaggagcgaa ctgaccagct tgagcacatt    3180
ctgcgatctt ctgtcgtcga gtctcgatac ggagaggttg gtctggagca ccgaactccc    3240
cgagccgata ttctcaagga ggttgtcgac tccaagtaca ttgtctttga tgtgcttgcc    3300
cagttctttg cccacgatga tccctggatc gtccttgctg ccctggagct gtacatccga    3360
cgagcttgca aggcctactc catcctggac atcaactacc accaggactc ggacctgcct    3420
cccgtcatct cgtggcgatt tagactgcct accatgtcgt ctgctttgta caactcagta    3480
gtgtcttctg gctccaaaac ccccacttcc ccctcggtgt ctcgagctga ttccgtctcc    3540
gacttttcgt acaccgttga gcgagactct gctcccgctc gaaccggagc gattgttgcc    3600
gtgcctcatc tggatgatct ggaggatgct ctgactcgtg ttctggagaa cctgcccaaa    3660
cggggcgctg tcttgccat tctgttggt gctagcaaca agagtgccgc tgcttctgct    3720
cgtgacgctg ctgctgctgc cgcttcatcc gttgacactg gcctgtccaa catttgcaac    3780
gttatgattg tcgggttga tgagtctgat gacgacgaca ctctgattgc ccgaatctcc    3840
caggtcattg aggactttaa ggaggacttt gaggcctgtt ctctgcgacg aatcaccttc    3900
tccttcggca actcccgagg tacttatccc aagtatttca cgttccgagg ccccgcatac    3960
gaggaggacc ccactatccg acacattgag cctgctctgg ccttccagct ggagctcgcc    4020
cgtctgtcca acttcgacat caagcctgtc cacaccgaca accgaaacat ccacgtgtac    4080
gaggctactg gcaagaacgc tgcttccgac aagcggttct tcacccgagg tatcgtacga    4140
cctggtcgtc ttcgagagaa catccccacc tcggagtatc tcatttccga ggctgaccgg    4200
ctcatgagcg atattttgga cgctctagag gtgattggaa ccaccaactc ggatctcaac    4260 cacatttttca tcaacttctc agccgtcttt gctctgaagc ccgaggaggt tgaagctgcc    4320
tttggcggtt tcctggagcg atttggccga cgtctgtggc gacttcgagt caccggtgcc    4380
gagatccgaa tgatggtatc cgaccccgaa actggctctg ctttccctct gcgagcaatg    4440
atcaacaacg tctctggtta cgttgtgcag tctgagctgt acgctgaggc caagaacgac    4500
```

```
aagggccagt ggattttcaa gtctctgggc aagcccggct ccatgcacat gcggtctatc   4560
aacactccct accccaccaa ggagtggctg cagcccaagc ggtacaaggc ccatctgatg   4620
ggtaccacct actgctatga cttccccgag ctgttccgac agtccattga gtcggactgg   4680
aagaagtatg acggcaaggc tcccgacgat ctcatgactt gcaacgagct gattctcgat   4740
gaggactctg gcgagctgca ggaggtgaac cgagagcccg gcgccaacaa cgtcggtatg   4800
gttgcgtgga gtttgaggc caagaccccc gagtaccctc gaggccgatc tttcatcgtg   4860
gtggccaacg atatcacctt ccagattggt tcgtttggcc ctgctgagga ccagttcttc   4920
ttcaaggtga cggagctggc tcgaaagctc ggtattcctc gaatctatct gtctgccaac   4980
tctggtgctc gaatcggcat tgctgacgag ctcgttggca agtacaaggt tgcgtggaac   5040
gacgagactg accccctccaa gggcttcaag tacctttact tcaccccctga gtctcttgcc   5100 accctcaagc ccgacactgt tgtcaccact gagattgagg aggagggtcc caacggcgtg   5160
gagaagcgtc atgtgatcga ctacattgtc ggagagaagg acggtctcgg agtcgagtgt   5220
ctgcggggct ctggtctcat tgcaggcgcc acttctcgag cctacaagga tatcttcact   5280
ctcactcttg tcacctgtcg atccgttggt atcggtgctt accttgttcg tcttggtcaa   5340
cgagccatcc agattgaggg ccagcccatc attctcactg gtgcccccgc catcaacaag   5400
ctgcttggtc gagaggtcta ctcttccaac ttgcagcttg gtggtactca gatcatgtac   5460
aacaacggtg tgtctcatct gactgcccga gatgatctca acggtgtcca caagatcatg   5520
cagtggctgt catacatccc tgcttctcga ggtcttccag tgcctgttct ccctcacaag   5580
accgatgtgt gggatcgaga cgtgacgttc cagcctgtcc gaggcgagca gtacgatgtt   5640
agatggctta tttctggccg aactctcgag gatggtgctt tcgagtctgg tctcttttgac  5700 aaggactctt tccaggagac tctgtctggc tgggccaagg gtgttgttgt tggtcgagct   5760
cgtcttggcg gcattccctt cggtgtcatt ggtgtcgaga ctgcgaccgt cgacaatact   5820 accccctgccg atcccgccaa cccggactct attgagatga gcacctctga agccggccag   5880
gtttggtacc ccaactcggc cttcaagacc tctcaggcca tcaacgactt caaccatggt   5940
gaggcgcttc ctctcatgat tcttgctaac tggcgaggct tttctggtgg tcagcgagac   6000
atgtacaatg aggttctcaa gtacggatct ttcattgttg atgctctggt tgactacaag   6060
cagcccatca tggtgtacat ccctcccacc ggtgagctgc gaggtggttc ttgggttgtg   6120
gttgacccca ccatcaactc ggacatgatg gagatgtacg ctgacgtcga gtctcgaggt   6180
ggtgtgctga gcccgagggg aatggtcggt atcaagtacc gacgagacaa gctactggac   6240
accatggctc gtctggatcc cgagtactcc tctctcaaga gcagcttga ggagtctccc   6300 gattctgagg agctcaaggt caagctcagc gtgcgagaga gtctctcat gcccatctac   6360 cagcagatct ccgtgcagtt tgccgacttg catgaccgag ctggccgaat ggaggccaag   6420
ggtgtcattc gtgaggctct tgtgtggaag gatgctcgtc gattcttctt ctggcgaatc   6480
cgacgacgat tagtcgagga gtacctcatt accaagatca atagcattct gccctcttgc   6540
actcggcttg agtgtctggc tcgaatcaag tcgtggaagc ctgccactct tgatcagggc   6600
tctgaccggg tgttgccga gtggtttgac gagaactctg atgccgtctc tgctcgactc   6660
agcgagctca gaaggacgc ttctgcccag tcgtttgctt ctcaactgag aaaggaccga   6720
cagggtactc tccagggcat gaagcaggct ctcgcttctc tttctgaggc tgagcgggct   6780
gagctgctca aggggttgtg a                                              6801
```

<210> SEQ ID NO 2
<211> LENGTH: 2266
<212> TYPE: PRT
<213> ORGANISM: Yarrowia lipolytica
<220> FEATURE:
<221> NAME/KEY: MISC_FEATURE
<223> OTHER INFORMATION: biotin carboxylase

<400> SEQUENCE: 2

| | | | | | | | | | | | | | | | |
|---|---|---|---|---|---|---|---|---|---|---|---|---|---|---|---|
| Met | Arg | Leu | Gln | Leu | Arg | Thr | Leu | Thr | Arg | Arg | Phe | Phe | Ser | Met | Ala |
| 1 | | | | 5 | | | | | 10 | | | | | 15 | |
| Ser | Gly | Ser | Ser | Thr | Pro | Asp | Val | Ala | Pro | Leu | Val | Asp | Pro | Asn | Ile |
| | | | 20 | | | | | 25 | | | | | 30 | | |
| His | Lys | Gly | Leu | Ala | Ser | His | Phe | Phe | Gly | Leu | Asn | Ser | Val | His | Thr |
| | | 35 | | | | | 40 | | | | | 45 | | | |
| Ala | Lys | Pro | Ser | Lys | Val | Lys | Glu | Phe | Val | Ala | Ser | His | Gly | Gly | His |
| | 50 | | | | | 55 | | | | | 60 | | | | |
| Thr | Val | Ile | Asn | Lys | Val | Leu | Ile | Ala | Asn | Asn | Gly | Ile | Ala | Ala | Val |
| 65 | | | | | 70 | | | | | 75 | | | | | 80 |
| Lys | Glu | Ile | Arg | Ser | Val | Arg | Lys | Trp | Ala | Tyr | Glu | Thr | Phe | Gly | Asp |
| | | | | 85 | | | | | 90 | | | | | 95 | |
| Glu | Arg | Ala | Ile | Ser | Phe | Thr | Val | Met | Ala | Thr | Pro | Glu | Asp | Leu | Ala |
| | | | 100 | | | | | 105 | | | | | 110 | | |
| Ala | Asn | Ala | Asp | Tyr | Ile | Arg | Met | Ala | Asp | Gln | Tyr | Val | Glu | Val | Pro |
| | | 115 | | | | | 120 | | | | | 125 | | | |
| Gly | Gly | Thr | Asn | Asn | Asn | Asn | Tyr | Ala | Asn | Val | Glu | Leu | Ile | Val | Asp |
| | 130 | | | | | 135 | | | | | 140 | | | | |
| Val | Ala | Glu | Arg | Phe | Gly | Val | Asp | Ala | Val | Trp | Ala | Gly | Trp | Gly | His |
| 145 | | | | | 150 | | | | | 155 | | | | | 160 |
| Ala | Ser | Glu | Asn | Pro | Leu | Leu | Pro | Glu | Ser | Leu | Ala | Ala | Ser | Pro | Arg |
| | | | | 165 | | | | | 170 | | | | | 175 | |
| Lys | Ile | Val | Phe | Ile | Gly | Pro | Pro | Gly | Ala | Ala | Met | Arg | Ser | Leu | Gly |
| | | | 180 | | | | | 185 | | | | | 190 | | |
| Asp | Lys | Ile | Ser | Ser | Thr | Ile | Val | Ala | Gln | His | Ala | Lys | Val | Pro | Cys |
| | | 195 | | | | | 200 | | | | | 205 | | | |
| Ile | Pro | Trp | Ser | Gly | Thr | Gly | Val | Asp | Glu | Val | Val | Val | Asp | Lys | Ser |
| | 210 | | | | | 215 | | | | | 220 | | | | |
| Thr | Asn | Leu | Val | Ser | Val | Ser | Glu | Glu | Val | Tyr | Thr | Lys | Gly | Cys | Thr |
| 225 | | | | | 230 | | | | | 235 | | | | | 240 |
| Thr | Gly | Pro | Lys | Gln | Gly | Leu | Glu | Lys | Ala | Lys | Gln | Ile | Gly | Phe | Pro |
| | | | | 245 | | | | | 250 | | | | | 255 | |
| Val | Met | Ile | Lys | Ala | Ser | Glu | Gly | Gly | Gly | Gly | Lys | Gly | Ile | Arg | Lys |
| | | | 260 | | | | | 265 | | | | | 270 | | |
| Val | Glu | Arg | Glu | Glu | Asp | Phe | Glu | Ala | Ala | Tyr | His | Gln | Val | Glu | Gly |
| | | 275 | | | | | 280 | | | | | 285 | | | |
| Glu | Ile | Pro | Gly | Ser | Pro | Ile | Phe | Ile | Met | Gln | Leu | Ala | Gly | Asn | Ala |
| | 290 | | | | | 295 | | | | | 300 | | | | |
| Arg | His | Leu | Glu | Val | Gln | Leu | Leu | Ala | Asp | Gln | Tyr | Gly | Asn | Asn | Ile |
| 305 | | | | | 310 | | | | | 315 | | | | | 320 |
| Ser | Leu | Phe | Gly | Arg | Asp | Cys | Ser | Val | Gln | Arg | Arg | His | Gln | Lys | Ile |
| | | | | 325 | | | | | 330 | | | | | 335 | |
| Ile | Glu | Glu | Ala | Pro | Val | Thr | Val | Ala | Gly | Gln | Gln | Thr | Phe | Thr | Ala |
| | | | 340 | | | | | 345 | | | | | 350 | | |
| Met | Glu | Lys | Ala | Ala | Val | Arg | Leu | Gly | Lys | Leu | Val | Gly | Tyr | Val | Ser |
| | | 355 | | | | | 360 | | | | | 365 | | | |

```
Ala Gly Thr Val Glu Tyr Leu Tyr Ser His Glu Asp Asp Lys Phe Tyr
    370                 375                 380

Phe Leu Glu Leu Asn Pro Arg Leu Gln Val Glu His Pro Thr Thr Glu
385                 390                 395                 400

Met Val Thr Gly Val Asn Leu Pro Ala Ala Gln Leu Gln Ile Ala Met
                    405                 410                 415

Gly Ile Pro Leu Asp Arg Ile Lys Asp Ile Arg Leu Phe Tyr Gly Val
                420                 425                 430

Asn Pro His Thr Thr Thr Pro Ile Asp Phe Asp Phe Ser Gly Glu Asp
                435                 440                 445

Ala Asp Lys Thr Gln Arg Arg Pro Val Pro Arg Gly His Thr Thr Ala
450                 455                 460

Cys Arg Ile Thr Ser Glu Asp Pro Gly Glu Gly Phe Lys Pro Ser Gly
465                 470                 475                 480

Gly Thr Met His Glu Leu Asn Phe Arg Ser Ser Asn Val Trp Gly
                485                 490                 495

Tyr Phe Ser Val Gly Asn Gln Gly Gly Ile His Ser Phe Ser Asp Ser
                500                 505                 510

Gln Phe Gly His Ile Phe Ala Phe Gly Glu Asn Arg Ser Ala Ser Arg
                515                 520                 525

Lys His Met Val Val Ala Leu Lys Glu Leu Ser Ile Arg Gly Asp Phe
                530                 535                 540

Arg Thr Thr Val Glu Tyr Leu Ile Lys Leu Leu Glu Thr Pro Asp Phe
545                 550                 555                 560

Glu Asp Asn Thr Ile Thr Thr Gly Trp Leu Asp Glu Leu Ile Ser Asn
                    565                 570                 575

Lys Leu Thr Ala Glu Arg Pro Asp Ser Phe Leu Ala Val Val Cys Gly
                580                 585                 590

Ala Ala Thr Lys Ala His Arg Ala Ser Glu Asp Ser Ile Ala Thr Tyr
                595                 600                 605

Met Ala Ser Leu Glu Lys Gly Gln Val Pro Ala Arg Asp Ile Leu Lys
                610                 615                 620

Thr Leu Phe Pro Val Asp Phe Ile Tyr Glu Gly Gln Arg Tyr Lys Phe
625                 630                 635                 640

Thr Ala Thr Arg Ser Ser Glu Asp Ser Tyr Thr Leu Phe Ile Asn Gly
                    645                 650                 655

Ser Arg Cys Asp Ile Gly Val Arg Pro Leu Ser Asp Gly Gly Ile Leu
                660                 665                 670

Cys Leu Val Gly Gly Arg Ser His Asn Val Tyr Trp Lys Glu Val
                675                 680                 685

Gly Ala Thr Arg Leu Ser Val Asp Ser Lys Thr Cys Leu Leu Glu Val
                690                 695                 700

Glu Asn Asp Pro Thr Gln Leu Arg Ser Pro Ser Pro Gly Lys Leu Val
705                 710                 715                 720

Lys Phe Leu Val Glu Asn Gly Asp His Val Arg Ala Asn Gln Pro Tyr
                    725                 730                 735

Ala Glu Ile Glu Val Met Lys Met Tyr Met Thr Leu Thr Ala Gln Glu
                740                 745                 750

Asp Gly Ile Val Gln Leu Met Lys Gln Pro Gly Ser Thr Ile Glu Ala
                755                 760                 765

Gly Asp Ile Leu Gly Ile Leu Ala Leu Asp Asp Pro Ser Lys Val Lys
770                 775                 780
```

```
His Ala Lys Pro Phe Glu Gly Gln Leu Pro Glu Leu Gly Pro Pro Thr
785                 790                 795                 800

Leu Ser Gly Asn Lys Pro His Gln Arg Tyr Glu His Cys Gln Asn Val
            805                 810                 815

Leu His Asn Ile Leu Leu Gly Phe Asp Asn Gln Val Val Met Lys Ser
                820                 825                 830

Thr Leu Gln Glu Met Val Gly Leu Leu Arg Asn Pro Glu Leu Pro Tyr
        835                 840                 845

Leu Gln Trp Ala His Gln Val Ser Ser Leu His Thr Arg Met Ser Ala
    850                 855                 860

Lys Leu Asp Ala Thr Leu Ala Gly Leu Ile Asp Lys Ala Lys Gln Arg
865                 870                 875                 880

Gly Gly Glu Phe Pro Ala Lys Gln Leu Arg Ala Leu Glu Lys Glu
                885                 890                 895

Ala Ser Ser Gly Glu Val Asp Ala Leu Phe Gln Gln Thr Leu Ala Pro
            900                 905                 910

Leu Phe Asp Leu Ala Arg Glu Tyr Gln Asp Gly Leu Ala Ile His Glu
        915                 920                 925

Leu Gln Val Ala Ala Gly Leu Leu Gln Ala Tyr Tyr Asp Ser Glu Ala
    930                 935                 940

Arg Phe Cys Gly Pro Asn Val Arg Asp Glu Asp Val Ile Leu Lys Leu
945                 950                 955                 960

Arg Glu Glu Asn Arg Asp Ser Leu Arg Lys Val Val Met Ala Gln Leu
                965                 970                 975

Ser His Ser Arg Val Gly Ala Lys Asn Asn Leu Val Leu Ala Leu Leu
            980                 985                 990

Asp Glu Tyr Lys Val Ala Asp Gln Ala Gly Thr Asp Ser Pro Ala Ser
        995                 1000                1005

Asn Val His Val Ala Lys Tyr Leu Arg Pro Val Leu Arg Lys Ile
    1010                1015                1020

Val Glu Leu Glu Ser Arg Ala Ser Ala Lys Val Ser Leu Lys Ala
    1025                1030                1035

Arg Glu Ile Leu Ile Gln Cys Ala Leu Pro Ser Leu Lys Glu Arg
    1040                1045                1050

Thr Asp Gln Leu Glu His Ile Leu Arg Ser Ser Val Val Glu Ser
    1055                1060                1065

Arg Tyr Gly Glu Val Gly Leu Glu His Arg Thr Pro Arg Ala Asp
    1070                1075                1080

Ile Leu Lys Glu Val Val Asp Ser Lys Tyr Ile Val Phe Asp Val
    1085                1090                1095

Leu Ala Gln Phe Phe Ala His Asp Asp Pro Trp Ile Val Leu Ala
    1100                1105                1110

Ala Leu Glu Leu Tyr Ile Arg Arg Ala Cys Lys Ala Tyr Ser Ile
    1115                1120                1125

Leu Asp Ile Asn Tyr His Gln Asp Ser Asp Leu Pro Pro Val Ile
    1130                1135                1140

Ser Trp Arg Phe Arg Leu Pro Thr Met Ser Ser Ala Leu Tyr Asn
    1145                1150                1155

Ser Val Val Ser Ser Gly Ser Lys Thr Pro Thr Ser Pro Ser Val
    1160                1165                1170

Ser Arg Ala Asp Ser Val Ser Asp Phe Ser Tyr Thr Val Glu Arg
    1175                1180                1185

Asp Ser Ala Pro Ala Arg Thr Gly Ala Ile Val Ala Val Pro His
```

```
                1190                1195                1200
Leu Asp  Asp Leu Glu Asp  Ala Leu Thr Arg  Val Leu Glu Asn  Leu
    1205                 1210                1215

Pro Lys  Arg Gly Ala Gly  Leu Ala Ile Ser  Val Gly Ala Ser  Asn
    1220                 1225                1230

Lys Ser  Ala Ala Ala Ser  Ala Arg Asp Ala  Ala Ala Ala Ala  Ala
    1235                 1240                1245

Ser Ser  Val Asp Thr Gly  Leu Ser Asn Ile  Cys Asn Val Met  Ile
    1250                 1255                1260

Gly Arg  Val Asp Glu Ser  Asp Asp Asp Thr  Leu Ile Ala Arg
    1265                 1270                1275

Ile Ser  Gln Val Ile Glu  Asp Phe Lys Glu  Asp Phe Glu Ala  Cys
    1280                 1285                1290

Ser Leu  Arg Arg Ile Thr  Phe Ser Phe Gly  Asn Ser Arg Gly  Thr
    1295                 1300                1305

Tyr Pro  Lys Tyr Phe Thr  Phe Arg Gly Pro  Ala Tyr Glu Glu  Asp
    1310                 1315                1320

Pro Thr  Ile Arg His Ile  Glu Pro Ala Leu  Ala Phe Gln Leu  Glu
    1325                 1330                1335

Leu Ala  Arg Leu Ser Asn  Phe Asp Ile Lys  Pro Val His Thr  Asp
    1340                 1345                1350

Asn Arg  Asn Ile His Val  Tyr Glu Ala Thr  Gly Lys Asn Ala  Ala
    1355                 1360                1365

Ser Asp  Lys Arg Phe Phe  Thr Arg Gly Ile  Val Arg Pro Gly  Arg
    1370                 1375                1380

Leu Arg  Glu Asn Ile Pro  Thr Ser Glu Tyr  Leu Ile Ser Glu  Ala
    1385                 1390                1395

Asp Arg  Leu Met Ser Asp  Ile Leu Asp Ala  Leu Glu Val Ile  Gly
    1400                 1405                1410

Thr Thr  Asn Ser Asp Leu  Asn His Ile Phe  Ile Asn Phe Ser  Ala
    1415                 1420                1425

Val Phe  Ala Leu Lys Pro  Glu Glu Val Glu  Ala Ala Phe Gly  Gly
    1430                 1435                1440

Phe Leu  Glu Arg Phe Gly  Arg Arg Leu Trp  Arg Leu Arg Val  Thr
    1445                 1450                1455

Gly Ala  Glu Ile Arg Met  Met Val Ser Asp  Pro Glu Thr Gly  Ser
    1460                 1465                1470

Ala Phe  Pro Leu Arg Ala  Met Ile Asn Asn  Val Ser Gly Tyr  Val
    1475                 1480                1485

Val Gln  Ser Glu Leu Tyr  Ala Glu Ala Lys  Asn Asp Lys Gly  Gln
    1490                 1495                1500

Trp Ile  Phe Lys Ser Leu  Gly Lys Pro Gly  Ser Met His Met  Arg
    1505                 1510                1515

Ser Ile  Asn Thr Pro Tyr  Pro Thr Lys Glu  Trp Leu Gln Pro  Lys
    1520                 1525                1530

Arg Tyr  Lys Ala His Leu  Met Gly Thr Thr  Tyr Cys Tyr Asp  Phe
    1535                 1540                1545

Pro Glu  Leu Phe Arg Gln  Ser Ile Glu Ser  Asp Trp Lys Lys  Tyr
    1550                 1555                1560

Asp Gly  Lys Ala Pro Asp  Asp Leu Met Thr  Cys Asn Glu Leu  Ile
    1565                 1570                1575

Leu Asp  Glu Asp Ser Gly  Glu Leu Gln Glu  Val Asn Arg Glu  Pro
    1580                 1585                1590
```

-continued

```
Gly Ala Asn Asn Val Gly Met Val Ala Trp Lys Phe Glu Ala Lys
1595                1600                1605

Thr Pro Glu Tyr Pro Arg Gly Arg Ser Phe Ile Val Val Ala Asn
1610                1615                1620

Asp Ile Thr Phe Gln Ile Gly Ser Phe Gly Pro Ala Glu Asp Gln
1625                1630                1635

Phe Phe Phe Lys Val Thr Glu Leu Ala Arg Lys Leu Gly Ile Pro
1640                1645                1650

Arg Ile Tyr Leu Ser Ala Asn Ser Gly Ala Arg Ile Gly Ile Ala
1655                1660                1665

Asp Glu Leu Val Gly Lys Tyr Lys Val Ala Trp Asn Asp Glu Thr
1670                1675                1680

Asp Pro Ser Lys Gly Phe Lys Tyr Leu Tyr Phe Thr Pro Glu Ser
1685                1690                1695

Leu Ala Thr Leu Lys Pro Asp Thr Val Val Thr Thr Glu Ile Glu
1700                1705                1710

Glu Glu Gly Pro Asn Gly Val Glu Lys Arg His Val Ile Asp Tyr
1715                1720                1725

Ile Val Gly Glu Lys Asp Gly Leu Gly Val Glu Cys Leu Arg Gly
1730                1735                1740

Ser Gly Leu Ile Ala Gly Ala Thr Ser Arg Ala Tyr Lys Asp Ile
1745                1750                1755

Phe Thr Leu Thr Leu Val Thr Cys Arg Ser Val Gly Ile Gly Ala
1760                1765                1770

Tyr Leu Val Arg Leu Gly Gln Arg Ala Ile Gln Ile Glu Gly Gln
1775                1780                1785

Pro Ile Ile Leu Thr Gly Ala Pro Ala Ile Asn Lys Leu Leu Gly
1790                1795                1800

Arg Glu Val Tyr Ser Ser Asn Leu Gln Leu Gly Gly Thr Gln Ile
1805                1810                1815

Met Tyr Asn Asn Gly Val Ser His Leu Thr Ala Arg Asp Asp Leu
1820                1825                1830

Asn Gly Val His Lys Ile Met Gln Trp Leu Ser Tyr Ile Pro Ala
1835                1840                1845

Ser Arg Gly Leu Pro Val Pro Val Leu Pro His Lys Thr Asp Val
1850                1855                1860

Trp Asp Arg Asp Val Thr Phe Gln Pro Val Arg Gly Glu Gln Tyr
1865                1870                1875

Asp Val Arg Trp Leu Ile Ser Gly Arg Thr Leu Glu Asp Gly Ala
1880                1885                1890

Phe Glu Ser Gly Leu Phe Asp Lys Asp Ser Phe Gln Glu Thr Leu
1895                1900                1905

Ser Gly Trp Ala Lys Gly Val Val Val Gly Arg Ala Arg Leu Gly
1910                1915                1920

Gly Ile Pro Phe Gly Val Ile Gly Val Glu Thr Ala Thr Val Asp
1925                1930                1935

Asn Thr Thr Pro Ala Asp Pro Ala Asn Pro Asp Ser Ile Glu Met
1940                1945                1950

Ser Thr Ser Glu Ala Gly Gln Val Trp Tyr Pro Asn Ser Ala Phe
1955                1960                1965

Lys Thr Ser Gln Ala Ile Asn Asp Phe Asn His Gly Glu Ala Leu
1970                1975                1980
```

```
Pro Leu Met Ile Leu Ala Asn Trp Arg Gly Phe Ser Gly Gly Gln
    1985            1990                1995

Arg Asp Met Tyr Asn Glu Val Leu Lys Tyr Gly Ser Phe Ile Val
    2000            2005                2010

Asp Ala Leu Val Asp Tyr Lys Gln Pro Ile Met Val Tyr Ile Pro
    2015            2020                2025

Pro Thr Gly Glu Leu Arg Gly Gly Ser Trp Val Val Val Asp Pro
    2030            2035                2040

Thr Ile Asn Ser Asp Met Met Glu Met Tyr Ala Asp Val Glu Ser
    2045            2050                2055

Arg Gly Gly Val Leu Glu Pro Glu Gly Met Val Gly Ile Lys Tyr
    2060            2065                2070

Arg Arg Asp Lys Leu Leu Asp Thr Met Ala Arg Leu Asp Pro Glu
    2075            2080                2085

Tyr Ser Ser Leu Lys Lys Gln Leu Glu Glu Ser Pro Asp Ser Glu
    2090            2095                2100

Glu Leu Lys Val Lys Leu Ser Val Arg Glu Lys Ser Leu Met Pro
    2105            2110                2115

Ile Tyr Gln Gln Ile Ser Val Gln Phe Ala Asp Leu His Asp Arg
    2120            2125                2130

Ala Gly Arg Met Glu Ala Lys Gly Val Ile Arg Glu Ala Leu Val
    2135            2140                2145

Trp Lys Asp Ala Arg Arg Phe Phe Trp Arg Ile Arg Arg Arg
    2150            2155                2160

Leu Val Glu Glu Tyr Leu Ile Thr Lys Ile Asn Ser Ile Leu Pro
    2165            2170                2175

Ser Cys Thr Arg Leu Glu Cys Leu Ala Arg Ile Lys Ser Trp Lys
    2180            2185                2190

Pro Ala Thr Leu Asp Gln Gly Ser Asp Arg Gly Val Ala Glu Trp
    2195            2200                2205

Phe Asp Glu Asn Ser Asp Ala Val Ser Ala Arg Leu Ser Glu Leu
    2210            2215                2220

Lys Lys Asp Ala Ser Ala Gln Ser Phe Ala Ser Gln Leu Arg Lys
    2225            2230                2235

Asp Arg Gln Gly Thr Leu Gly Met Lys Gln Ala Leu Ala Ser
    2240            2245                2250

Leu Ser Glu Ala Glu Arg Ala Glu Leu Leu Lys Gly Leu
    2255            2260                2265

<210> SEQ ID NO 3
<211> LENGTH: 960
<212> TYPE: DNA
<213> ORGANISM: Escherichia coli
<220> FEATURE:
<221> NAME/KEY: misc_feature
<223> OTHER INFORMATION: Acetyl-CoA carboxylase carboxyl transferase
      subunit alpha

<400> SEQUENCE: 3
atgagtctga aattccttga ttttgaacag ccgattgcag agctggaagc gaaaatcgat      60
tctctgactg cggttagccg tcaggatgag aaactggata ttaacatcga tgaagaagtg     120
catcgtctgc gtgaaaaaag cgtagaactg acacgtaaaa tcttcgccga tctcggtgca     180
tggcagattg cgcaactggc acgccatcca cagcgtcctt atacccctgga ttacgttcgc    240 ctggcatttg atgaatttga cgaactggct ggcgaccgcg cgtatgcaga cgataaagct    300
```

```
atcgtcggtg gtatcgcccg tctcgatggt cgtccggtga tgatcattgg tcatcaaaaa    360
ggtcgtgaaa ccaaagaaaa aattcgccgt aactttggta tgccagcgcc agaaggttac    420
cgcaaagcac tgcgtctgat gcaaatggct gaacgcttta agatgcctat catcaccttt    480
atcgacaccc cggggggctta tcctggcgtg ggcgcagaag agcgtggtca gtctgaagcc    540
attgcacgca acctgcgtga aatgtctcgc ctcggcgtac cggtagtttg tacggttatc    600
ggtgaaggtg gttctggcgg tgcgctggcg attggcgtgg gcgataaagt gaatatgctg    660
caatacagca cctattccgt tatctcgccg gaaggttgtg cgtccattct gtggaagagc    720
gccgacaaag cgccgctggc ggctgaagcg atgggtatca ttgctccgcg tctgaaagaa    780
ctgaaactga tcgactccat catcccggaa ccactgggtg gtgctcaccg taacccggaa    840
gcgatggcgg catcgttgaa agcgcaactg ctggcggatc tggccgatct cgacgtgtta    900
agcactgaag atttaaaaaa tcgtcgttat cagcgcctga tgagctacgg ttacgcgtaa    960
```

<210> SEQ ID NO 4
<211> LENGTH: 319
<212> TYPE: PRT
<213> ORGANISM: Escherichia coli
<220> FEATURE:
<221> NAME/KEY: MISC_FEATURE
<223> OTHER INFORMATION: Acetyl-CoA carboxylase carboxyl transferase
      subunit alpha

<400> SEQUENCE: 4

```
Met Ser Leu Asn Phe Leu Asp Phe Glu Gln Pro Ile Ala Glu Leu Glu
1               5                   10                  15

Ala Lys Ile Asp Ser Leu Thr Ala Val Ser Arg Gln Asp Glu Lys Leu
            20                  25                  30

Asp Ile Asn Ile Asp Glu Glu Val His Arg Leu Arg Glu Lys Ser Val
        35                  40                  45

Glu Leu Thr Arg Lys Ile Phe Ala Asp Leu Gly Ala Trp Gln Ile Ala
    50                  55                  60

Gln Leu Ala Arg His Pro Gln Arg Pro Tyr Thr Leu Asp Tyr Val Arg
65                  70                  75                  80

Leu Ala Phe Asp Glu Phe Asp Glu Leu Ala Gly Asp Arg Ala Tyr Ala
                85                  90                  95

Asp Asp Lys Ala Ile Val Gly Gly Ile Ala Arg Leu Asp Gly Arg Pro
            100                 105                 110

Val Met Ile Ile Gly His Gln Lys Gly Arg Glu Thr Lys Glu Lys Ile
        115                 120                 125

Arg Arg Asn Phe Gly Met Pro Ala Pro Glu Gly Tyr Arg Lys Ala Leu
    130                 135                 140

Arg Leu Met Gln Met Ala Glu Arg Phe Lys Met Pro Ile Ile Thr Phe
145                 150                 155                 160

Ile Asp Thr Pro Gly Ala Tyr Pro Gly Val Gly Ala Glu Glu Arg Gly
                165                 170                 175

Gln Ser Glu Ala Ile Ala Arg Asn Leu Arg Glu Met Ser Arg Leu Gly
            180                 185                 190

Val Pro Val Val Cys Thr Val Ile Gly Glu Gly Gly Ser Gly Gly Ala
        195                 200                 205

Leu Ala Ile Gly Val Gly Asp Lys Val Asn Met Leu Gln Tyr Ser Thr
    210                 215                 220

Tyr Ser Val Ile Ser Pro Glu Gly Cys Ala Ser Ile Leu Trp Lys Ser
225                 230                 235                 240
```

Ala Asp Lys Ala Pro Leu Ala Glu Ala Met Gly Ile Ile Ala Pro
                245                 250                 255

Arg Leu Lys Glu Leu Lys Leu Ile Asp Ser Ile Ile Pro Glu Pro Leu
            260                 265                 270

Gly Gly Ala His Arg Asn Pro Glu Ala Met Ala Ala Ser Leu Lys Ala
            275                 280                 285

Gln Leu Leu Ala Asp Leu Ala Asp Leu Asp Val Leu Ser Thr Glu Asp
        290                 295                 300

Leu Lys Asn Arg Arg Tyr Gln Arg Leu Met Ser Tyr Gly Tyr Ala
305                 310                 315

<210> SEQ ID NO 5
<211> LENGTH: 471
<212> TYPE: DNA
<213> ORGANISM: Escherichia coli
<220> FEATURE:
<221> NAME/KEY: misc_feature
<223> OTHER INFORMATION: Acetyl-CoA carboxylase biotin carboxyl carrier
      protein

<400> SEQUENCE: 5
atggatattc gtaagattaa aaaactgatc gagctggttg aagaatcagg catctccgaa      60
ctggaaattt ctgaaggcga agagtcagta cgcattagcc gtgcagctcc tgccgcaagt     120
ttccctgtga tgcaacaagc ttacgctgca ccaatgatgc agcagccagc tcaatctaac     180
gcagccgctc cggcgaccgt tccttccatg gaagcgccag cagcagcgga atcagtggt     240 cacatcgtac gttccccgat ggttggtact ttctaccgca ccccaagccc ggacgcaaaa     300
gcgttcatcg aagtgggtca gaaagtcaac gtgggcgata ccctgtgcat cgttgaagcc     360
atgaaaatga tgaaccagat cgaagcggac aaatccggta ccgtgaaagc aattctggtc     420
gaaagtggac aaccggtaga atttgacgag ccgctggtcg tcatcgagta a              471

<210> SEQ ID NO 6
<211> LENGTH: 156
<212> TYPE: PRT
<213> ORGANISM: Escherichia coli
<220> FEATURE:
<221> NAME/KEY: MISC_FEATURE
<223> OTHER INFORMATION: Acetyl-CoA carboxylase biotin carboxyl carrier
      protein

<400> SEQUENCE: 6

Met Asp Ile Arg Lys Ile Lys Lys Leu Ile Glu Leu Val Glu Glu Ser
1               5                   10                  15

Gly Ile Ser Glu Leu Glu Ile Ser Glu Gly Glu Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
    50                  55                  60

Ala Thr Val Pro Ser Met Glu Ala Pro Ala Ala Ala Glu Ile Ser Gly
65                  70                  75                  80

His Ile Val Arg Ser Pro Met Val Gly Thr Phe Tyr Arg Thr Pro Ser
                85                  90                  95

Pro Asp Ala Lys Ala Phe Ile Glu Val Gly Gln Lys Val Asn Val Gly
            100                 105                 110

Asp Thr Leu Cys Ile Val Glu Ala Met Lys Met Met Asn Gln Ile Glu
        115                 120                 125

```
Ala Asp Lys Ser Gly Thr Val Lys Ala Ile Leu Val Glu Ser Gly Gln
        130                 135                 140

Pro Val Glu Phe Asp Glu Pro Leu Val Val Ile Glu
145                 150                 155

<210> SEQ ID NO 7
<211> LENGTH: 1350
<212> TYPE: DNA
<213> ORGANISM: Escherichia coli
<220> FEATURE:
<221> NAME/KEY: misc_feature
<223> OTHER INFORMATION: Acetyl-CoA biotin carboxylase

<400> SEQUENCE: 7
atgctggata aaattgttat tgccaaccgc ggcgagattg cattgcgtat tcttcgtgcc      60
tgtaaagaac tgggcatcaa gactgtcgct gtgcactcca gcgcggatcg cgatctaaaa     120
cacgtattac tggcagatga acggtctgt attggccctg ctccgtcagt aaaaagttat      180
ctgaacatcc cggcaatcat cagcgccgct gaaatcaccg cgcagtagc aatccatccg      240 ggttacggct tcctctccga aacgccaac tttgccgagc aggttgaacg ctccggcttt      300
atcttcattg gcccgaaagc agaaaccatt cgcctgatgg cgacaaagt atccgcaatc      360 gcggcgatga aaaagcgggg cgtcccttgc gtaccgggtt ctgacggccc gctgggcgac      420
gatatggata aaaccgtgc cattgctaaa cgcattggtt atccggtgat tatcaaagcc      480
tccggcggcg gcggcggtcg cggtatgcgc gtagtgcgcg cgacgctga actggcacaa      540 tccatctcca tgacccgtgc ggaagcgaaa gctgctttca gcaacgatat ggtttacatg      600
gagaaatacc tggaaaatcc tcgccacgtc gagattcagg tactggctga cggtcagggc      660
aacgctatct atctggcgga acgtgactgc tccatgcaac gccgccacca gaaagtggtc      720
gaagaagcgc cagcaccggg cattaccccg gaactgcgtc gctacatcgg cgaacgttgc      780
gctaaagcgt gtgttgatat cggctatcgc ggtgcaggta ctttcgagtt cctgttcgaa      840
aacggcgagt tctatttcat cgaaatgaac accgtatc aggtagaaca cccggttaca      900
gaaatgatca ccggcgttga cctgatcaaa gaacagctgc gtatcgctgc cggtcaaccg      960
ctgtcgatca agcaagaaga agttcacgtt cgcggccatg cggtggaatg tcgtatcaac     1020
gccgaagatc cgaacaccct tcctgccaagt ccgggcaaaa tcacccgttt ccacgcacct    1080
ggcggttttg cgtacgttg ggagtctcat atctacgcgg gctacaccgt accgccgtac      1140
tatgactcaa tgatcggtaa gctgatttgc tacggtgaaa accgtgacgt ggcgattgcc     1200
cgcatgaaga atgcgctgca ggagctgatc atcgacggta tcaaaaccaa cgttgatctg     1260
cagatccgca tcatgaatga cgagaacttc agcatggtg gcactaacat ccactatctg     1320
gagaaaaaac tcggtcttca ggaaaaataa                                     1350

<210> SEQ ID NO 8
<211> LENGTH: 449
<212> TYPE: PRT
<213> ORGANISM: Escherichia coli
<220> FEATURE:
<221> NAME/KEY: MISC_FEATURE
<223> OTHER INFORMATION: Acetyl-CoA biotin carboxylase

<400> SEQUENCE: 8

Met Leu Asp Lys Ile Val Ile Ala Asn Arg Gly Glu Ile Ala Leu Arg
1               5                   10                  15

Ile Leu Arg Ala Cys Lys Glu Leu Gly Ile Lys Thr Val Ala Val His
            20                  25                  30
```

```
Ser Ser Ala Asp Arg Asp Leu Lys His Val Leu Leu Ala Asp Glu Thr
        35                  40                  45
Val Cys Ile Gly Pro Ala Pro Ser Val Lys Ser Tyr Leu Asn Ile Pro
 50                  55                  60
Ala Ile Ile Ser Ala Ala Glu Ile Thr Gly Ala Val Ala Ile His Pro
 65                  70                  75                  80
Gly Tyr Gly Phe Leu Ser Glu Asn Ala Asn Phe Ala Glu Gln Val Glu
                 85                  90                  95
Arg Ser Gly Phe Ile Phe Ile Gly Pro Lys Ala Glu Thr Ile Arg Leu
                100                 105                 110
Met Gly Asp Lys Val Ser Ala Ile Ala Ala Met Lys Lys Ala Gly Val
                115                 120                 125
Pro Cys Val Pro Gly Ser Asp Gly Pro Leu Gly Asp Asp Met Asp Lys
130                 135                 140
Asn Arg Ala Ile Ala Lys Arg Ile Gly Tyr Pro Val Ile Ile Lys Ala
145                 150                 155                 160
Ser Gly Gly Gly Gly Arg Gly Met Arg Val Val Arg Gly Asp Ala
                165                 170                 175
Glu Leu Ala Gln Ser Ile Ser Met Thr Arg Ala Glu Ala Lys Ala Ala
                180                 185                 190
Phe Ser Asn Asp Met Val Tyr Met Glu Lys Tyr Leu Glu Asn Pro Arg
                195                 200                 205
His Val Glu Ile Gln Val Leu Ala Asp Gly Gln Gly Asn Ala Ile Tyr
                210                 215                 220
Leu Ala Glu Arg Asp Cys Ser Met Gln Arg Arg His Gln Lys Val Val
225                 230                 235                 240
Glu Glu Ala Pro Ala Pro Gly Ile Thr Pro Glu Leu Arg Arg Tyr Ile
                245                 250                 255
Gly Glu Arg Cys Ala Lys Ala Cys Val Asp Ile Gly Tyr Arg Gly Ala
                260                 265                 270
Gly Thr Phe Glu Phe Leu Phe Glu Asn Gly Glu Phe Tyr Phe Ile Glu
                275                 280                 285
Met Asn Thr Arg Ile Gln Val Glu His Pro Val Thr Glu Met Ile Thr
290                 295                 300
Gly Val Asp Leu Ile Lys Glu Gln Leu Arg Ile Ala Ala Gly Gln Pro
305                 310                 315                 320
Leu Ser Ile Lys Gln Glu Glu Val His Val Arg Gly His Ala Val Glu
                325                 330                 335
Cys Arg Ile Asn Ala Glu Asp Pro Asn Thr Phe Leu Pro Ser Pro Gly
                340                 345                 350
Lys Ile Thr Arg Phe His Ala Pro Gly Gly Phe Gly Val Arg Trp Glu
                355                 360                 365
Ser His Ile Tyr Ala Gly Tyr Thr Val Pro Pro Tyr Tyr Asp Ser Met
370                 375                 380
Ile Gly Lys Leu Ile Cys Tyr Gly Glu Asn Arg Asp Val Ala Ile Ala
385                 390                 395                 400
Arg Met Lys Asn Ala Leu Gln Glu Leu Ile Ile Asp Gly Ile Lys Thr
                405                 410                 415
Asn Val Asp Leu Gln Ile Arg Ile Met Asn Asp Glu Asn Phe Gln His
                420                 425                 430
Gly Gly Thr Asn Ile His Tyr Leu Glu Lys Lys Leu Gly Leu Gln Glu
                435                 440                 445
```

Lys

<210> SEQ ID NO 9
<211> LENGTH: 915
<212> TYPE: DNA
<213> ORGANISM: Escherichia coli
<220> FEATURE:
<221> NAME/KEY: misc_feature
<223> OTHER INFORMATION: Acetyl-CoA carboxylase transferase subunit beta

<400> SEQUENCE: 9

```
atgagctgga ttgaacgaat taaaagcaac attactccca cccgcaaggc gagcattcct      60
gaagggtgt ggactaagtg tgatagctgc ggtcaggttt ataccgcgc tgagctggaa       120
cgtaatcttg aggtctgtcc gaagtgtgac catcacatgc gtatgacagc gcgtaatcgc     180
ctgcatagcc tgttagatga aggaagcctt gtggagctgg gtagcgagct tgagccgaaa     240
gatgtgctga agtttcgtga ctccaagaag tataaagacc gtctggcatc tgcgcagaaa     300
gaaaccggcg aaaagatgc gctggtggt atgaaaggca ctctgtatgg aatgccggtt       360
gtcgctgcgg cattcgagtt cgcctttatg ggcggttcaa tggggtctgt tgtgggtgca     420
cgtttcgtgc gtgccgttga gcaggcgctg aagataact gcccgctgat ctgcttctcc      480
gcctctggtg gcgcacgtat gcaggaagca ctgatgtcgc tgatgcagat ggcgaaaacc     540
tctgcggcac tggcaaaaat gcaggagcgc ggcttgccgt acatctccgt gctgaccgac    600
ccgacgatgg gcggtgtttc tgcaagtttc gccatgctgg gcgatctcaa catcgctgaa    660
ccgaaagcgt taatcggctt tgccggtccg cgtgttatcg aacagaccgt tcgcgaaaaa    720
ctgccgcctg gattccagcg cagtgaattc ctgatcgaga aggcgcgat cgacatgatc     780
gtccgtcgtc cggaaatgcg cctgaaactg gcgagcattc tggcgaagtt gatgaatctg    840
ccagcgccga atcctgaagc gccgcgtgaa ggcgtagtgg tacccccggt accggatcag    900
gaacctgagg cctga                                                      915
```

<210> SEQ ID NO 10
<211> LENGTH: 304
<212> TYPE: PRT
<213> ORGANISM: Escherichia coli
<220> FEATURE:
<221> NAME/KEY: MISC_FEATURE
<223> OTHER INFORMATION: Acetyl-CoA carboxylase transferase subunit beta

<400> SEQUENCE: 10

```
Met Ser Trp Ile Glu Arg Ile Lys Ser Asn Ile Thr Pro Thr Arg Lys
1               5                   10                  15

Ala Ser Ile Pro Glu Gly Val Trp Thr Lys Cys Asp Ser Cys Gly Gln
            20                  25                  30

Val Leu Tyr Arg Ala Glu Leu Glu Arg Asn Leu Glu Val Cys Pro Lys
        35                  40                  45

Cys Asp His His Met Arg Met Thr Ala Arg Asn Arg Leu His Ser Leu
    50                  55                  60

Leu Asp Glu Gly Ser Leu Val Glu Leu Gly Ser Glu Leu Glu Pro Lys
65                  70                  75                  80

Asp Val Leu Lys Phe Arg Asp Ser Lys Lys Tyr Lys Asp Arg Leu Ala
                85                  90                  95

Ser Ala Gln Lys Glu Thr Gly Glu Lys Asp Ala Leu Val Val Met Lys
            100                 105                 110

Gly Thr Leu Tyr Gly Met Pro Val Val Ala Ala Ala Phe Glu Phe Ala
        115                 120                 125
```

```
Phe Met Gly Gly Ser Met Gly Ser Val Val Gly Ala Arg Phe Val Arg
    130                 135                 140

Ala Val Glu Gln Ala Leu Glu Asp Asn Cys Pro Leu Ile Cys Phe Ser
145                 150                 155                 160

Ala Ser Gly Gly Ala Arg Met Gln Glu Ala Leu Met Ser Leu Met Gln
                165                 170                 175

Met Ala Lys Thr Ser Ala Ala Leu Ala Lys Met Gln Glu Arg Gly Leu
            180                 185                 190

Pro Tyr Ile Ser Val Leu Thr Asp Pro Thr Met Gly Val Ser Ala
        195                 200                 205

Ser Phe Ala Met Leu Gly Asp Leu Asn Ile Ala Glu Pro Lys Ala Leu
210                 215                 220

Ile Gly Phe Ala Gly Pro Arg Val Ile Glu Gln Thr Val Arg Glu Lys
225                 230                 235                 240

Leu Pro Pro Gly Phe Gln Arg Ser Glu Phe Leu Ile Glu Lys Gly Ala
                245                 250                 255

Ile Asp Met Ile Val Arg Arg Pro Glu Met Arg Leu Lys Leu Ala Ser
            260                 265                 270

Ile Leu Ala Lys Leu Met Asn Leu Pro Ala Pro Asn Pro Glu Ala Pro
        275                 280                 285

Arg Glu Gly Val Val Val Pro Pro Val Pro Asp Gln Glu Pro Glu Ala
    290                 295                 300
```

<210> SEQ ID NO 11
<211> LENGTH: 5553
<212> TYPE: DNA
<213> ORGANISM: Yarrowia lipolytica
<220> FEATURE:
<221> NAME/KEY: misc_feature
<223> OTHER INFORMATION: fatty acid synthase subunit alpha

<400> SEQUENCE: 11

```
atgcaccccg aagtcgaaca agaactcgcc cacgtgctcc tgacggagct gctggcctac      60
caatttgcct cgcccgtgcg atggatcgag acccaggacg tgctgttcaa gcagttcaat     120
gtcgagcgag tcgtcgaagt cggcccatcc ccaactctcg ccggcatggc ccagcgaacc     180
cttaagtcca agtacgagtc atacgacgct gctctgtctc tgcagcgaga gatcctgtgt     240
tactccaagg accagaagga catctactac cttgccgatg aggccgatga agccctgcc     300 cccgctgctg gtggtgatgc ccccgctgct cctgccgctg ccgctcctgc cgccgctgcc     360
gctcctgctg ccgctgccgc ccctctggc ccgttgcca aggttgagga cgcccccgtc      420
aaggcccagg agattctcca cgccctggtc gcccataagc tcaagaagac ccccgagcag     480
gtgcccctgt ccaaggccat caaagacctt gttggtggta agtctaccat ccagaacgag     540
attctcggtg atctcggaaa ggaatttggt gccacccctg agaagcccga ggatactccc     600
cttggcgagc tggctgagtc cttccaggcc tcctttgacg caagctcgg taagcagtct      660 tcttctctca ttgcccgact catgtcctcc aagatgcccg agggttctc tctcacctct      720 gctcgatcct acctcgacag cagatggggc ctggctgctg ccgacagga ctccgttctg     780 cttgttgctc tgatgaacga acccaagaac cgacttggct ctgaagccga ggccaaggcc     840
tacctcgacg agcagaccca gaagtatgct gcttctgccg gtcttaacct gtctgccccc     900
gctggtggtg ccgagggtgg caatggcggt ggcgccgtca ttgactccgc tgcctttgac     960
gctctcacca aggaccagcg ataccctggtc cagcagcaac tcgagttgtt tgccaactac    1020
```

-continued

```
ctgaagcagg atctgcgaca gggctccaag gtggctgctg cccagaagga ggccatggat    1080
attctgcaag ctgaactgga tctttggaac tccgagcacg cgcgaggtcta cgctgagggc   1140 atcaagcccg ccttctctgc cctgaaggcc cgtgtctacg actcgtactg gaactgggct   1200
cgacaggact cgctctccat gtactttgac attgttttcg gtcgtctctc caccgttgac   1260
cgagagatta tggctaagtg tatccacctg atgaaccgaa ccaaccacaa cctgatcgac   1320
tacatgcagt accacatgga ccacgtcccc gttcacaagg gagccaccta cgagcttgcc   1380
aagcagctcg gtctgcagct cctcgagaac tgtaaggaga ctctcaccga ggcccccgtc   1440
tacaaggatg tctcttaccc cactggaccc cagaccacca ttgatgtcaa gggtaacatt   1500
gtttacaacg aggtgccccg acccaatgtc cgaaagctcg agcagtatgt ccacgagatg   1560
gcctgtggtg gtgagctgac caaggacccc tcttttgttg gagaaggtgt ccagggcgag   1620
ctcaagaagc tgtactctca gatctctgct cttgccaaga cccagaccgg ctctaccctc   1680
gacatcgagg ctctgtactc cgacctggtc gctaagatct cccaggccga ggacgcgtcc   1740
aagcctgtcg ttgagaacaa ggctgtttct gcctccatca ctcccggcac tctcccttttt  1800 ctccacatca agaagaagac cgaacttggt gcctggaatt acgacagcga ccaccgcc    1860 acctacctcg atggtcttga ggttgctgcc cgtgatggtc tcactttcca gggcaagact   1920
gctctgatca ccggtgctgg tgctggctcc attggtgcct caatcctcca gggtctcatt   1980
tccggaggct gcaaagtcat tgtcacaacc ctcgatact cccgaaaggt gaccgagtac    2040
taccagtccc tctacaccaa gttcggtgct aagggttcca ctctgattgt tgtccccttc   2100
aaccaaggct ccaagaagga cgtggacgag ctggtgtcgt tcatctacaa cgaccccaag   2160
aacggcggtc ttggctggga tctggacttt gttgttccct tgctgctct gcccgagaac    2220 ggtattgagc tggagcacat tgactcaaag tccgagcttg cccatcgaat catgctcacc   2280
aacctcctgc gtctgcttgg taacgtcaag aagcagaaag tgcccattc ctacgagact    2340 cgaccccgccc aggtcatgct gcccctgtcg cccaaccatg gcaacttcgg ctccgatggt   2400
ctgtactccg agtccaagat ctctctcgag actctgttca accggtggca caccgagtcc   2460
tggggctctt atctcaccat tgttggtgtg gtgattggct ggacccgagg taccggtctg   2520
atgagcgcca acaacatcac cgccgagggt ctggagcagc tcggcgtccg aaccttctcc   2580
cagactgaga tggccttttc catcatgggt ctcatgacca aggacattgt gcgactggcc   2640
cagaactccc ccgtgtgggc cgatctcaac ggtggcttcc agtacattcc cgacctcaag   2700
ggagttgttg aaagatccg acgagacatt tggagacct ccgagatccg acgggctgtg    2760
gctcaggaga ctgccattga acagaaggtg gtcaacggcc cccacgccga tcttccttac   2820
cagaaggtcg aggtcaagcc ccgagccaac ctcaagtttg acttccccac cctcaaatcc   2880
tacgccgagg tcaaggagct gtctcctgct ggtgatgctc tggagggtct tctggatctc   2940
tcttccgtca ttgttgtcac tggtttcgcc gaggtcggtc cttggggtaa cgcccgaacc   3000
cgatgggaca tggaggccaa cggtgtcttc tcccttgagg tgccattga gatggcctgg    3060 atcatgggtc tgatcaagca ccacaatggt cccctgcccg gcatgcctca gtactctggc   3120
tggatcgata ccaagaccaa gcagcccgtc gatgaccgag atatcaagac caagtacgag   3180
gactacctgc ttgagcacgc cggtatccga ctcattgagc ctgagctgtt ccacggctac   3240 aacccccaaga agaagacctt cctccaggag gttattgtgg agcacgatct cgagcccttt   3300
gaggcctcca aggagtctgc tgagcaattt gctctcgagc agggcgcgaa cgttgagatc   3360
ttcgccgtcc ccgagtccga ccagtggact gtgcgacttc tcaagggcgc caagctcctc   3420
```

-continued

```
attcccaagg ccctcaagtt tgaccgactt gtggccggcc agattcccac tggatgggat    3480
gcccgacgat acggtattcc cgaggacatt tgtgaccagg ttgaccccat cactctgtac    3540
gctcttgtct ccactgttga ggctctgttg gcctccggta ttaccgaccc ctacgagttc    3600
tacaagtacg tccacgtgtc cgaggtcggt aactgttccg gttccggtat gggtggtatc    3660
accgccctgc gaggcatgtt caaggaccgg ttcatggaca agcctgttca gaacgatatt    3720
ctccaggagt ccttcatcaa caccatgtct gcctgggtca acatgttgct gctctcctct    3780
tccggtccca tcaagacccc cgttggagct tgtgccactg ctgtcgagtc tgtggacatt    3840
ggttgcgaaa ccattctgtc cggcaaggcc agaatctgtc tggtcggtgg ttacgatgat    3900
ttccaggagg agtcttctca ggagtttgca acatgaacg caacatccaa cgctgagacc    3960
gagatcactc acgccgaaac tccggccgag atgtctcgac ccatcacttc cacacgagcc    4020
ggtttcatgg aggctcaggg tgctggaacc caggtgctga tggccgccga cctcgccatc    4080
gccatgggtg tgcccatcta ctgtatcgtt ggttacgtca acactgccac cgacaagatt    4140
ggccgatctg tgcctgctcc cggtaagggt atcctgacca ctgctcgaga gcaccagact    4200
ctcaaacacg ccaaccctct cctcaacatc aagtaccgaa agcgacagct cgattctcga    4260
ctccgagaca ttaagcgatg ggctgagggc gaaatggagg ctattgacat tgagcttgac    4320
gacgtgtctg acgccgacaa ggagtccttc atccaggagc gatctgccca catccagtct    4380
cagtccgatc gaatgatccg agaggctaag aactcttggg gtaacgcctt tttcaagcag    4440
gacgcccgaa tctcccccat ccgaggagcg ctggcaacct acggtctcac cattgatgac    4500
atctccgtcg cttctttcca tggtacatcc accaaggcca acgagaagaa cgagaccacc    4560
accgtcaacg ccatgctgga gcatctcggc agaacccggg gtaaccctgt ctacggtatc    4620
ttccagaagt accttactgg tcaccccaag ggagctgctg gtgcctggat gctcaacgga    4680
gccatccaat gcctcaactc tggtatcatc cctggtaacc gaaacgccga taacgtggat    4740
gcctactttg agcagtgcca gcacgtggtg ttcccctcgc gatctctgca gaccgatggc    4800
ctcaaggctg cttccgtgac ctcctttggt ttcggtcaga agggtgccca ggccattgtc    4860
atccaccccg actacctgta cgctgccctg acaccctccg agtactccga gtacaccacc    4920
cgagtcgccc agcgatacaa gaaggcttac cgatactacc acaacgccat gccgaggag     4980 tccatgttcc aggccaagga caaggctccc tactctgctg agctggagca ggaggtctac    5040
ctggatcctc ttgtgcgagt ccaccagaac gaggacaccg agcagtactc cttcaacgcc    5100
aaggacctcg ctgcctccgc ctttgtcaag aactcccaca ggacaccgc caaggtgctt     5160 gccaacctca cctcccaggt gtccggttct ggtaagaacg ttggtgtcga cgttgaggcc    5220
atctccgcca tcaacattga taacgacacc ttccttgacc gaaacttcac cgccaacgag    5280
caggcctact gcttcaaggc cccctccccc cagtcttctt tcgctggcac ttggtctgcc    5340
aaggaggctg ttttcaagtc tctgggcgtc aagtcccagg gcgaggagc tgagctcaag     5400 tccattgaga tcactcgaga tggcaacgga gctcccgtcg tggttcttca cggagctgcc    5460
aaggacgctg ctgcttctaa gggtatctcc accgtcaagg tgtccatttc ccatgacgac    5520
tctcaggccg tggctgttgc tgttgccgag tag                                 5553
```

<210> SEQ ID NO 12
<211> LENGTH: 1850
<212> TYPE: PRT
<213> ORGANISM: Yarrowia lipolytica
<220> FEATURE:

<221> NAME/KEY: MISC_FEATURE
<223> OTHER INFORMATION: fatty acid synthase subunit alpha

<400> SEQUENCE: 12

```
Met His Pro Glu Val Glu Gln Glu Leu Ala His Val Leu Leu Thr Glu
1               5                   10                  15

Leu Leu Ala Tyr Gln Phe Ala Ser Pro Val Arg Trp Ile Glu Thr Gln
            20                  25                  30

Asp Val Leu Phe Lys Gln Phe Asn Val Glu Arg Val Glu Val Gly
        35                  40                  45

Pro Ser Pro Thr Leu Ala Gly Met Ala Gln Arg Thr Leu Lys Ser Lys
        50                  55                  60

Tyr Glu Ser Tyr Asp Ala Ala Leu Ser Leu Gln Arg Glu Ile Leu Cys
65                  70                  75                  80

Tyr Ser Lys Asp Gln Lys Asp Ile Tyr Tyr Leu Ala Asp Glu Ala Asp
                85                  90                  95

Glu Ala Pro Ala Pro Ala Ala Gly Gly Asp Ala Pro Ala Ala Pro Ala
                100                 105                 110

Ala Ala Ala Pro Ala Ala Ala Ala Ala Pro Ala Ala Ala Ala Ala Pro
            115                 120                 125

Ser Gly Pro Val Ala Lys Val Glu Asp Ala Pro Val Lys Ala Gln Glu
        130                 135                 140

Ile Leu His Ala Leu Val Ala His Lys Leu Lys Lys Thr Pro Glu Gln
145                 150                 155                 160

Val Pro Leu Ser Lys Ala Ile Lys Asp Leu Val Gly Gly Lys Ser Thr
                165                 170                 175

Ile Gln Asn Glu Ile Leu Gly Asp Leu Gly Lys Glu Phe Gly Ala Thr
                180                 185                 190

Pro Glu Lys Pro Glu Asp Thr Pro Leu Gly Glu Leu Ala Glu Ser Phe
            195                 200                 205

Gln Ala Ser Phe Asp Gly Lys Leu Gly Lys Gln Ser Ser Ser Leu Ile
        210                 215                 220

Ala Arg Leu Met Ser Ser Lys Met Pro Gly Gly Phe Ser Leu Thr Ser
225                 230                 235                 240

Ala Arg Ser Tyr Leu Asp Ser Arg Trp Gly Leu Ala Ala Gly Arg Gln
                245                 250                 255

Asp Ser Val Leu Leu Val Ala Leu Met Asn Glu Pro Lys Asn Arg Leu
            260                 265                 270

Gly Ser Glu Ala Glu Ala Lys Ala Tyr Leu Asp Glu Gln Thr Gln Lys
        275                 280                 285

Tyr Ala Ala Ser Ala Gly Leu Asn Leu Ser Pro Ala Gly Gly Ala
        290                 295                 300

Glu Gly Gly Asn Gly Gly Ala Val Ile Asp Ser Ala Ala Phe Asp
305                 310                 315                 320

Ala Leu Thr Lys Asp Gln Arg Tyr Leu Val Gln Gln Gln Leu Glu Leu
                325                 330                 335

Phe Ala Asn Tyr Leu Lys Gln Asp Leu Arg Gln Gly Ser Lys Val Ala
            340                 345                 350

Ala Ala Gln Lys Glu Ala Met Asp Ile Leu Gln Ala Glu Leu Asp Leu
        355                 360                 365

Trp Asn Ser Glu His Gly Glu Val Tyr Ala Glu Gly Ile Lys Pro Ala
        370                 375                 380

Phe Ser Ala Leu Lys Ala Arg Val Tyr Asp Ser Tyr Trp Asn Trp Ala
385                 390                 395                 400
```

```
Arg Gln Asp Ser Leu Ser Met Tyr Phe Asp Ile Val Phe Gly Arg Leu
                405                 410                 415

Ser Thr Val Asp Arg Glu Ile Met Ala Lys Cys Ile His Leu Met Asn
            420                 425                 430

Arg Thr Asn His Asn Leu Ile Asp Tyr Met Gln Tyr His Met Asp His
        435                 440                 445

Val Pro Val His Lys Gly Ala Thr Tyr Glu Leu Ala Lys Gln Leu Gly
    450                 455                 460

Leu Gln Leu Leu Glu Asn Cys Lys Glu Thr Leu Thr Glu Ala Pro Val
465                 470                 475                 480

Tyr Lys Asp Val Ser Tyr Pro Thr Gly Pro Gln Thr Thr Ile Asp Val
                485                 490                 495

Lys Gly Asn Ile Val Tyr Asn Glu Val Pro Arg Pro Asn Val Arg Lys
            500                 505                 510

Leu Glu Gln Tyr Val His Glu Met Ala Cys Gly Gly Glu Leu Thr Lys
        515                 520                 525

Asp Pro Ser Phe Val Gly Glu Gly Val Gln Gly Glu Leu Lys Lys Leu
    530                 535                 540

Tyr Ser Gln Ile Ser Ala Leu Ala Lys Thr Gln Thr Gly Ser Thr Leu
545                 550                 555                 560

Asp Ile Glu Ala Leu Tyr Ser Asp Leu Val Ala Lys Ile Ser Gln Ala
                565                 570                 575

Glu Asp Ala Ser Lys Pro Val Val Glu Asn Lys Ala Val Ser Ala Ser
            580                 585                 590

Ile Thr Pro Gly Thr Leu Pro Phe Leu His Ile Lys Lys Lys Thr Glu
        595                 600                 605

Leu Gly Ala Trp Asn Tyr Asp Ser Glu Thr Thr Ala Thr Tyr Leu Asp
    610                 615                 620

Gly Leu Glu Val Ala Ala Arg Asp Gly Leu Thr Phe Gln Gly Lys Thr
625                 630                 635                 640

Ala Leu Ile Thr Gly Ala Gly Ala Gly Ser Ile Gly Ala Ser Ile Leu
                645                 650                 655

Gln Gly Leu Ile Ser Gly Gly Cys Lys Val Ile Val Thr Thr Ser Arg
            660                 665                 670

Tyr Ser Arg Lys Val Thr Glu Tyr Tyr Gln Ser Leu Tyr Thr Lys Phe
        675                 680                 685

Gly Ala Lys Gly Ser Thr Leu Ile Val Val Pro Phe Asn Gln Gly Ser
    690                 695                 700

Lys Lys Asp Val Asp Glu Leu Val Ser Phe Ile Tyr Asn Asp Pro Lys
705                 710                 715                 720

Asn Gly Gly Leu Gly Trp Asp Leu Asp Phe Val Val Pro Phe Ala Ala
                725                 730                 735

Leu Pro Glu Asn Gly Ile Glu Leu Glu His Ile Asp Ser Lys Ser Glu
            740                 745                 750

Leu Ala His Arg Ile Met Leu Thr Asn Leu Leu Arg Leu Leu Gly Asn
        755                 760                 765

Val Lys Lys Gln Lys Val Ala His Ser Tyr Glu Thr Arg Pro Ala Gln
    770                 775                 780

Val Met Leu Pro Leu Ser Pro Asn His Gly Asn Phe Gly Ser Asp Gly
785                 790                 795                 800

Leu Tyr Ser Glu Ser Lys Ile Ser Leu Glu Thr Leu Phe Asn Arg Trp
                805                 810                 815
```

His Thr Glu Ser Trp Gly Ser Tyr Leu Thr Ile Val Gly Val Ile
                820                 825                 830

Gly Trp Thr Arg Gly Thr Gly Leu Met Ser Ala Asn Asn Ile Thr Ala
        835                 840                 845

Glu Gly Leu Glu Gln Leu Gly Val Arg Thr Phe Ser Gln Thr Glu Met
    850                 855                 860

Ala Phe Ser Ile Met Gly Leu Met Thr Lys Asp Ile Val Arg Leu Ala
865                 870                 875                 880

Gln Asn Ser Pro Val Trp Ala Asp Leu Asn Gly Gly Phe Gln Tyr Ile
                885                 890                 895

Pro Asp Leu Lys Gly Val Val Gly Lys Ile Arg Arg Asp Ile Val Glu
                900                 905                 910

Thr Ser Glu Ile Arg Arg Ala Val Ala Gln Glu Thr Ala Ile Glu Gln
                915                 920                 925

Lys Val Val Asn Gly Pro His Ala Asp Leu Pro Tyr Gln Lys Val Glu
                930                 935                 940

Val Lys Pro Arg Ala Asn Leu Lys Phe Asp Phe Pro Thr Leu Lys Ser
945                 950                 955                 960

Tyr Ala Glu Val Lys Glu Leu Ser Pro Ala Gly Asp Ala Leu Glu Gly
                965                 970                 975

Leu Leu Asp Leu Ser Ser Val Ile Val Val Thr Gly Phe Ala Glu Val
                980                 985                 990

Gly Pro Trp Gly Asn Ala Arg Thr Arg Trp Asp Met Glu Ala Asn Gly
                995                 1000                1005

Val Phe Ser Leu Glu Gly Ala Ile Glu Met Ala Trp Ile Met Gly
    1010                1015                1020

Leu Ile Lys His His Asn Gly Pro Leu Pro Gly Met Pro Gln Tyr
    1025                1030                1035

Ser Gly Trp Ile Asp Thr Lys Thr Lys Gln Pro Val Asp Asp Arg
    1040                1045                1050

Asp Ile Lys Thr Lys Tyr Glu Asp Tyr Leu Leu Glu His Ala Gly
    1055                1060                1065

Ile Arg Leu Ile Glu Pro Glu Leu Phe His Gly Tyr Asn Pro Lys
    1070                1075                1080

Lys Lys Thr Phe Leu Gln Glu Val Ile Val Glu His Asp Leu Glu
    1085                1090                1095

Pro Phe Glu Ala Ser Lys Glu Ser Ala Glu Gln Phe Ala Leu Glu
    1100                1105                1110

Gln Gly Ala Asn Val Glu Ile Phe Ala Val Pro Glu Ser Asp Gln
    1115                1120                1125

Trp Thr Val Arg Leu Leu Lys Gly Ala Lys Leu Leu Ile Pro Lys
    1130                1135                1140

Ala Leu Lys Phe Asp Arg Leu Val Ala Gly Gln Ile Pro Thr Gly
    1145                1150                1155

Trp Asp Ala Arg Arg Tyr Gly Ile Pro Glu Asp Ile Cys Asp Gln
    1160                1165                1170

Val Asp Pro Ile Thr Leu Tyr Ala Leu Val Ser Thr Val Glu Ala
    1175                1180                1185

Leu Leu Ala Ser Gly Ile Thr Asp Pro Tyr Glu Phe Tyr Lys Tyr
    1190                1195                1200

Val His Val Ser Glu Val Gly Asn Cys Ser Gly Ser Gly Met Gly
    1205                1210                1215

Gly Ile Thr Ala Leu Arg Gly Met Phe Lys Asp Arg Phe Met Asp

```
            1220                1225                1230
Lys Pro Val Gln Asn Asp Ile Leu Gln Glu Ser Phe Ile Asn Thr
    1235                1240                1245
Met Ser Ala Trp Val Asn Met Leu Leu Leu Ser Ser Ser Gly Pro
        1250                1255                1260
Ile Lys Thr Pro Val Gly Ala Cys Ala Thr Ala Val Glu Ser Val
    1265                1270                1275
Asp Ile Gly Cys Glu Thr Ile Leu Ser Gly Lys Ala Arg Ile Cys
    1280                1285                1290
Leu Val Gly Gly Tyr Asp Asp Phe Gln Glu Ser Ser Gln Glu
    1295                1300                1305
Phe Ala Asn Met Asn Ala Thr Ser Asn Ala Glu Thr Glu Ile Thr
    1310                1315                1320
His Gly Arg Thr Pro Ala Glu Met Ser Arg Pro Ile Thr Ser Thr
    1325                1330                1335
Arg Ala Gly Phe Met Glu Ala Gln Gly Ala Gly Thr Gln Val Leu
    1340                1345                1350
Met Ala Ala Asp Leu Ala Ile Ala Met Gly Val Pro Ile Tyr Cys
    1355                1360                1365
Ile Val Gly Tyr Val Asn Thr Ala Thr Asp Lys Ile Gly Arg Ser
    1370                1375                1380
Val Pro Ala Pro Gly Lys Gly Ile Leu Thr Thr Ala Arg Glu His
    1385                1390                1395
Gln Thr Leu Lys His Ala Asn Pro Leu Leu Asn Ile Lys Tyr Arg
    1400                1405                1410
Lys Arg Gln Leu Asp Ser Arg Leu Arg Asp Ile Lys Arg Trp Ala
    1415                1420                1425
Glu Gly Glu Met Glu Ala Ile Asp Ile Glu Leu Asp Asp Val Ser
    1430                1435                1440
Asp Ala Asp Lys Glu Ser Phe Ile Gln Glu Arg Ser Ala His Ile
    1445                1450                1455
Gln Ser Gln Ser Asp Arg Met Ile Arg Glu Ala Lys Asn Ser Trp
    1460                1465                1470
Gly Asn Ala Phe Phe Lys Gln Asp Ala Arg Ile Ser Pro Ile Arg
    1475                1480                1485
Gly Ala Leu Ala Thr Tyr Gly Leu Thr Ile Asp Asp Ile Ser Val
    1490                1495                1500
Ala Ser Phe His Gly Thr Ser Thr Lys Ala Asn Glu Lys Asn Glu
    1505                1510                1515
Thr Thr Thr Val Asn Ala Met Leu Glu His Leu Gly Arg Thr Arg
    1520                1525                1530
Gly Asn Pro Val Tyr Gly Ile Phe Gln Lys Tyr Leu Thr Gly His
    1535                1540                1545
Pro Lys Gly Ala Ala Gly Ala Trp Met Leu Asn Gly Ala Ile Gln
    1550                1555                1560
Cys Leu Asn Ser Gly Ile Ile Pro Gly Asn Arg Asn Ala Asp Asn
    1565                1570                1575
Val Asp Ala Tyr Phe Glu Gln Cys Gln His Val Val Phe Pro Ser
    1580                1585                1590
Arg Ser Leu Gln Thr Asp Gly Leu Lys Ala Ala Ser Val Thr Ser
    1595                1600                1605
Phe Gly Phe Gly Gln Lys Gly Ala Gln Ala Ile Val Ile His Pro
    1610                1615                1620
```

```
Asp Tyr Leu Tyr Ala Ala Leu Thr Pro Ser Glu Tyr Ser Glu Tyr
    1625                1630                1635

Thr Thr Arg Val Ala Gln Arg Tyr Lys Lys Ala Tyr Arg Tyr Tyr
    1640                1645                1650

His Asn Ala Ile Ala Glu Glu Ser Met Phe Gln Ala Lys Asp Lys
    1655                1660                1665

Ala Pro Tyr Ser Ala Glu Leu Glu Gln Glu Val Tyr Leu Asp Pro
    1670                1675                1680

Leu Val Arg Val His Gln Asn Glu Asp Thr Glu Gln Tyr Ser Phe
    1685                1690                1695

Asn Ala Lys Asp Leu Ala Ala Ser Ala Phe Val Lys Asn Ser His
    1700                1705                1710

Lys Asp Thr Ala Lys Val Leu Ala Asn Leu Thr Ser Gln Val Ser
    1715                1720                1725

Gly Ser Gly Lys Asn Val Gly Val Asp Val Glu Ala Ile Ser Ala
    1730                1735                1740

Ile Asn Ile Asp Asn Asp Thr Phe Leu Asp Arg Asn Phe Thr Ala
    1745                1750                1755

Asn Glu Gln Ala Tyr Cys Phe Lys Ala Pro Ser Pro Gln Ser Ser
    1760                1765                1770

Phe Ala Gly Thr Trp Ser Ala Lys Glu Ala Val Phe Lys Ser Leu
    1775                1780                1785

Gly Val Lys Ser Gln Gly Gly Gly Ala Glu Leu Lys Ser Ile Glu
    1790                1795                1800

Ile Thr Arg Asp Gly Asn Gly Ala Pro Val Val Val Leu His Gly
    1805                1810                1815

Ala Ala Lys Asp Ala Ala Ala Ser Lys Gly Ile Ser Thr Val Lys
    1820                1825                1830

Val Ser Ile Ser His Asp Asp Ser Gln Ala Val Ala Val Ala Val
    1835                1840                1845

Ala Glu
    1850

<210> SEQ ID NO 13
<211> LENGTH: 6261
<212> TYPE: DNA
<213> ORGANISM: Yarrowia lipolytica
<220> FEATURE:
<221> NAME/KEY: misc_feature
<223> OTHER INFORMATION: fatty acid synthase subunit beta

<400> SEQUENCE: 13
atgtacccta ccacaggtgt caacaccccc cagagcgccg cctcattaag accactggtg      60
ctatcgcacg gccaaactga gcactcgctg ctggtgccca cctctctgta catcaactgc     120
accacgctcc gagaccagtt ctacgcctct ctacctccag ccactgaaga caaggccgac     180
gatgatgagc cctcctcctc cacagagctt ctagctgcct tcctgggatt tactgccaag     240
accgtcgagg aagagcccgg accatacgac gacgttctct ctctcgtgct taacgagttt     300
gagacccggt acttgcgagg taacgacatc acgctgtgg cctcctcctt gttacaagac     360
gaggacgtgc taccaccgt tggtaagatc aagagggtga ttcgagccta ctacgccgca     420
cgaattgcct gcaacggcc catcaaggcc cactcgtcgg ctctgttccg agccgcatct     480
gaagactcgg acaacgtctc tctgtacgcc atcttcggtg ccagggaaa caccgaggac     540 tactttgagg aactgcggga gatttacgac atctaccagg ggctggtcgg cgacttcatt     600
```

```
cgggaatgtg gagcccagct tctggcgctg tctcgagatc acattgctgc tgagaaaatt    660
tataccaagg gctttgatat cgtcaagtgg ctggaacacc ccgagaccat ccccgacttt    720
gagtacctaa tttctgctcc catctctgta cccatcatcg gtgttatcca gctggcacac    780
tacgctgtca cctgtcgagt tttgggtctt aatcctggcc aggtccgaga caacctcaag    840
ggtgccactg gccattctca gggtctgatc accgcaattg ccatctctgc ctccgactcg    900
tgggacgagt tctataactc tgcctctcga attctcaaga tcttcttctt catcggtgtc    960
cgtgtccaac aggcttaccc ctccactttc ctgcctccct ccactctgga agacagtgtc   1020
aagcagggtg agggcaagcc cactcccatg ctgtccatcc gagacctgtc tctcaaccag   1080
gttcaggagt tcgtcgatgc caccaacttg catttgcccg aagataagca gatcgtcgtg   1140
tctctgatca atggtcctcg aaacgttgtc gttactggcc cccccagtc tctgtatggt    1200 ctgtgtcttg tgcttcgaaa acagaaggcc gagaccggtc tggaccaaag ccgagtgccc   1260
cacagtcagc gaaagctcaa attcacacat cgtttcctgc ccatcacctc tcctttccac   1320
tcgtacctgc tggagaagag cacggatctg atcatcaacg acctggagtc ttccggtgtg   1380
gagtttgtgt cctccgagct caaggtgcct gtttacgaca cctttgatgg ctccgtgctg   1440
tctcagctac ccaagggtat cgtcagccgt ctggtcaacc tcatcactca tctgcccgtc   1500
aagtgggaga aggccactca gtttcaggcc tcccacattg tggactttgg tccggtggc    1560 gcttctggtc ttggtctgtt gacccacaag aacaaggatg aactggagt gcgaactatt    1620 cttgctggtg tcattgacca gccctcgag ttcggcttca gcaggagct gtttgaccga    1680 caggagtcgt ccattgtttt tgctcaaaac tgggccaagg agttttctcc caagctcgtc   1740
aagatctcct ccaccaacga ggtctatgtc gacaccaaat tctctcgtct gactggccga   1800
gcccccatca tggtcgctgg tatgacccct accactgtca ccccaaaatt tgtggctgcc   1860
actatgaact ccggctacca catcgagctt ggtggtggag gctactttgc ccccggtatg   1920
atgaccaagg cccttgaaca cattgagaag aacactcctc ccggatccgg tatcaccatc   1980
aacctgatct acgtcaaccc tcgactgatt caatggggta ttcctctgat tcaggagctt   2040
cgacagaagg gtttccccat tgaaggtctc accattggtg ccggtgtgcc ctctctggag   2100
gttgctaacg agtggattca ggatctgggc gtcaagcaca tcgccttcaa gcctggatcc   2160
atcgaggcca tctcctcggt gattcgaatc gccaaggcca acccagactt tcctatcatc   2220
cttcagtgga ccggaggtcg aggaggagga catcattcgt tgaggactt ccacgctccc    2280 attctgcaga tgtactccaa gatccgacga tgcagcaaca ttgtgctgat tgccggatct   2340
ggtttcggtg cttctaccga ctcctaccca tacctcaccg gttcatggtc ccgagacttt   2400
gactaccctc ccatgccctt tgacggtatc ctggttggtt ctcgagtcat ggttgccaag   2460
gaggctttca cttctctggg agccaagcag ctcattgttg actctccggg tgttgaggat   2520
tctgagtggg agaaaaccta cgacaagccc actggtggcg tcatcaccgt tctctccgag   2580
atgggtgagc ctatccacaa gctcgccact cgaggtgtgc tcttctggca cgagatggac   2640
aagaccgtgt ctcccctgcc caagaagaag cgtctggaag tgctcaagtc caagcgagcc   2700
tacatcatca agcgtctcaa cgacgacttc agaagacttg gtttgccaa gaacgcccag    2760 ggacaggtgt gtgatctcga agacctcacc tacgcggagg tcatccagcg acttgttgac   2820
ctcatgtacg tgaagaagga aagccgatgg atcgatgtca ctctccgaaa tcttgccggc   2880
actttcattc gacgagttga ggagcgattc tccaccgaga caggtgcctc ttctgtgttg   2940
```

```
cagagctttt ccgagctgga ttccgagccc gagaaggttg tcgagcgggt gtttgagctc    3000
ttccctgcct ctactaccca gatcatcaac gctcaagaca aggaccactt cctcatgctg    3060
tgtctcaacc ccatgcagaa gcccgtgccc ttcatccctg ttctggatga caactttgag    3120
ttcttcttca agaaggactc tctgtggcag tgcgaggacc tcgcagctgt tgtggacgaa    3180
gacgttggac gaatctgtat tcttcagggt cccgttgctg tcaagcactc caagattgtc    3240
aacgagcccg tcaaggagat tctcgactcc atgcacgaag gtcacatcaa gcagctgctt    3300
gaggatggcg agtacgctgg caacatggcc aacatccccc aggtcgaatg ctttggtgga    3360
aagcctgctc agaacttcgg tgacgttgct ctcgactctg tcatggttct tgatgacctc    3420
aacaagaccg tgttcaagat tgagaccggc acctctgctc tgccttctgc tgcagattgg    3480
ttctctctgc tggccggtga caagaactct tggcgacagg tcttcctgtc cactgacacc    3540
attgtgcaga ccaccaagat gatctccaac cctctgcatc gacttctgga gcccatcgca    3600
ggtttgcagg ttgagattga gcaccctgat gagcccgaga caccgtcat ctctgctttc    3660
gagcccatca acggcaaggt caccaaggtg ctggagctgc gaaagggtgc cggagacgtc    3720
atttcgctgc agctgatcga agcgcgtggc gttgaccgag tccccgttgc tcttcctctg    3780
gaattcaagt accagcccca gattggctac gctcccattg ttgaggttat gaccgacagg    3840
aacacccgaa tcaaggagtt ctactggaag ctgtggtttg ccaggactc caagtttgag    3900
attgacaccg acatcaccga ggaaatcatt ggcgatgacg ttaccatctc tggcaaggcc    3960
attgccgact tgtccacgc tgttggcaac aagggcgagg cctttgttgg tcgatctacc    4020
tctgctggta ctgtcttcgc tcccatggac tttgccattg ttttgggctg gaaggccatt    4080
atcaaggcaa tctttccccg agcaattgat gctgacattc tgcgtctggt acatctgtcc    4140
aacggcttca agatgatgcc tggcgccgac cctctgcaga tgggtgatgt tgtttccgcc    4200
actgccaaga tcgacactgt caagaactcc gctaccggca agactgttgc tgttcgaggt    4260
cttctcaccc gagacggcaa gcctgtcatg gaggttgttt ccgaattctt ctaccgaggc    4320
gaattctccg acttccagaa cacttttgag cgacgagagg aggtacccat gcaactgacc    4380
ctcaaggacg ccaaggccgt ggccattctc tgctccaagg agtggtttga gtacaatggc    4440
gacgatacca aggacctcga gggcaagacc attgtgttcc gaaactcgtc attcatcaag    4500
tacaagaatg agaccgtctt ctcttctgtg cacaccaccg gtaaggtatt gatggagctg    4560
ccctccaagg aggtcattga gattgccact gttaactacc aggctggcga gtctcatggc    4620
aatcccgtca ttgattacct ggagcgaaat ggaaccacca ttgagcagcc tgttgagttt    4680
gagaagccca tccctctgtc caaggcagat gatcttctct ccttcaaggc tccttcttcc    4740
aacgagccct acgctggtgt gtccggtgac tacaatccca tccacgtgtc tcgagccttt    4800
gcttcctatg catcccttcc tggaaccatc acccacggta tgtactcttc tgctgctgtt    4860
cgatctctga ttgaggtctg ggctgccgag aacaatgtgt ctcgagttcg agccttctcc    4920
tgtcagttcc agggcatggt tttgcccaac gacgagattt gactcgact ggagcacgtt    4980
ggcatgatca acggtcgaaa gatcatcaag gttacctcca ccaaccggga gaccgaggct    5040
gttgttctgt ctggcgaggc tgaggtcgag cagcccatct ccacctttgt ctttactggc    5100
cagggctctc aggagcaggg catgggtatg gacctgtacg cctcttccga ggtggccaag    5160
aaggtctggg acaaggctga cgagcacttc ttgcagaact acggtttctc catcatcaag    5220
atcgttgtgg agaaccccaa ggagctggat attcattttg gaggcccaa gggtaagaag    5280
atccgagaca actatatctc tatgatgttc gagaccattg atgagaagac cggcaacctc    5340
```

```
atttccgaga agatcttcaa ggagattgac gagaccaccg actctttcac cttcaagtcc    5400
cccaccggtc tgctttctgc tacccagttc actcagcccg ctctgaccct catggagaag    5460
gcgtcctttg aggacatgaa ggctaagggt cttgtccccg tggatgcaac ctttgctggt    5520
cactcccttg gtgagtactc cgctcttgct tctcttggtg atgtcatgcc catcgagtct    5580
cttgttgatg tcgtcttcta ccgaggtatg actatgcagg ttgctgttcc ccgagatgcc    5640
cagggtcggt ccaattacgg tatgtgcgct gtcaaccccct ctcgaatctc taccaccttc    5700
aacgacgctg ctcttcggtt tgtcgttgac cacatctccg agcagaccaa gtggctgctt    5760
gagattgtca actacaacgt tgagaactct cagtacgtga ctgccggtga cctgcgagct    5820
ctcgacaccc tcaccaatgt gctcaacgtg ctcaaactcg agaagatcaa cattgacaag    5880
ctgctcgagt ctctgcctct ggagaaggtc aaggagcacc tttctgagat cgtcaccgag    5940
gtggccaaga agtccgttgc taagcctcag cccattgagc tggaacgagg ctttgccgtg    6000
atccctctca agggcatctc tgtgcctttc cactcttcgt acctgcgaaa tggtgtcaag    6060
cccttccaaa acttcctggt gaagaaggtg cccaagaacg ctgtcaaacc tgccaacctc    6120
attggcaagt acatccccaa cctcactgcc aagcccttgt agatcaccaa ggagtacttt    6180
gaagaggttt acaagctcac cggttccgag aaggtcaaga gcatcatcaa caactgggag    6240
tcttatgagt ccaagcagta a                                               6261
```

<210> SEQ ID NO 14
<211> LENGTH: 2086
<212> TYPE: PRT
<213> ORGANISM: Yarrowia lipolytica
<220> FEATURE:
<221> NAME/KEY: MISC_FEATURE
<223> OTHER INFORMATION: fatty acid synthase subunit beta

<400> SEQUENCE: 14

Met Tyr Pro Thr Thr Gly Val Asn Thr Pro Gln Ser Ala Ala Ser Leu
1               5                   10                  15

Arg Pro Leu Val Leu Ser His Gly Gln Thr Glu His Ser Leu Leu Val
            20                  25                  30

Pro Thr Ser Leu Tyr Ile Asn Cys Thr Thr Leu Arg Asp Gln Phe Tyr
        35                  40                  45

Ala Ser Leu Pro Pro Ala Thr Glu Asp Lys Ala Asp Asp Glu Pro
    50                  55                  60

Ser Ser Ser Thr Glu Leu Leu Ala Ala Phe Leu Gly Phe Thr Ala Lys
65                  70                  75                  80

Thr Val Glu Glu Glu Pro Gly Pro Tyr Asp Asp Val Leu Ser Leu Val
                85                  90                  95

Leu Asn Glu Phe Glu Thr Arg Tyr Leu Arg Gly Asn Asp Ile His Ala
            100                 105                 110

Val Ala Ser Ser Leu Leu Gln Asp Glu Asp Val Pro Thr Thr Val Gly
        115                 120                 125

Lys Ile Lys Arg Val Ile Arg Ala Tyr Tyr Ala Ala Arg Ile Ala Cys
    130                 135                 140

Asn Arg Pro Ile Lys Ala His Ser Ser Ala Leu Phe Arg Ala Ala Ser
145                 150                 155                 160

Glu Asp Ser Asp Asn Val Ser Leu Tyr Ala Ile Phe Gly Gly Gln Gly
                165                 170                 175

Asn Thr Glu Asp Tyr Phe Glu Glu Leu Arg Glu Ile Tyr Asp Ile Tyr
            180                 185                 190

```
Gln Gly Leu Val Gly Asp Phe Ile Arg Glu Cys Gly Ala Gln Leu Leu
        195                 200                 205

Ala Leu Ser Arg Asp His Ile Ala Ala Glu Lys Ile Tyr Thr Lys Gly
        210                 215                 220

Phe Asp Ile Val Lys Trp Leu Glu His Pro Glu Thr Ile Pro Asp Phe
225                 230                 235                 240

Glu Tyr Leu Ile Ser Ala Pro Ile Ser Val Pro Ile Ile Gly Val Ile
                245                 250                 255

Gln Leu Ala His Tyr Ala Val Thr Cys Arg Val Leu Gly Leu Asn Pro
                260                 265                 270

Gly Gln Val Arg Asp Asn Leu Lys Gly Ala Thr Gly His Ser Gln Gly
        275                 280                 285

Leu Ile Thr Ala Ile Ala Ile Ser Ala Ser Asp Ser Trp Asp Glu Phe
        290                 295                 300

Tyr Asn Ser Ala Ser Arg Ile Leu Lys Ile Phe Phe Phe Ile Gly Val
305                 310                 315                 320

Arg Val Gln Gln Ala Tyr Pro Ser Thr Phe Leu Pro Pro Ser Thr Leu
                325                 330                 335

Glu Asp Ser Val Lys Gln Gly Glu Gly Lys Pro Thr Pro Met Leu Ser
        340                 345                 350

Ile Arg Asp Leu Ser Leu Asn Gln Val Gln Glu Phe Val Asp Ala Thr
        355                 360                 365

Asn Leu His Leu Pro Glu Asp Lys Gln Ile Val Val Ser Leu Ile Asn
370                 375                 380

Gly Pro Arg Asn Val Val Val Thr Gly Pro Pro Gln Ser Leu Tyr Gly
385                 390                 395                 400

Leu Cys Leu Val Leu Arg Lys Gln Lys Ala Glu Thr Gly Leu Asp Gln
                405                 410                 415

Ser Arg Val Pro His Ser Gln Arg Lys Leu Lys Phe Thr His Arg Phe
        420                 425                 430

Leu Pro Ile Thr Ser Pro Phe His Ser Tyr Leu Leu Glu Lys Ser Thr
        435                 440                 445

Asp Leu Ile Ile Asn Asp Leu Glu Ser Ser Gly Val Glu Phe Val Ser
        450                 455                 460

Ser Glu Leu Lys Val Pro Val Tyr Asp Thr Phe Asp Gly Ser Val Leu
465                 470                 475                 480

Ser Gln Leu Pro Lys Gly Ile Val Ser Arg Leu Val Asn Leu Ile Thr
                485                 490                 495

His Leu Pro Val Lys Trp Glu Lys Ala Thr Gln Phe Gln Ala Ser His
        500                 505                 510

Ile Val Asp Phe Gly Pro Gly Gly Ala Ser Gly Leu Gly Leu Leu Thr
        515                 520                 525

His Lys Asn Lys Asp Gly Thr Gly Val Arg Thr Ile Leu Ala Gly Val
        530                 535                 540

Ile Asp Gln Pro Leu Glu Phe Gly Phe Lys Gln Glu Leu Phe Asp Arg
545                 550                 555                 560

Gln Glu Ser Ser Ile Val Phe Ala Gln Asn Trp Ala Lys Glu Phe Ser
                565                 570                 575

Pro Lys Leu Val Lys Ile Ser Ser Thr Asn Glu Val Tyr Val Asp Thr
        580                 585                 590

Lys Phe Ser Arg Leu Thr Gly Arg Ala Pro Ile Met Val Ala Gly Met
        595                 600                 605
```

```
Thr Pro Thr Thr Val Asn Pro Lys Phe Val Ala Ala Thr Met Asn Ser
            610             615                 620

Gly Tyr His Ile Glu Leu Gly Gly Gly Tyr Phe Ala Pro Gly Met
625                 630                 635                 640

Met Thr Lys Ala Leu Glu His Ile Glu Lys Asn Thr Pro Pro Gly Ser
                645                 650                 655

Gly Ile Thr Ile Asn Leu Ile Tyr Val Asn Pro Arg Leu Ile Gln Trp
            660                 665                 670

Gly Ile Pro Leu Ile Gln Glu Leu Arg Gln Lys Gly Phe Pro Ile Glu
            675                 680                 685

Gly Leu Thr Ile Gly Ala Gly Val Pro Ser Leu Glu Val Ala Asn Glu
            690                 695                 700

Trp Ile Gln Asp Leu Gly Val Lys His Ile Ala Phe Lys Pro Gly Ser
705                 710                 715                 720

Ile Glu Ala Ile Ser Ser Val Ile Arg Ile Ala Lys Ala Asn Pro Asp
                725                 730                 735

Phe Pro Ile Ile Leu Gln Trp Thr Gly Arg Gly Gly His His
            740                 745                 750

Ser Phe Glu Asp Phe His Ala Pro Ile Leu Gln Met Tyr Ser Lys Ile
            755                 760                 765

Arg Arg Cys Ser Asn Ile Val Leu Ile Ala Gly Ser Gly Phe Gly Ala
770                 775                 780

Ser Thr Asp Ser Tyr Pro Tyr Leu Thr Gly Ser Trp Ser Arg Asp Phe
785                 790                 795                 800

Asp Tyr Pro Pro Met Pro Phe Asp Gly Ile Leu Val Gly Ser Arg Val
                805                 810                 815

Met Val Ala Lys Glu Ala Phe Thr Ser Leu Gly Ala Lys Gln Leu Ile
                820                 825                 830

Val Asp Ser Pro Gly Val Glu Asp Ser Glu Trp Glu Lys Thr Tyr Asp
            835                 840                 845

Lys Pro Thr Gly Gly Val Ile Thr Val Leu Ser Glu Met Gly Glu Pro
            850                 855                 860

Ile His Lys Leu Ala Thr Arg Gly Val Leu Phe Trp His Glu Met Asp
865                 870                 875                 880

Lys Thr Val Phe Ser Leu Pro Lys Lys Arg Leu Glu Val Leu Lys
                885                 890                 895

Ser Lys Arg Ala Tyr Ile Ile Lys Arg Leu Asn Asp Asp Phe Gln Lys
            900                 905                 910

Thr Trp Phe Ala Lys Asn Ala Gln Gly Gln Val Cys Asp Leu Glu Asp
            915                 920                 925

Leu Thr Tyr Ala Glu Val Ile Gln Arg Leu Val Asp Leu Met Tyr Val
            930                 935                 940

Lys Lys Glu Ser Arg Trp Ile Asp Val Thr Leu Arg Asn Leu Ala Gly
945                 950                 955                 960

Thr Phe Ile Arg Arg Val Glu Glu Arg Phe Ser Glu Thr Gly Ala
                965                 970                 975

Ser Ser Val Leu Gln Ser Phe Ser Glu Leu Asp Ser Glu Pro Glu Lys
            980                 985                 990

Val Val Glu Arg Val Phe Glu Leu Phe Pro Ala Ser Thr Thr Gln Ile
            995                 1000                1005

Ile Asn Ala Gln Asp Lys Asp His Phe Leu Met Leu Cys Leu Asn
            1010                1015                1020

Pro Met Gln Lys Pro Val Pro Phe Ile Pro Val Leu Asp Asp Asn
```

-continued

```
                1025                1030                1035
Phe Glu Phe Phe Phe Lys Lys Asp Ser Leu Trp Gln Cys Glu Asp
        1040                1045                1050
Leu Ala Ala Val Val Asp Glu Asp Val Gly Arg Ile Cys Ile Leu
        1055                1060                1065
Gln Gly Pro Val Ala Val Lys His Ser Lys Ile Val Asn Glu Pro
        1070                1075                1080
Val Lys Glu Ile Leu Asp Ser Met His Glu Gly His Ile Lys Gln
        1085                1090                1095
Leu Leu Glu Asp Gly Glu Tyr Ala Gly Asn Met Ala Asn Ile Pro
        1100                1105                1110
Gln Val Glu Cys Phe Gly Gly Lys Pro Ala Gln Asn Phe Gly Asp
        1115                1120                1125
Val Ala Leu Asp Ser Val Met Val Leu Asp Leu Asn Lys Thr
        1130                1135                1140
Val Phe Lys Ile Glu Thr Gly Thr Ser Ala Leu Pro Ser Ala Ala
        1145                1150                1155
Asp Trp Phe Ser Leu Leu Ala Gly Asp Lys Asn Ser Trp Arg Gln
        1160                1165                1170
Val Phe Leu Ser Thr Asp Thr Ile Val Gln Thr Thr Lys Met Ile
        1175                1180                1185
Ser Asn Pro Leu His Arg Leu Leu Glu Pro Ile Ala Gly Leu Gln
        1190                1195                1200
Val Glu Ile Glu His Pro Asp Glu Pro Glu Asn Thr Val Ile Ser
        1205                1210                1215
Ala Phe Glu Pro Ile Asn Gly Lys Val Thr Lys Val Leu Glu Leu
        1220                1225                1230
Arg Lys Gly Ala Gly Asp Val Ile Ser Leu Gln Leu Ile Glu Ala
        1235                1240                1245
Arg Gly Val Asp Arg Val Pro Val Ala Leu Pro Leu Glu Phe Lys
        1250                1255                1260
Tyr Gln Pro Gln Ile Gly Tyr Ala Pro Ile Val Glu Val Met Thr
        1265                1270                1275
Asp Arg Asn Thr Arg Ile Lys Glu Phe Tyr Trp Lys Leu Trp Phe
        1280                1285                1290
Gly Gln Asp Ser Lys Phe Glu Ile Asp Thr Asp Ile Thr Glu Glu
        1295                1300                1305
Ile Ile Gly Asp Asp Val Thr Ile Ser Gly Lys Ala Ile Ala Asp
        1310                1315                1320
Phe Val His Ala Val Gly Asn Lys Gly Glu Ala Phe Val Gly Arg
        1325                1330                1335
Ser Thr Ser Ala Gly Thr Val Phe Ala Pro Met Asp Phe Ala Ile
        1340                1345                1350
Val Leu Gly Trp Lys Ala Ile Ile Lys Ala Ile Phe Pro Arg Ala
        1355                1360                1365
Ile Asp Ala Asp Ile Leu Arg Leu Val His Leu Ser Asn Gly Phe
        1370                1375                1380
Lys Met Met Pro Gly Ala Asp Pro Leu Gln Met Gly Asp Val Val
        1385                1390                1395
Ser Ala Thr Ala Lys Ile Asp Thr Val Lys Asn Ser Ala Thr Gly
        1400                1405                1410
Lys Thr Val Ala Val Arg Gly Leu Leu Thr Arg Asp Gly Lys Pro
        1415                1420                1425
```

-continued

Val Met Glu Val Val Ser Glu Phe Phe Tyr Arg Gly Glu Phe Ser
    1430            1435            1440

Asp Phe Gln Asn Thr Phe Glu Arg Arg Glu Glu Val Pro Met Gln
    1445            1450            1455

Leu Thr Leu Lys Asp Ala Lys Ala Val Ala Ile Leu Cys Ser Lys
    1460            1465            1470

Glu Trp Phe Glu Tyr Asn Gly Asp Asp Thr Lys Asp Leu Glu Gly
    1475            1480            1485

Lys Thr Ile Val Phe Arg Asn Ser Ser Phe Ile Lys Tyr Lys Asn
    1490            1495            1500

Glu Thr Val Phe Ser Ser Val His Thr Thr Gly Lys Val Leu Met
    1505            1510            1515

Glu Leu Pro Ser Lys Glu Val Ile Glu Ile Ala Thr Val Asn Tyr
    1520            1525            1530

Gln Ala Gly Glu Ser His Gly Asn Pro Val Ile Asp Tyr Leu Glu
    1535            1540            1545

Arg Asn Gly Thr Thr Ile Glu Gln Pro Val Glu Phe Glu Lys Pro
    1550            1555            1560

Ile Pro Leu Ser Lys Ala Asp Asp Leu Leu Ser Phe Lys Ala Pro
    1565            1570            1575

Ser Ser Asn Glu Pro Tyr Ala Gly Val Ser Gly Asp Tyr Asn Pro
    1580            1585            1590

Ile His Val Ser Arg Ala Phe Ala Ser Tyr Ala Ser Leu Pro Gly
    1595            1600            1605

Thr Ile Thr His Gly Met Tyr Ser Ser Ala Ala Val Arg Ser Leu
    1610            1615            1620

Ile Glu Val Trp Ala Ala Glu Asn Asn Val Ser Arg Val Arg Ala
    1625            1630            1635

Phe Ser Cys Gln Phe Gln Gly Met Val Leu Pro Asn Asp Glu Ile
    1640            1645            1650

Val Thr Arg Leu Glu His Val Gly Met Ile Asn Gly Arg Lys Ile
    1655            1660            1665

Ile Lys Val Thr Ser Thr Asn Arg Glu Thr Glu Ala Val Val Leu
    1670            1675            1680

Ser Gly Glu Ala Glu Val Glu Gln Pro Ile Ser Thr Phe Val Phe
    1685            1690            1695

Thr Gly Gln Gly Ser Gln Glu Gln Gly Met Gly Met Asp Leu Tyr
    1700            1705            1710

Ala Ser Ser Glu Val Ala Lys Lys Val Trp Asp Lys Ala Asp Glu
    1715            1720            1725

His Phe Leu Gln Asn Tyr Gly Phe Ser Ile Ile Lys Ile Val Val
    1730            1735            1740

Glu Asn Pro Lys Glu Leu Asp Ile His Phe Gly Gly Pro Lys Gly
    1745            1750            1755

Lys Lys Ile Arg Asp Asn Tyr Ile Ser Met Met Phe Glu Thr Ile
    1760            1765            1770

Asp Glu Lys Thr Gly Asn Leu Ile Ser Glu Lys Ile Phe Lys Glu
    1775            1780            1785

Ile Asp Glu Thr Thr Asp Ser Phe Thr Phe Lys Ser Pro Thr Gly
    1790            1795            1800

Leu Leu Ser Ala Thr Gln Phe Thr Gln Pro Ala Leu Thr Leu Met
    1805            1810            1815

```
Glu Lys Ala Ser Phe Glu Asp Met Lys Ala Lys Gly Leu Val Pro
1820                1825                1830

Val Asp Ala Thr Phe Ala Gly His Ser Leu Gly Glu Tyr Ser Ala
1835                1840                1845

Leu Ala Ser Leu Gly Asp Val Met Pro Ile Glu Ser Leu Val Asp
1850                1855                1860

Val Val Phe Tyr Arg Gly Met Thr Met Gln Val Ala Val Pro Arg
1865                1870                1875

Asp Ala Gln Gly Arg Ser Asn Tyr Gly Met Cys Ala Val Asn Pro
1880                1885                1890

Ser Arg Ile Ser Thr Thr Phe Asn Asp Ala Ala Leu Arg Phe Val
1895                1900                1905

Val Asp His Ile Ser Glu Gln Thr Lys Trp Leu Leu Glu Ile Val
1910                1915                1920

Asn Tyr Asn Val Glu Asn Ser Gln Tyr Val Thr Ala Gly Asp Leu
1925                1930                1935

Arg Ala Leu Asp Thr Leu Thr Asn Val Leu Asn Val Leu Lys Leu
1940                1945                1950

Glu Lys Ile Asn Ile Asp Lys Leu Leu Glu Ser Leu Pro Leu Glu
1955                1960                1965

Lys Val Lys Glu His Leu Ser Glu Ile Val Thr Glu Val Ala Lys
1970                1975                1980

Lys Ser Val Ala Lys Pro Gln Pro Ile Glu Leu Glu Arg Gly Phe
1985                1990                1995

Ala Val Ile Pro Leu Lys Gly Ile Ser Val Pro Phe His Ser Ser
2000                2005                2010

Tyr Leu Arg Asn Gly Val Lys Pro Phe Gln Asn Phe Leu Val Lys
2015                2020                2025

Lys Val Pro Lys Asn Ala Val Lys Pro Ala Asn Leu Ile Gly Lys
2030                2035                2040

Tyr Ile Pro Asn Leu Thr Ala Lys Pro Phe Glu Ile Thr Lys Glu
2045                2050                2055

Tyr Phe Glu Glu Val Tyr Lys Leu Thr Gly Ser Glu Lys Val Lys
2060                2065                2070

Ser Ile Ile Asn Asn Trp Glu Ser Tyr Glu Ser Lys Gln
2075                2080                2085

<210> SEQ ID NO 15
<211> LENGTH: 1635
<212> TYPE: DNA
<213> ORGANISM: Yarrowia lipolytica
<220> FEATURE:
<221> NAME/KEY: misc_feature
<223> OTHER INFORMATION: Acetyl-CoA carboxylase transferase subunit beta

<400> SEQUENCE: 15
atgcccgagt accctcgagg ccgatctttc atcgtggtgg ccaacgatat caccttccag      60
attggttcgt ttggccctgc tgaggaccag ttcttcttca aggtgacgga gctggctcga     120
aagctcggta ttcctcgaat ctatctgtct gccaactctg gtgctcgaat cggcattgct     180
gacgagctcg ttggcaagta caaggttgcg tggaacgacg agactgaccc ctccaagggc     240
ttcaagtacc tttacttcac ccctgagtct cttgccaccc tcaagcccga cactgttgtc     300
accactgaga ttgaggagga gggtcccaac ggcgtggaga agcgtcatgt gatcgactac     360
attgtcggag agaaggacgg tctcggagtc gagtgtctgc ggggctctgg tctcattgca     420
```

```
ggcgccactt ctcgagccta caaggatatc ttcactctca ctcttgtcac ctgtcgatcc      480
gttggtatcg gtgcttacct tgttcgtctt ggtcaacgag ccatccagat tgagggccag      540
cccatcattc tcactggtgc ccccgccatc aacaagctgc ttggtcgaga ggtctactct      600
tccaacttgc agcttggtgg tactcagatc atgtacaaca cggtgtgtc tcatctgact       660
gcccgagatg atctcaacgg tgtccacaag atcatgcagt ggctgtcata catccctgct      720
tctcgaggtc ttccagtgcc tgttctccct cacaagaccg atgtgtggga tcgagacgtg      780
acgttccagc ctgtccgagg cgagcagtac gatgttagat ggcttatttc tggccgaact      840
ctcgaggatg tgctttcga gtctggtctc tttgacaagg actctttcca ggagactctg       900
tctggctggg ccaagggtgt tgttgttggt cgagctcgtc ttggcggcat tcccttcggt      960
gtcattggtg tcgagactgc gaccgtcgac aatactaccc ctgccgatcc cgccaacccg     1020
gactctattg agatgagcac ctctgaagcc ggccaggttt ggtaccccaa ctcggccttc     1080
aagacctctc aggccatcaa cgacttcaac catggtgagg cgcttcctct catgattctt     1140
gctaactggc gaggcttttc tggtggtcag cgagacatgt acaatgaggt tctcaagtac     1200
ggatctttca ttgttgatgc tctggttgac tacaagcagc ccatcatggt gtacatccct     1260
cccaccggtg agctgcgagg tggttcttgg gttgtgttg accccaccat caactcggac      1320
atgatggaga tgtacgctga cgtcgagtct cgaggtggtg tgctggagcc cgagggaatg     1380
gtcggtatca agtaccgacg agacaagcta ctggacacca tggctcgtct ggatcccgag     1440
tactcctctc tcaagaagca gcttgaggag tctcccgatt ctgaggagct caaggtcaag     1500
ctcagcgtgc gagagaagtc tctcatgccc atctaccagc agatctccgt gcagtttgcc     1560
gacttgcatg accgagctgg ccgaatggag gccaagggtg tcattcgtga ggctcttgtg     1620
tggaaggatg cttga                                                      1635

<210> SEQ ID NO 16
<211> LENGTH: 544
<212> TYPE: PRT
<213> ORGANISM: Yarrowia lipolytica
<220> FEATURE:
<221> NAME/KEY: MISC_FEATURE
<223> OTHER INFORMATION: Acetyl-CoA carboxylase transferase subunit beta

<400> SEQUENCE: 16

Met Pro Glu Tyr Pro Arg Gly Arg Ser Phe Ile Val Val Ala Asn Asp
1               5                   10                  15

Ile Thr Phe Gln Ile Gly Ser Phe Gly Pro Ala Glu Asp Gln Phe Phe
            20                  25                  30

Phe Lys Val Thr Glu Leu Ala Arg Lys Leu Gly Ile Pro Arg Ile Tyr
        35                  40                  45

Leu Ser Ala Asn Ser Gly Ala Arg Ile Gly Ile Ala Asp Glu Leu Val
    50                  55                  60

Gly Lys Tyr Lys Val Ala Trp Asn Asp Glu Thr Asp Pro Ser Lys Gly
65                  70                  75                  80

Phe Lys Tyr Leu Tyr Phe Thr Pro Glu Ser Leu Ala Thr Leu Lys Pro
                85                  90                  95

Asp Thr Val Val Thr Thr Glu Ile Glu Glu Gly Pro Asn Gly Val
            100                 105                 110

Glu Lys Arg His Val Ile Asp Tyr Ile Val Gly Glu Lys Asp Gly Leu
        115                 120                 125

Gly Val Glu Cys Leu Arg Gly Ser Gly Leu Ile Ala Gly Ala Thr Ser
    130                 135                 140
```

Arg Ala Tyr Lys Asp Ile Phe Thr Leu Thr Leu Val Thr Cys Arg Ser
145                 150                 155                 160

Val Gly Ile Gly Ala Tyr Leu Val Arg Leu Gly Gln Arg Ala Ile Gln
            165                 170                 175

Ile Glu Gly Gln Pro Ile Ile Leu Thr Gly Ala Pro Ala Ile Asn Lys
            180                 185                 190

Leu Leu Gly Arg Glu Val Tyr Ser Ser Asn Leu Gln Leu Gly Gly Thr
            195                 200                 205

Gln Ile Met Tyr Asn Asn Gly Val Ser His Leu Thr Ala Arg Asp Asp
210                 215                 220

Leu Asn Gly Val His Lys Ile Met Gln Trp Leu Ser Tyr Ile Pro Ala
225                 230                 235                 240

Ser Arg Gly Leu Pro Val Pro Val Leu Pro His Lys Thr Asp Val Trp
            245                 250                 255

Asp Arg Asp Val Thr Phe Gln Pro Val Arg Gly Glu Gln Tyr Asp Val
            260                 265                 270

Arg Trp Leu Ile Ser Gly Arg Thr Leu Glu Asp Gly Ala Phe Glu Ser
            275                 280                 285

Gly Leu Phe Asp Lys Asp Ser Phe Gln Glu Thr Leu Ser Gly Trp Ala
290                 295                 300

Lys Gly Val Val Gly Arg Ala Arg Leu Gly Gly Ile Pro Phe Gly
305                 310                 315                 320

Val Ile Gly Val Glu Thr Ala Thr Val Asp Asn Thr Thr Pro Ala Asp
            325                 330                 335

Pro Ala Asn Pro Asp Ser Ile Glu Met Ser Thr Ser Glu Ala Gly Gln
            340                 345                 350

Val Trp Tyr Pro Asn Ser Ala Phe Lys Thr Ser Gln Ala Ile Asn Asp
            355                 360                 365

Phe Asn His Gly Glu Ala Leu Pro Leu Met Ile Leu Ala Asn Trp Arg
370                 375                 380

Gly Phe Ser Gly Gly Gln Arg Asp Met Tyr Asn Glu Val Leu Lys Tyr
385                 390                 395                 400

Gly Ser Phe Ile Val Asp Ala Leu Val Asp Tyr Lys Gln Pro Ile Met
            405                 410                 415

Val Tyr Ile Pro Pro Thr Gly Glu Leu Arg Gly Gly Ser Trp Val Val
            420                 425                 430

Val Asp Pro Thr Ile Asn Ser Asp Met Met Glu Met Tyr Ala Asp Val
            435                 440                 445

Glu Ser Arg Gly Gly Val Leu Glu Pro Glu Gly Met Val Gly Ile Lys
            450                 455                 460

Tyr Arg Arg Asp Lys Leu Leu Asp Thr Met Ala Arg Leu Asp Pro Glu
465                 470                 475                 480

Tyr Ser Ser Leu Lys Lys Gln Leu Glu Glu Ser Pro Asp Ser Glu Glu
            485                 490                 495

Leu Lys Val Lys Leu Ser Val Arg Glu Lys Ser Leu Met Pro Ile Tyr
            500                 505                 510

Gln Gln Ile Ser Val Gln Phe Ala Asp Leu His Asp Arg Ala Gly Arg
            515                 520                 525

Met Glu Ala Lys Gly Val Ile Arg Glu Ala Leu Val Trp Lys Asp Ala
530                 535                 540

<210> SEQ ID NO 17
<211> LENGTH: 792

```
<212> TYPE: DNA
<213> ORGANISM: Yarrowia lipolytica
<220> FEATURE:
<221> NAME/KEY: misc_feature
<223> OTHER INFORMATION: fatty acid synthase subunit alpha-active site 1

<400> SEQUENCE: 17
atggatggtc tcactttcca gggcaagact gctctgatca ccggtgctgg tgctggctcc    60
attggtgcct caatcctcca gggtctcatt tccggaggct gcaaagtcat tgtcacaacc   120
tctcgatact cccgaaaggt gaccgagtac taccagtccc tctacaccaa gttcggtgct   180
aagggttcca ctctgattgt tgtccccttc aaccaaggct ccaagaagga cgtggacgag   240
ctggtgtcgt tcatctacaa cgaccccaag aacggcggtc ttggctggga tctggacttt   300
gttgttccct tgctgctctc gcccgagaac ggtattgagc tggagcacat tgactcaaag   360
tccgagcttg cccatcgaat catgctcacc aacctcctgc gtctgcttgg taacgtcaag   420
aagcagaaag tggcccattc ctacgagact cgacccgccc aggtcatgct gcccctgtcg   480
cccaaccatg gcaacttcgg ctccgatggt ctgtactccg agtccaagat ctctctcgag   540
actctgttca accggtggca caccgagtcc tggggctctt atctcaccat tgttggtgtg   600
gtgattggct ggacccgagg taccggtctg atgagcgcca acaacatcac cgccgagggt   660
ctggagcagc tcggcgtccg aaccttctcc cagactgaga tggccttttc catcatgggt   720
ctcatgacca aggacattgt gcgactggcc cagaactccc ccgtgtgggc cgatctcaac   780
ggtggcttct ga                                                       792

<210> SEQ ID NO 18
<211> LENGTH: 263
<212> TYPE: PRT
<213> ORGANISM: Yarrowia lipolytica
<220> FEATURE:
<221> NAME/KEY: MISC_FEATURE
<223> OTHER INFORMATION: fatty acid synthase subunit alpha-active site 1

<400> SEQUENCE: 18

Met Asp Gly Leu Thr Phe Gln Gly Lys Thr Ala Leu Ile Thr Gly Ala
1               5                   10                  15

Gly Ala Gly Ser Ile Gly Ala Ser Ile Leu Gln Gly Leu Ile Ser Gly
            20                  25                  30

Gly Cys Lys Val Ile Val Thr Thr Ser Arg Tyr Ser Arg Lys Val Thr
        35                  40                  45

Glu Tyr Tyr Gln Ser Leu Tyr Thr Lys Phe Gly Ala Lys Gly Ser Thr
    50                  55                  60

Leu Ile Val Val Pro Phe Asn Gln Gly Ser Lys Lys Asp Val Asp Glu
65                  70                  75                  80

Leu Val Ser Phe Ile Tyr Asn Asp Pro Lys Asn Gly Gly Leu Gly Trp
                85                  90                  95

Asp Leu Asp Phe Val Val Pro Phe Ala Ala Leu Pro Glu Asn Gly Ile
            100                 105                 110

Glu Leu Glu His Ile Asp Ser Lys Ser Glu Leu Ala His Arg Ile Met
        115                 120                 125

Leu Thr Asn Leu Leu Arg Leu Leu Gly Asn Val Lys Lys Gln Lys Val
    130                 135                 140

Ala His Ser Tyr Glu Thr Arg Pro Ala Gln Val Met Leu Pro Leu Ser
145                 150                 155                 160

Pro Asn His Gly Asn Phe Gly Ser Asp Gly Leu Tyr Ser Glu Ser Lys
                165                 170                 175
```

Ile Ser Leu Glu Thr Leu Phe Asn Arg Trp His Thr Glu Ser Trp Gly
            180                 185                 190

Ser Tyr Leu Thr Ile Val Gly Val Ile Gly Trp Thr Arg Gly Thr
        195                 200                 205

Gly Leu Met Ser Ala Asn Asn Ile Thr Ala Glu Gly Leu Glu Gln Leu
    210                 215                 220

Gly Val Arg Thr Phe Ser Gln Thr Glu Met Ala Phe Ser Ile Met Gly
225                 230                 235                 240

Leu Met Thr Lys Asp Ile Val Arg Leu Ala Gln Asn Ser Pro Val Trp
                245                 250                 255

Ala Asp Leu Asn Gly Gly Phe
            260

<210> SEQ ID NO 19
<211> LENGTH: 903
<212> TYPE: DNA
<213> ORGANISM: Artificial sequence
<220> FEATURE:
<223> OTHER INFORMATION: Synthetic polynucleotide

<400> SEQUENCE: 19

```
atgctcgagt ggaagcctaa gcctaagctc cctcagctcc tggacgatca tttggtctg      60
cacggtctgg ttttccgacg aacttttgcc atccgatcct acgaggttgg acccgaccga    120
tctacctcga ttctggctgt catgaaccac atgcaggaag ccactctgaa ccatgctaag    180
tccgttggca tcctcggcga cggttttgga accactctgg agatgtctaa gcgagatctc    240
atgtgggtcg tgcgacgaac ccacgttgcc gtcgagcgat accctacctg gggtgacact    300
gtggaggttg agtgctggat tggcgcttct ggtaacaacg gaatgcgacg agactttctg    360
gtgcgagatt gcaagaccgg agagatcctc acccgatgta cttccctgtc tgtcctcatg    420
aacacccgaa ctcgacgact ctccaccatt cccgacgagg tgcgaggcga gatcggtcct    480
gccttcattg ataacgtcgc tgtgaaggac gatgagatca agaagctgca gaagctcaac    540
gactctaccg ccgattacat tcagggcggt ctgactcccc gatggaacga cctcgatgtg    600
aaccagcacg ttaacaacct gaagtacgtt gcttgggtct tcgagaccgt ccctgactcg    660
atctttgagt cccaccatat ttcctcttt ccctcgagt accgacgaga gtgcactcga    720
gactctgtcc tgcgatcgct caccactgtg tcgggaggct cgtctgaggc tggactggtg    780
tgtgaccatc tgctccagct ggagggtgga tctgaggttc tccgagctcg aaccgagtgg    840
cgacccaagc tgaccgattc tttccgaggc atctctgtga ttcccgctga gccccgagtt    900
tag                                                                   903
```

<210> SEQ ID NO 20
<211> LENGTH: 300
<212> TYPE: PRT
<213> ORGANISM: Umbellularia californica
<220> FEATURE:
<221> NAME/KEY: MISC_FEATURE
<223> OTHER INFORMATION: lauroyl ACP- thioesterase

<400> SEQUENCE: 20

Met Leu Glu Trp Lys Pro Lys Pro Lys Leu Pro Gln Leu Leu Asp Asp
1                   5                   10                  15

His Phe Gly Leu His Gly Leu Val Phe Arg Arg Thr Phe Ala Ile Arg
            20                  25                  30

Ser Tyr Glu Val Gly Pro Asp Arg Ser Thr Ser Ile Leu Ala Val Met

```
                35                  40                  45
Asn His Met Gln Glu Ala Thr Leu Asn His Ala Lys Ser Val Gly Ile
 50                  55                  60

Leu Gly Asp Gly Phe Gly Thr Thr Leu Glu Met Ser Lys Arg Asp Leu
65                  70                  75                  80

Met Trp Val Val Arg Thr His Val Ala Val Glu Arg Tyr Pro Thr
                85                  90                  95

Trp Gly Asp Thr Val Glu Val Cys Trp Ile Gly Ala Ser Gly Asn
                100                 105                 110

Asn Gly Met Arg Arg Asp Phe Leu Val Arg Asp Cys Lys Thr Gly Glu
                115                 120                 125

Ile Leu Thr Arg Cys Thr Ser Leu Ser Val Leu Met Asn Thr Arg Thr
    130                 135                 140

Arg Arg Leu Ser Thr Ile Pro Asp Glu Val Arg Gly Glu Ile Gly Pro
145                 150                 155                 160

Ala Phe Ile Asp Asn Val Ala Val Lys Asp Asp Glu Ile Lys Lys Leu
                165                 170                 175

Gln Lys Leu Asn Asp Ser Thr Ala Asp Tyr Ile Gln Gly Gly Leu Thr
                180                 185                 190

Pro Arg Trp Asn Asp Leu Asp Val Asn Gln His Val Asn Asn Leu Lys
                195                 200                 205

Tyr Val Ala Trp Val Phe Glu Thr Val Pro Asp Ser Ile Phe Glu Ser
    210                 215                 220

His His Ile Ser Ser Phe Thr Leu Glu Tyr Arg Arg Glu Cys Thr Arg
225                 230                 235                 240

Asp Ser Val Leu Arg Ser Leu Thr Thr Val Ser Gly Ser Ser Glu
                245                 250                 255

Ala Gly Leu Val Cys Asp His Leu Leu Gln Leu Glu Gly Gly Ser Glu
                260                 265                 270

Val Leu Arg Ala Arg Thr Glu Trp Arg Pro Lys Leu Thr Asp Ser Phe
    275                 280                 285

Arg Gly Ile Ser Val Ile Pro Ala Glu Pro Arg Val
290                 295                 300

<210> SEQ ID NO 21
<211> LENGTH: 831
<212> TYPE: DNA
<213> ORGANISM: Artificial sequence
<220> FEATURE:
<223> OTHER INFORMATION: Synthetic polynucleotide

<400> SEQUENCE: 21
ggcctggtgt atcgtcagaa tttcagtatt cgctcctacg aaatcggtgt ggataaacgt      60
gcatcggttg aagctctgat gaaccatttt caagaaacca gcctgaatca ctgcaaatgt     120
attggcctga tgcatggcgg tttcggttgc accccggaaa tgacgcgtcg caatctgatc     180
tgggtggttg ccaaaatgct ggtgcacgtt gaacgctatc cgtggtgggg cgatgtcgtg     240
cagattaaca cctggatctc ctcatcgggt aaaaatggca tgggtcgtga ctggcatgtg     300
cacgattgtc aaaccggcct gccgattatg cgcggcacgt ctgtctgggt gatgatggat     360
aaacacaccc gtcgcctgag taaactgccg gaagaagttc gtgccgaaat cacgccgttt     420
ttctcggaac gtgatgcagt gctggatgac aacggccgca aactgccgaa atttgatgac     480
gattcagcag ctcatgttcg tcgcggtctg accccgcgct ggcatgactt cgatgtcaat     540
cagcacgtga acaatgttaa atacgtcggc tggatcctgg aatccgttcc ggtctggatg     600
```

```
ctggacggtt atgaagttgc gaccatgtca ctggaatacc gtcgcgaatg ccgtatggat    660
tcagttgtcc agtcgctgac ggcagtcagc tctgaccacg cggatggtag cccgattgtg    720
tgtcagcatc tgctgcgcct ggaagatggc accgaaatcg tgcgtggtca aacggaatgg    780
cgcccggcaa ttgaaggtcg cgctcatcac caccatcatc accatcacta a             831
```

<210> SEQ ID NO 22
<211> LENGTH: 276
<212> TYPE: PRT
<213> ORGANISM: Artificial sequence
<220> FEATURE:
<223> OTHER INFORMATION: Synthetic polypeptide

<400> SEQUENCE: 22

```
Gly Leu Val Tyr Arg Gln Asn Phe Ser Ile Arg Ser Tyr Glu Ile Gly
1               5                   10                  15

Val Asp Lys Arg Ala Ser Val Glu Ala Leu Met Asn His Phe Gln Glu
            20                  25                  30

Thr Ser Leu Asn His Cys Lys Cys Ile Gly Leu Met His Gly Gly Phe
        35                  40                  45

Gly Cys Thr Pro Glu Met Thr Arg Arg Asn Leu Ile Trp Val Val Ala
    50                  55                  60

Lys Met Leu Val His Val Glu Arg Tyr Pro Trp Trp Gly Asp Val Val
65                  70                  75                  80

Gln Ile Asn Thr Trp Ile Ser Ser Gly Lys Asn Gly Met Gly Arg
                85                  90                  95

Asp Trp His Val His Asp Cys Gln Thr Gly Leu Pro Ile Met Arg Gly
            100                 105                 110

Thr Ser Val Trp Val Met Met Asp Lys His Thr Arg Arg Leu Ser Lys
        115                 120                 125

Leu Pro Glu Glu Val Arg Ala Glu Ile Thr Pro Phe Phe Ser Glu Arg
    130                 135                 140

Asp Ala Val Leu Asp Asp Asn Gly Arg Lys Leu Pro Lys Phe Asp Asp
145                 150                 155                 160

Asp Ser Ala Ala His Val Arg Arg Gly Leu Thr Pro Arg Trp His Asp
                165                 170                 175

Phe Asp Val Asn Gln His Val Asn Asn Val Lys Tyr Val Gly Trp Ile
            180                 185                 190

Leu Glu Ser Val Pro Val Trp Met Leu Asp Gly Tyr Glu Val Ala Thr
        195                 200                 205

Met Ser Leu Glu Tyr Arg Arg Glu Cys Arg Met Asp Ser Val Val Gln
    210                 215                 220

Ser Leu Thr Ala Val Ser Ser Asp His Ala Asp Gly Ser Pro Ile Val
225                 230                 235                 240

Cys Gln His Leu Leu Arg Leu Glu Asp Gly Thr Glu Ile Val Arg Gly
                245                 250                 255

Gln Thr Glu Trp Arg Pro Ala Ile Glu Gly Arg Ala His His His His
            260                 265                 270

His His His His
        275
```

<210> SEQ ID NO 23
<211> LENGTH: 1245
<212> TYPE: DNA
<213> ORGANISM: Artificial sequence
<220> FEATURE:

<223> OTHER INFORMATION: Synthetic polynucleotide

<400> SEQUENCE: 23

| | |
|---|---|
| atggttgctt cggttgctgc ttcttcttct ttcttccctg ttccttcgtc ttcttcttcc | 60 |
| gcttctgcta aggcttctcg aggcatcccc gatggcctgg acgtccgagg tatcgtggcc | 120 |
| aagcctgctt cctcttcggg ttggatgcag gccaaggctt ctgcccgagc tatccccaag | 180 |
| attgacgata ccaaggtcgg actgcgaact gatgttgagg aagacgccgc ttccaccgcc | 240 |
| cgacgaactt cttacaacca gctccctgac tggtcgatgc tgctcgccgc tatccgaacc | 300 |
| attttctccg ccgctgagaa gcagtggact ctgctcgact ctaagaagcg aggcgccgat | 360 |
| gctgttgccg acgcttccgg agttggcaag atggtcaaga acggcctggt ctaccgacag | 420 |
| aacttctcga tccgatccta cgagattggt gtggacaagc gagcctcggt ggaggctctc | 480 |
| atgaaccact tccaggagac ctccctgaac cattgcaagt gtatcggcct catgcacggc | 540 |
| ggttttggtt gcaccccga gatgactcga cgaaacctga tttgggtcgt ggccaagatg | 600 |
| ctcgtccacg tggagcgata cccttggtgg ggagacgttg tccagatcaa cacctggatt | 660 |
| tcctcttcgg gcaagaacgg tatgggacga gattggcacg tgcatgactg tcagaccgga | 720 |
| ctgcccatca tgcgaggcac ttctgtttgg gtcatgatgg acaagcatac ccgacgactg | 780 |
| tcgaagctcc ccgaggaagt ccgagccgag attactcctt tcttttctga gcgagacgct | 840 |
| gtgctggacg ataacggacg aaagctcccc aagttcgacg atgactctgc tgctcacgtg | 900 |
| cgacgaggac tcacccctcg atggcacgat tttgacgtta accagcatgt caacaacgtg | 960 |
| aagtacgttg gttggattct ggagtctgtg cccgtttgga tgctcgatgg atacgaggtg | 1020 |
| gccaccatgt ccctggagta ccgacgagag tgccgaatgg actctgtggt tcagtcgctc | 1080 |
| accgccgttt cctctgatca tgctgacggt tctcctatcg tctgtcagca cctgctccga | 1140 |
| ctggaggacg gtaccgagat tgtccgagga cagactgagt ggcgacctaa gcagcaggcc | 1200 |
| cgagatctgg gaaacatggg tctccaccct accgagtcca gtaa | 1245 |

<210> SEQ ID NO 24
<211> LENGTH: 414
<212> TYPE: PRT
<213> ORGANISM: Cocos nucifera
<220> FEATURE:
<221> NAME/KEY: MISC_FEATURE
<223> OTHER INFORMATION: lauroyl ACP- thioesterase

<400> SEQUENCE: 24

Met Val Ala Ser Val Ala Ala Ser Ser Phe Phe Pro Val Pro Ser
1               5                   10                  15

Ser Ser Ser Ala Ser Ala Lys Ala Ser Arg Gly Ile Pro Asp Gly
            20                  25                  30

Leu Asp Val Arg Gly Ile Val Ala Lys Pro Ala Ser Ser Ser Gly Trp
            35                  40                  45

Met Gln Ala Lys Ala Ser Ala Arg Ala Ile Pro Lys Ile Asp Asp Thr
        50                  55                  60

Lys Val Gly Leu Arg Thr Asp Val Glu Glu Asp Ala Ala Ser Thr Ala
65                  70                  75                  80

Arg Arg Thr Ser Tyr Asn Gln Leu Pro Asp Trp Ser Met Leu Leu Ala
                85                  90                  95

Ala Ile Arg Thr Ile Phe Ser Ala Ala Glu Lys Gln Trp Thr Leu Leu
            100                 105                 110

Asp Ser Lys Lys Arg Gly Ala Asp Ala Val Ala Asp Ala Ser Gly Val

```
            115                 120                 125
Gly Lys Met Val Lys Asn Gly Leu Val Tyr Arg Gln Asn Phe Ser Ile
    130                 135                 140

Arg Ser Tyr Glu Ile Gly Val Asp Lys Arg Ala Ser Val Glu Ala Leu
145                 150                 155                 160

Met Asn His Phe Gln Glu Thr Ser Leu Asn His Cys Lys Cys Ile Gly
                165                 170                 175

Leu Met His Gly Gly Phe Gly Cys Thr Pro Glu Met Thr Arg Arg Asn
            180                 185                 190

Leu Ile Trp Val Val Ala Lys Met Leu Val His Val Glu Arg Tyr Pro
        195                 200                 205

Trp Trp Gly Asp Val Val Gln Ile Asn Thr Trp Ile Ser Ser Ser Gly
    210                 215                 220

Lys Asn Gly Met Gly Arg Asp Trp His Val His Asp Cys Gln Thr Gly
225                 230                 235                 240

Leu Pro Ile Met Arg Gly Thr Ser Val Trp Val Met Met Asp Lys His
                245                 250                 255

Thr Arg Arg Leu Ser Lys Leu Pro Glu Glu Val Arg Ala Glu Ile Thr
            260                 265                 270

Pro Phe Phe Ser Glu Arg Asp Ala Val Leu Asp Asp Asn Gly Arg Lys
        275                 280                 285

Leu Pro Lys Phe Asp Asp Ser Ala Ala His Val Arg Arg Gly Leu
    290                 295                 300

Thr Pro Arg Trp His Asp Phe Asp Val Asn Gln His Val Asn Asn Val
305                 310                 315                 320

Lys Tyr Val Gly Trp Ile Leu Glu Ser Val Pro Val Trp Met Leu Asp
                325                 330                 335

Gly Tyr Glu Val Ala Thr Met Ser Leu Glu Tyr Arg Arg Glu Cys Arg
            340                 345                 350

Met Asp Ser Val Val Gln Ser Leu Thr Ala Val Ser Ser Asp His Ala
        355                 360                 365

Asp Gly Ser Pro Ile Val Cys Gln His Leu Leu Arg Leu Glu Asp Gly
    370                 375                 380

Thr Glu Ile Val Arg Gly Gln Thr Glu Trp Arg Pro Lys Gln Gln Ala
385                 390                 395                 400

Arg Asp Leu Gly Asn Met Gly Leu His Pro Thr Glu Ser Lys
                405                 410

<210> SEQ ID NO 25
<211> LENGTH: 894
<212> TYPE: DNA
<213> ORGANISM: Artificial sequence
<220> FEATURE:
<223> OTHER INFORMATION: Synthetic polynucleotide

<400> SEQUENCE: 25
catatgcatt ttggtctgca tggtctggtt tttcgccgca cctttgctat tcgtagttat      60
gaagttggcc cggaccgctc aacctcgatt ctggcggtta tgaaccacat gcaggaagcg     120
accctgaatc acgccaaaag cgtcggcatc ctgggcgatg gtttcggcac cacgctggaa     180
atgtctaaac gtgacctgat gtgggtggtt cgtcgcaccc atgtcgcagt ggaacgctat     240
ccgaccctgg gcgatacggt tgaagtcgaa tgctggattg gtgctagtgg caacaatggt     300
atgcgtcgcg atttcctggt gcgtgactgc aaaaccggtg aaatcctgac cgctgtacg     360 tcactgtcgg tgctgatgaa cacccgtacg cgtcgcctgt ctacgattcc ggatgaagtt     420
```

-continued

```
cgcggcgaaa tcggtccggc gtttattgac aacgtggccg ttaaagatga cgaaatcaaa    480
aaactgcaga aactgaacga tagcaccgca gactatattc aaggcggtct gacgccgcgt    540
tggaacgatc tggacgttaa tcagcatgtc aacaatctga atacgtcgc gtgggtgttt     600 gaaaccgtgc cggatagcat cttcgaatct catcacatta gctcttttac cctggaatac    660
cgtcgcgaat gcacgcgtga tagtgtgctg cgctccctga ccaccgttag tggcggtagt    720
tccgaagcgg gtctggtctg tgaccacctg ctgcaactgg aaggtggttc cgaagtgctg    780
cgtgcacgta ccgaatggcg tccgaaactg acggattcat ttcgcggcat ttcggttatc    840
ccggcaattg aaggtcgcgc tcatcaccac catcatcacc atcaccatca ctaa          894
```

<210> SEQ ID NO 26
<211> LENGTH: 297
<212> TYPE: PRT
<213> ORGANISM: Artificial sequence
<220> FEATURE:
<223> OTHER INFORMATION: Synthetic polypeptide

<400> SEQUENCE: 26

```
His Met His Phe Gly Leu His Gly Leu Val Phe Arg Arg Thr Phe Ala
1               5                   10                  15

Ile Arg Ser Tyr Glu Val Gly Pro Asp Arg Ser Thr Ser Ile Leu Ala
            20                  25                  30

Val Met Asn His Met Gln Glu Ala Thr Leu Asn His Ala Lys Ser Val
        35                  40                  45

Gly Ile Leu Gly Asp Gly Phe Gly Thr Thr Leu Glu Met Ser Lys Arg
    50                  55                  60

Asp Leu Met Trp Val Val Arg Arg Thr His Val Ala Val Glu Arg Tyr
65                  70                  75                  80

Pro Thr Trp Gly Asp Thr Val Glu Val Glu Cys Trp Ile Gly Ala Ser
                85                  90                  95

Gly Asn Asn Gly Met Arg Arg Asp Phe Leu Val Arg Asp Cys Lys Thr
            100                 105                 110

Gly Glu Ile Leu Thr Arg Cys Thr Ser Leu Ser Val Leu Met Asn Thr
        115                 120                 125

Arg Thr Arg Arg Leu Ser Thr Ile Pro Asp Glu Val Arg Gly Glu Ile
    130                 135                 140

Gly Pro Ala Phe Ile Asp Asn Val Ala Val Lys Asp Asp Glu Ile Lys
145                 150                 155                 160

Lys Leu Gln Lys Leu Asn Asp Ser Thr Ala Asp Tyr Ile Gln Gly Gly
                165                 170                 175

Leu Thr Pro Arg Trp Asn Asp Leu Asp Val Asn Gln His Val Asn Asn
            180                 185                 190

Leu Lys Tyr Val Ala Trp Val Phe Glu Thr Val Pro Asp Ser Ile Phe
        195                 200                 205

Glu Ser His His Ile Ser Ser Phe Thr Leu Glu Tyr Arg Arg Glu Cys
    210                 215                 220

Thr Arg Asp Ser Val Leu Arg Ser Leu Thr Thr Val Ser Gly Gly Ser
225                 230                 235                 240

Ser Glu Ala Gly Leu Val Cys Asp His Leu Leu Gln Leu Glu Gly Gly
                245                 250                 255

Ser Glu Val Leu Arg Ala Arg Thr Glu Trp Arg Pro Lys Leu Thr Asp
            260                 265                 270

Ser Phe Arg Gly Ile Ser Val Ile Pro Ala Ile Glu Gly Arg Ala His
```

```
              275                 280                 285

His His His His His His His His His
                    290                 295

<210> SEQ ID NO 27
<211> LENGTH: 930
<212> TYPE: DNA
<213> ORGANISM: Yarrowia lipolytica
<220> FEATURE:
<221> NAME/KEY: misc_feature
<223> OTHER INFORMATION: palmitoyl-acyl carrier protein

<400> SEQUENCE: 27
atgaaactcg ttactctggc aatccagcta tccacagtgc tagccactac cccagtggtt      60
ctctggcatg gtctcggcga cagatatgac tctccaggaa tgaccggtgt ggcggaccaa     120
atccgcgaca tttaccctga catttacgtg cattcagtcg gactctctga agacggcgga     180
aaagatcagc aaatgggtct tctaggcaac gtaagagagc aagttgagag tgtctgcgac     240
cagctggcag caataccaga gttgaagggc gggttcaatg ccatcggatt ttcccaagga     300
ggtctgtttc ttcgttcata cgccgagttg tgtccttga caaacgcctc agctcctgtt      360
ctccgaaagc tcatcacatt tggctcccct cataacggaa ttgctgatat gccgctctgt     420
gggcccagcg acttcctttg caagtctcgt aacaagctgt tcaagagtca ggtgtggact     480
aagaactctc aaacgaatgt ggtagtggca cagtattatc gggaccctaa ccacatggac     540
gtgtacctgg agaagtctgg atttctggca gacatcaaca acgagaggca acaaaagaac     600
aagacctacg acctgtctta tttggagaag tttgtcatgg tcatgttctc ggaggatacc     660
acagtagtgc ctatggagag tgcatggttc caagaggtgg atctcgaaag tgggcaagtc     720
acccaccttg aagacagaga gatataccaa gaggactgga ttggacttaa gaagcttgga     780
aagcgtggtg atcttgagtt ccacacggtc catggacagc acatggagat caacgacgac     840
gtgattgaaa cgtttgcctt gagatattta ggcgacgatg acgatatcaa ggccggtgac     900
gactttgtgt ttgtaaacca agctaaatag                                      930

<210> SEQ ID NO 28
<211> LENGTH: 309
<212> TYPE: PRT
<213> ORGANISM: Yarrowia lipolytica
<220> FEATURE:
<221> NAME/KEY: MISC_FEATURE
<223> OTHER INFORMATION: palmitoyl-acyl carrier protein

<400> SEQUENCE: 28

Met Lys Leu Val Thr Leu Ala Ile Gln Leu Ser Thr Val Leu Ala Thr
1               5                   10                  15

Thr Pro Val Val Leu Trp His Gly Leu Gly Asp Arg Tyr Asp Ser Pro
                20                  25                  30

Gly Met Thr Gly Val Ala Asp Gln Ile Arg Asp Ile Tyr Pro Asp Ile
            35                  40                  45

Tyr Val His Ser Val Gly Leu Ser Glu Asp Gly Gly Lys Asp Gln Gln
        50                  55                  60

Met Gly Leu Leu Gly Asn Val Arg Glu Gln Val Glu Ser Val Cys Asp
65                  70                  75                  80

Gln Leu Ala Ala Ile Pro Glu Leu Lys Gly Gly Phe Asn Ala Ile Gly
                85                  90                  95

Phe Ser Gln Gly Gly Leu Phe Leu Arg Ser Tyr Ala Glu Leu Cys Pro
                100                 105                 110
```

```
Leu Thr Asn Ala Ser Ala Pro Val Leu Arg Lys Leu Ile Thr Phe Gly
            115                 120                 125

Ser Pro His Asn Gly Ile Ala Asp Met Pro Leu Cys Gly Pro Ser Asp
        130                 135                 140

Phe Leu Cys Lys Ser Arg Asn Lys Leu Phe Lys Ser Gln Val Trp Thr
145                 150                 155                 160

Lys Asn Ser Gln Thr Asn Val Val Val Ala Gln Tyr Tyr Arg Asp Pro
                165                 170                 175

Asn His Met Asp Val Tyr Leu Glu Lys Ser Gly Phe Leu Ala Asp Ile
            180                 185                 190

Asn Asn Glu Arg Gln Gln Lys Asn Lys Thr Tyr Asp Leu Ser Tyr Leu
        195                 200                 205

Glu Lys Phe Val Met Val Met Phe Ser Glu Asp Thr Thr Val Val Pro
    210                 215                 220

Met Glu Ser Ala Trp Phe Gln Glu Val Asp Leu Glu Ser Gly Gln Val
225                 230                 235                 240

Thr His Leu Glu Asp Arg Glu Ile Tyr Gln Glu Asp Trp Ile Gly Leu
                245                 250                 255

Lys Lys Leu Gly Lys Arg Gly Asp Leu Glu Phe His Thr Val His Gly
            260                 265                 270

Gln His Met Glu Ile Asn Asp Asp Val Ile Glu Thr Phe Ala Leu Arg
        275                 280                 285

Tyr Leu Gly Asp Asp Asp Ile Lys Ala Gly Asp Asp Phe Val Phe
    290                 295                 300

Val Asn Gln Ala Lys
305

<210> SEQ ID NO 29
<211> LENGTH: 2043
<212> TYPE: DNA
<213> ORGANISM: Candida tropicalis
<220> FEATURE:
<221> NAME/KEY: misc_feature
<223> OTHER INFORMATION: cytochrome P450 reductase

<400> SEQUENCE: 29
atggcattag ataagttaga tttatatgtt attataacat tggtggttgc aattgcagct      60
tattttgcaa agaatcagtt tcttgaccaa caacaagata ccgggttcct taatactgat     120
agtggagatg gtaattcaag agatatctta caagctttga agaagaacaa taaaaatacg     180
ttattattat ttggatccca aacaggtaca gcagaagatt atgccaacaa attgtcaaga     240
gaattgcatt caagatttgg tttgaaaacc atggttgctg atttcgctga ttatgatttc     300
gaaaacttcg gagatattac tgaagatatc ttggttttct ttattgttgc tacttatggt     360
gaaggtgaac caccgataa tgctgacgaa tttcacactt ggttgactga agaagctgac     420
accttgagta cttgtaaata tactgttttt ggtttgggta attcaactta tgaattcttc     480
aatgctattg gtagaaaatt tgacagattg ttgggagaaa aaggtggtga cagatttgct     540
gaatacggtg aaggtgacga tggtactggt actttagatg aagatttctt ggcctggaag     600
gataacgtgt tgattccttt aaagaatgat ttgaattttg aagaaaaaga gttgaaatac     660
gaaccaaatg ttaaattgac tgaaagagat gatttatctg gcaatgatcc agaagtctcc     720
ttgggtgaac aaatgtcaa atacattaaa tctgaaggtg ttgacttaac taaaggtcca     780
tttgatcata ctcatccatt tttggctaga attgttaaaa ctaaagaatt gtttacttct     840
```

```
gaagacagac attgtgttca tgttgaattt gatatttctg aatcaaactt gaaatatacc      900
accggtgatc atcttgcaat ctggccatct aactctgatg aaaacattaa gcaatttgcc      960
aaatgttttg gtttagaaga caaacttgat actgttattg aattgaaagc tttggattcc     1020
acttattcca tcccattccc taatccaatc acttatggag ctgttattag acaccatttg     1080
gaaatttcag gtcctgtttc tagacaattt ttcttatcta ttgctggatt tgcccctgat     1140
gaagaaacta aaaagtcatt tactagaatt ggtggtgata agcaagaatt tgctagtaaa     1200
gtcacccgta gaaaattcaa cattgccgat gctttattat ttgcttccaa caacagacca     1260
tggtccgatg ttccattcga attccttatt gaaaatgtcc aacacttaac tcctcgttat     1320
tactccattt cttcttcctc attaagtgaa aagcaaacca ttaatgttac tgctgttgtt     1380
gaagccgaag aagaagctga tggaagacca gttactggtg ttgtcaccaa cttgttgaag     1440
aatattgaaa ttgaacaaaa caaaactggt gaaaccccaa tggttcatta tgatttgaat     1500
ggtccaagag gcaaatttag caagttcaga ttgccagttc acgttagaag atctaatttc     1560
aaattaccaa agaatagcac taccccagtt attttgattg gtccaggtac cggtgttgca     1620
ccattgagag gttttgttag agaaagagtt caacaagtta aaaatggtgt taatgttggt     1680
aagactgtat tgttttatgg atgtagaaat tccgaacaag atttcttgta caaacaagaa     1740
tggagtgaat atgcctcagt attgggagaa aatttcgaaa tgtttaatgc cttctcaaga     1800
caagatccaa ctaagaaagt ttatgttcaa gataagattt tagaaaatag tgctcttgtt     1860
gatgagttat tatctagtgg agcaattatt tatgtttgtg gtgatgccag tagaatggct     1920
agagatgttc aagctgcaat tgccaagatt gttgccaaaa gtagagatat ccacgaagat     1980
aaagctgctg aattggttaa atcttggaaa gttcaaaata gataccaaga agatgtctgg     2040
taa                                                                    2043
```

<210> SEQ ID NO 30
<211> LENGTH: 680
<212> TYPE: PRT
<213> ORGANISM: Candida tropicalis
<220> FEATURE:
<221> NAME/KEY: MISC_FEATURE
<223> OTHER INFORMATION: cytochrome P450 reductase

<400> SEQUENCE: 30

```
Met Ala Leu Asp Lys Leu Asp Leu Tyr Val Ile Ile Thr Leu Val Val
1               5                   10                  15

Ala Ile Ala Ala Tyr Phe Ala Lys Asn Gln Phe Leu Asp Gln Gln Gln
            20                  25                  30

Asp Thr Gly Phe Leu Asn Thr Asp Ser Gly Asp Gly Asn Ser Arg Asp
        35                  40                  45

Ile Leu Gln Ala Leu Lys Lys Asn Asn Lys Asn Thr Leu Leu Leu Phe
    50                  55                  60

Gly Ser Gln Thr Gly Thr Ala Glu Asp Tyr Ala Asn Lys Leu Ser Arg
65                  70                  75                  80

Glu Leu His Ser Arg Phe Gly Leu Lys Thr Met Val Ala Asp Phe Ala
                85                  90                  95

Asp Tyr Asp Phe Glu Asn Phe Gly Asp Ile Thr Glu Asp Ile Leu Val
            100                 105                 110

Phe Phe Ile Val Ala Thr Tyr Gly Glu Gly Glu Pro Thr Asp Asn Ala
        115                 120                 125

Asp Glu Phe His Thr Trp Leu Thr Glu Glu Ala Asp Thr Leu Ser Thr
    130                 135                 140
```

-continued

```
Leu Lys Tyr Thr Val Phe Gly Leu Gly Asn Ser Thr Tyr Glu Phe Phe
145                 150                 155                 160

Asn Ala Ile Gly Arg Lys Phe Asp Arg Leu Gly Glu Lys Gly Gly
            165                 170                 175

Asp Arg Phe Ala Glu Tyr Gly Glu Gly Asp Gly Thr Gly Thr Leu
            180                 185                 190

Asp Glu Asp Phe Leu Ala Trp Lys Asp Asn Val Phe Asp Ser Leu Lys
        195                 200                 205

Asn Asp Leu Asn Phe Glu Glu Lys Glu Leu Lys Tyr Glu Pro Asn Val
        210                 215                 220

Lys Leu Thr Glu Arg Asp Asp Leu Ser Gly Asn Asp Pro Glu Val Ser
225                 230                 235                 240

Leu Gly Glu Pro Asn Val Lys Tyr Ile Lys Ser Glu Gly Val Asp Leu
                245                 250                 255

Thr Lys Gly Pro Phe Asp His Thr His Pro Phe Leu Ala Arg Ile Val
            260                 265                 270

Lys Thr Lys Glu Leu Phe Thr Ser Glu Asp Arg His Cys Val His Val
        275                 280                 285

Glu Phe Asp Ile Ser Glu Ser Asn Leu Lys Tyr Thr Thr Gly Asp His
        290                 295                 300

Leu Ala Ile Trp Pro Ser Asn Ser Asp Glu Asn Ile Lys Gln Phe Ala
305                 310                 315                 320

Lys Cys Phe Gly Leu Glu Asp Lys Leu Asp Thr Val Ile Glu Leu Lys
                325                 330                 335

Ala Leu Asp Ser Thr Tyr Ser Ile Pro Phe Pro Asn Pro Ile Thr Tyr
            340                 345                 350

Gly Ala Val Ile Arg His His Leu Glu Ile Ser Gly Pro Val Ser Arg
        355                 360                 365

Gln Phe Phe Leu Ser Ile Ala Gly Phe Ala Pro Asp Glu Glu Thr Lys
        370                 375                 380

Lys Ser Phe Thr Arg Ile Gly Gly Asp Lys Gln Glu Phe Ala Ser Lys
385                 390                 395                 400

Val Thr Arg Arg Lys Phe Asn Ile Ala Asp Ala Leu Leu Phe Ala Ser
                405                 410                 415

Asn Asn Arg Pro Trp Ser Asp Val Pro Phe Glu Phe Leu Ile Glu Asn
            420                 425                 430

Val Gln His Leu Thr Pro Arg Tyr Tyr Ser Ile Ser Ser Ser Ser Leu
        435                 440                 445

Ser Glu Lys Gln Thr Ile Asn Val Thr Ala Val Val Glu Ala Glu Glu
        450                 455                 460

Glu Ala Asp Gly Arg Pro Val Thr Gly Val Val Thr Asn Leu Leu Lys
465                 470                 475                 480

Asn Ile Glu Ile Glu Gln Asn Lys Thr Gly Glu Thr Pro Met Val His
                485                 490                 495

Tyr Asp Leu Asn Gly Pro Arg Gly Lys Phe Ser Lys Phe Arg Leu Pro
            500                 505                 510

Val His Val Arg Arg Ser Asn Phe Lys Leu Pro Lys Asn Ser Thr Thr
        515                 520                 525

Pro Val Ile Leu Ile Gly Pro Gly Thr Gly Val Ala Pro Leu Arg Gly
        530                 535                 540

Phe Val Arg Glu Arg Val Gln Gln Val Lys Asn Gly Val Asn Val Gly
545                 550                 555                 560
```

```
Lys Thr Val Leu Phe Tyr Gly Cys Arg Asn Ser Glu Gln Asp Phe Leu
            565                 570                 575

Tyr Lys Gln Glu Trp Ser Glu Tyr Ala Ser Val Leu Gly Glu Asn Phe
        580                 585                 590

Glu Met Phe Asn Ala Phe Ser Arg Gln Asp Pro Thr Lys Lys Val Tyr
            595                 600                 605

Val Gln Asp Lys Ile Leu Glu Asn Ser Ala Leu Val Asp Glu Leu Leu
        610                 615                 620

Ser Ser Gly Ala Ile Ile Tyr Val Cys Gly Asp Ala Ser Arg Met Ala
625                 630                 635                 640

Arg Asp Val Gln Ala Ala Ile Ala Lys Ile Val Ala Lys Ser Arg Asp
            645                 650                 655

Ile His Glu Asp Lys Ala Ala Glu Leu Val Lys Ser Trp Lys Val Gln
            660                 665                 670

Asn Arg Tyr Gln Glu Asp Val Trp
        675                 680
```

<210> SEQ ID NO 31
<211> LENGTH: 2043
<212> TYPE: DNA
<213> ORGANISM: Artificial sequence
<220> FEATURE:
<223> OTHER INFORMATION: Synthetic polynucleotide

<400> SEQUENCE: 31

```
atggctctgg ataaactgga cctgtatgtc atcatcacgc tggtcgtcgc aatcgctgcc      60
tacttcgcaa aaatcaatt cctggaccag caacaggata ccggttttct gaacacggat     120
tcaggcgacg gtaattcgcg tgatattctg caagccctga gaaaaacaa taaaaacacc     180
ctgctgctgt ttggtagcca gaccggcacg gcggaagatt atgccaataa actgagccgt     240
gaactgcatt ctcgcttcgg tctgaaaacg atggtggcgg attttgccga ttatgacttt     300
gaaaacttcg gcgatattac cgaagacatc ctggtctttt tcattgtggc tacctacggc     360
gaaggtgaac cgacggataa tgcggacgaa tttcacacct ggctgacgga agaagccgat     420
acctgtcaa cgctgaaata ccgttttc ggcctgggta actcgacgta cgaatttttc     480
aatgcgatcg tcgtaaatt tgatcgcctg ctgggcgaaa aaggcggtga ccgtttcgcc     540
gaatatggcg aaggtgatga cggcaccggt acgctggatg aagacttcct ggcatggaaa     600
gataacgtct ttgacagcct gaaaaacgat ctgaacttcg aagaaaaaga actgaaatac     660
gaaccgaacg ttaaactgac cgaacgcgat gacctgagcg gtaacgatcc ggaagtttcg     720
ctgggcgaac cgaatgtcaa atacattaaa agtgagggtg tggatctgac caaaggcccg     780
ttcgaccata cgcacccgtt tctggcgcgt attgttaaaa cgaaagaact gtttacgagc     840
gaagatcgcc attgcgttca cgtcgaattt gacatcagcg aatctaacct gaaatatacc     900
acgggtgatc atctggcgat ttggccgagt aactccgacg aaaatatcaa acagttcgcc     960
aaatgttttg gctggaaga taaactggac ccgtgattg aactgaaagc actggattca    1020
acgtattcga ttccgttcc gaatccgatc acctacggtg ctgtgattcg tcatcacctg    1080
gaaatcagcg gccggtttc tcgccaattt ttcctgagca ttgcaggctt cgctccggat    1140
gaagaaacca aaaatcttt tacgcgtatc ggcggtgaca acaggaatt tgccagtaaa    1200
gtgacccgtc gcaaattcaa cattgcagat gctctgctgt ttgcaagtaa caatcgtccg    1260
tggtccgacg ttccgtttga atttctgatc gaaaacgtcc aacacctgac cccgcgctat    1320
tacagcatta gctctagttc cctgtctgaa aaacagacca tcaatgttac ggcagtggtt    1380
```

```
gaagctgaag aagaagcgga tggtcgtccg gtcaccggtg tcgtgacgaa cctgctgaaa    1440
aacatcgaaa tcgaacagaa caaaaccggt gaaacgccga tggtgcatta tgatctgaat    1500
ggtccgcgtg gcaaattttc caaattccgc ctgccggtgc acgttcgtcg cagtaacttt    1560
aaactgccga aaaattccac cacgccggtt attctgatcg gtccgggtac cggtgtggca    1620
ccgctgcgtg gttttgttcg tgaacgcgtg caacaggtta aaaacggtgt caatgtgggc    1680
aaaaccgtgc tgttttacgg ttgccgcaac tctgaacaag atttcctgta taacaggaa    1740 tggagtgaat acgcatccgt tctgggcgaa aactttgaaa tgttcaatgc ttttcgcgt    1800 caagatccga ccaagaaagt gtatgtccag gacaaaattc tggaaaattc tgccctggtc    1860
gatgaactgc tgtcatcggg tgcaattatc tacgtgtgtg gcgatgcctc ccgtatggca    1920
cgcgacgtcc aggcagccat tgctaaaatc gtggcgaaat cacgcgatat ccatgaagac    1980
aaagcggcag aactggtcaa atcgtggaaa gtgcagaatc gttatcagga agatgtgtgg    2040
taa                                                                  2043

<210> SEQ ID NO 32
<211> LENGTH: 2115
<212> TYPE: DNA
<213> ORGANISM: Candida albicans
<220> FEATURE:
<221> NAME/KEY: misc_feature
<223> OTHER INFORMATION: fatty alcohol oxgenase

<400> SEQUENCE: 32
atggctccat ttttgcccga ccaggtcgac tacaaacacg tcgacaccct tatgttatta     60
tgtgacggga tcatccacga aaccaccgtg gacgaaatca agacgtcat tgccctgac     120 ttccccgccg acaaatacga ggagtacgtc aggacattca ccaaaccctc cgaaacccca    180
gggttcaggg aaaccgtcta caaccaccgtc aacgcaaaca ccatggatgc aatccaccag    240
ttcattatct tgaccaatgt tttgggatca agggtcttgg caccagcttt gaccaactcg    300
ttgactccta tcaaggacat gagcttggaa gaccgtgaaa agttgttagc ctcgtggcgt    360 gactcccta ttgctgctaa aaggaagttg ttcaggttgg tttctacgct taccttggtc    420
acgttcacga gattggccaa tgagttgcat ttgaaagcca ttcattatcc aggaagagaa    480
gaccgtgaaa aggcttatga aacccaggag attgacccctt taagtacca gttttggaa    540 aaaccgaagt tttacggcgc tgagttgtac ttgccagata ttgatgtgat cattattgga    600
tctggggccg gtgctggtgt cgtggcccac acttttgacca acgacggctt caagagttg    660 gttttggaaa agggcagata ctttagcaac tccgagttga acttttgatga caaggacggg    720 gtcaagaat tataccaaag tggaggtact ttgaccaccg tcaaccagca gttgtttgtt    780
cttgctggtt ccacttttgg tggtggtacc actgtcaatt ggtcggcctg tcttaaaacg    840
ccattcaagg tgcgtaagga atggtatgat gagtttggcg ttgactttgc tgccgatgaa    900
gcctacgaca aagcacagga ttatgtttgg cagcaaatgg gagcttctac cgaaggcatc    960
acccactctt tggctaacga gattattatt gaaggtggca agaaattagg ttacaaggcc   1020
aaggtattag accaaaacag cggtggtcat cctcatcaca gatgcggttt ctgttattttg   1080 ggttgtaagc acggtatcaa gcagggctct gttaataact ggtttagaga cgcagctgcc   1140
cacggttctc agttcatgca acaggttaga gttttgcaaa tccttaacaa gaagggcatc   1200
gcttatggta tcttgtgtga ggatgttgta accggtgcca agttcaccat tactggcccc   1260 aaaaagttg ttgttgccgc cggcgcctta aacactccat ctgtgttggt caactccgga   1320
```

-continued

```
ttcaagaaca agaacatcgg taagaactta actttgcatc cagtttctgt cgtgtttggt    1380
gattttggca aagacgttca agcagatcac ttccacaact ccatcatgac tgctctttgt    1440
tcagaagccg ctgatttaga cggcaagggt catggatgca gaattgaaac catcttgaac    1500
gctccattca tccaggcttc attcttacca tggagaggta gtaacgaggc tagacgagac    1560
ttgttgcgtt acaacaacat ggtggccatg ttacttctta gtcgtgatac caccagtggt    1620
tccgtttcgt cccatccaac taaacctgaa gcattagttg tcgagtacga cgtgaacaag    1680
tttgacagaa actccatctt gcaggcattg ttggtcactg ctgacttgtt gtacattcaa    1740
ggtgccaaga gaatccttag tccccaacca tgggtgccaa tttttgaatc cgacaagcca    1800
aaggataaga gatcaatcaa ggacgaggac tatgtcgaat ggagagccaa ggttgccaag    1860 attcctttg acacctacgg ctcgccttat ggttcggcgc atcaaatgtc ttcttgtcgt     1920
atgtcaggta agggtcctaa atacggtgct gttgataccg atggtagatt gtttgaatgt    1980
tcgaatgttt atgttgctga cgctagtctt ttgccaactg ctagcggtgc taatcctatg    2040
gtcaccacca tgactcttgc aagacatgtt gcgttaggtt tggcagactc cttgaagacc    2100
aaggccaagt tgtag                                                    2115
```

<210> SEQ ID NO 33
<211> LENGTH: 704
<212> TYPE: PRT
<213> ORGANISM: Candida albicans
<220> FEATURE:
<221> NAME/KEY: MISC_FEATURE
<223> OTHER INFORMATION: fatty alcohol oxgenase

<400> SEQUENCE: 33

```
Met Ala Pro Phe Leu Pro Asp Gln Val Asp Tyr Lys His Val Asp Thr
1               5                   10                  15

Leu Met Leu Leu Cys Asp Gly Ile Ile His Glu Thr Thr Val Asp Glu
            20                  25                  30

Ile Lys Asp Val Ile Ala Pro Asp Phe Pro Ala Asp Lys Tyr Glu Glu
        35                  40                  45

Tyr Val Arg Thr Phe Thr Lys Pro Ser Glu Thr Pro Gly Phe Arg Glu
    50                  55                  60

Thr Val Tyr Asn Thr Val Asn Ala Asn Thr Met Asp Ala Ile His Gln
65                  70                  75                  80

Phe Ile Ile Leu Thr Asn Val Leu Gly Ser Arg Val Leu Ala Pro Ala
                85                  90                  95

Leu Thr Asn Ser Leu Thr Pro Ile Lys Asp Met Ser Leu Glu Asp Arg
            100                 105                 110

Glu Lys Leu Leu Ala Ser Trp Arg Asp Ser Pro Ile Ala Ala Lys Arg
        115                 120                 125

Lys Leu Phe Arg Leu Val Ser Thr Leu Thr Leu Val Thr Phe Thr Arg
    130                 135                 140

Leu Ala Asn Glu Leu His Leu Lys Ala Ile His Tyr Pro Gly Arg Glu
145                 150                 155                 160

Asp Arg Glu Lys Ala Tyr Glu Thr Gln Glu Ile Asp Pro Phe Lys Tyr
                165                 170                 175

Gln Phe Leu Glu Lys Pro Lys Phe Tyr Gly Ala Glu Leu Tyr Leu Pro
            180                 185                 190

Asp Ile Asp Val Ile Ile Ile Gly Ser Gly Ala Gly Ala Gly Val Val
        195                 200                 205
```

Ala His Thr Leu Thr Asn Asp Gly Phe Lys Ser Leu Val Leu Glu Lys
210                 215                 220

Gly Arg Tyr Phe Ser Asn Ser Glu Leu Asn Phe Asp Asp Lys Asp Gly
225                 230                 235                 240

Val Gln Glu Leu Tyr Gln Ser Gly Gly Thr Leu Thr Thr Val Asn Gln
            245                 250                 255

Gln Leu Phe Val Leu Ala Gly Ser Thr Phe Gly Gly Thr Thr Val
        260                 265                 270

Asn Trp Ser Ala Cys Leu Lys Thr Pro Phe Lys Val Arg Lys Glu Trp
        275                 280                 285

Tyr Asp Glu Phe Gly Val Asp Phe Ala Asp Glu Ala Tyr Asp Lys
290                 295                 300

Ala Gln Asp Tyr Val Trp Gln Gln Met Gly Ala Ser Thr Glu Gly Ile
305                 310                 315                 320

Thr His Ser Leu Ala Asn Glu Ile Ile Ile Glu Gly Lys Lys Leu
            325                 330                 335

Gly Tyr Lys Ala Lys Val Leu Asp Gln Asn Ser Gly Gly His Pro His
            340                 345                 350

His Arg Cys Gly Phe Cys Tyr Leu Gly Cys Lys His Gly Ile Lys Gln
        355                 360                 365

Gly Ser Val Asn Asn Trp Phe Arg Asp Ala Ala Ala His Gly Ser Gln
370                 375                 380

Phe Met Gln Gln Val Arg Val Leu Gln Ile Leu Asn Lys Lys Gly Ile
385                 390                 395                 400

Ala Tyr Gly Ile Leu Cys Glu Asp Val Val Thr Gly Ala Lys Phe Thr
            405                 410                 415

Ile Thr Gly Pro Lys Lys Phe Val Val Ala Ala Gly Ala Leu Asn Thr
            420                 425                 430

Pro Ser Val Leu Val Asn Ser Gly Phe Lys Asn Lys Asn Ile Gly Lys
        435                 440                 445

Asn Leu Thr Leu His Pro Val Ser Val Val Phe Gly Asp Phe Gly Lys
        450                 455                 460

Asp Val Gln Ala Asp His Phe His Asn Ser Ile Met Thr Ala Leu Cys
465                 470                 475                 480

Ser Glu Ala Ala Asp Leu Asp Gly Lys Gly His Gly Cys Arg Ile Glu
            485                 490                 495

Thr Ile Leu Asn Ala Pro Phe Ile Gln Ala Ser Phe Leu Pro Trp Arg
        500                 505                 510

Gly Ser Asn Glu Ala Arg Arg Asp Leu Leu Arg Tyr Asn Asn Met Val
        515                 520                 525

Ala Met Leu Leu Leu Ser Arg Asp Thr Thr Ser Gly Ser Val Ser Ser
530                 535                 540

His Pro Thr Lys Pro Glu Ala Leu Val Val Glu Tyr Asp Val Asn Lys
545                 550                 555                 560

Phe Asp Arg Asn Ser Ile Leu Gln Ala Leu Leu Val Thr Ala Asp Leu
            565                 570                 575

Leu Tyr Ile Gln Gly Ala Lys Arg Ile Leu Ser Pro Gln Pro Trp Val
            580                 585                 590

Pro Ile Phe Glu Ser Asp Lys Pro Lys Asp Lys Arg Ser Ile Lys Asp
        595                 600                 605

Glu Asp Tyr Val Glu Trp Arg Ala Lys Val Ala Lys Ile Pro Phe Asp
610                 615                 620

Thr Tyr Gly Ser Pro Tyr Gly Ser Ala His Gln Met Ser Ser Cys Arg

```
                625                 630                 635                 640
            Met Ser Gly Lys Gly Pro Lys Tyr Gly Ala Val Asp Thr Asp Gly Arg
                            645                 650                 655

Leu Phe Glu Cys Ser Asn Val Tyr Val Ala Asp Ala Ser Leu Leu Pro
                        660                 665                 670

Thr Ala Ser Gly Ala Asn Pro Met Val Thr Thr Met Thr Leu Ala Arg
                            675                 680                 685

His Val Ala Leu Gly Leu Ala Asp Ser Leu Lys Thr Lys Ala Lys Leu
                        690                 695                 700

<210> SEQ ID NO 34
<211> LENGTH: 2115
<212> TYPE: DNA
<213> ORGANISM: Artificial sequence
<220> FEATURE:
<223> OTHER INFORMATION: Synthetic polynucleotide

<400> SEQUENCE: 34
atggctccat ttttgcccga ccaggtcgac tacaaacacg tcgacaccct tatgttatta      60
tgtgacggga tcatccacga aaccaccgtg gacgaaatca agacgtcat tgcccctgac     120 ttccccgccg acaaatacga ggagtacgtc aggacattca ccaaaccctc cgaaacccca     180
gggttcaggg aaaccgtcta caacaccgtc aacgcaaaca ccatggatgc aatccaccag     240
ttcattatct tgaccaatgt tttgggatca agggtcttgg caccagcttt gaccaactcg     300
ttgactccta tcaaggacat gagcttggaa gaccgtgaaa agttgttagc ctcgtggcgt     360
gactccccta ttgctgctaa aggaagttg ttcaggttgg tttctacgct taccttggtc     420
acgttcacga gattggccaa tgagttgcat ttgaaagcca ttcattatcc aggaagagaa     480
gaccgtgaaa aggcttatga aacccaggag attgacccctt ttaagtacca gttttggaa     540 aaaccgaagt tttacggcgc tgagttgtac ttgccagata ttgatgtgat cattattgga     600
tctggggccg gtgctggtgt cgtggcccac acttttgacca acgacggctt caagagtttg     660
gttttggaaa agggcagata ctttagcaac tccgagttga actttgatga caaggacggg     720
gttcaagaat ataccaaag tggaggtact ttgaccaccg tcaaccagca gttgtttgtt     780
cttgctggtt ccacttttgg tggtggtacc actgtcaatt ggtcggcctg tcttaaaacg     840
ccattcaagg tgcgtaagga atggtatgat gagtttggcg ttgactttgc tgccgatgaa     900
gcctacgaca agcacagga ttatgtttgg cagcaaatgg gagcttctac cgaaggcatc     960
acccactctt tggctaacga gattattatt gaaggtggca agaaattagg ttacaaggcc    1020
aaggtattag accaaaacag cggtggtcat cctcatcaca gatgcggttt ctgttatttg    1080
ggttgtaagc acggtatcaa gcagggctct gttaataact ggtttagaga cgcagctgcc    1140
cacggttctc agttcatgca acaggttaga gttttgcaaa tccttaacaa gaagggcatc    1200
gcttatggta tcttgtgtga ggatgttgta accggtgcca agttcaccat tactggcccc    1260
aaaaagtttg ttgttgccgc cggcgcctta aacactccat ctgtgttggt caactccgga    1320
ttcaagaaca gaacatcgg taagaactta actttgcatc cagtttctgt cgtgtttggt    1380
gattttggca agacgttca gcagatcac ttccacaact ccatcatgac tgctcttgt     1440 tcagaagccg ctgatttaga cggcaagggt catggatgca gaattgaaac catcttgaac    1500
gctccattca tccaggcttc attcttacca tggagaggta gtaacgaggc tagacgagac    1560
ttgttgcgtt acaacaacat ggtggccatg ttacttctta gtcgtgatac caccagtggt    1620
tccgtttcgt cccatccaac taaacctgaa gcattagttg tcgagtacga cgtgaacaag    1680
```

```
tttgacagaa actccatctt gcaggcattg ttggtcactg ctgacttgtt gtacattcaa      1740
ggtgccaaga gaatccttag tccccaacca tgggtgccaa tttttgaatc cgacaagcca      1800
aaggataaga gatcaatcaa ggacgaggac tatgtcgaat ggagagccaa ggttgccaag      1860 attcctttg acacctacgg ctcgccttat ggttcggcgc atcaaatgtc ttcttgtcgt       1920
atgtcaggta agggtcctaa atacggtgct gttgataccg atggtagatt gtttgaatgt      1980
tcgaatgttt atgttgctga cgctagtctt ttgccaactg ctagcggtgc taatcctatg      2040
gtcaccacca tgactcttgc aagacatgtt gcgttaggtt tggcagactc cttgaagacc      2100
aaggccaagt tgtag                                                       2115
```

<210> SEQ ID NO 35
<211> LENGTH: 768
<212> TYPE: DNA
<213> ORGANISM: Candida albicans
<220> FEATURE:
<221> NAME/KEY: misc_feature
<223> OTHER INFORMATION: fatty aldehyde hydrogenase

<400> SEQUENCE: 35

```
atgccagatg gtactccaag attcacatgt aaaggtaaag aaattcttca tttcatgggt       60
tgctctacct tctcccaata cactgttgtt gctgatattt ctgtcgttgc cattaatgaa      120
aaagctgagt tgaaaaagc ttgtttgtta ggatgtggta ttactactgg ttacggtgcg      180
gccaccatta ctgcaaatgt ccaagaaggt gataatgttg ctgtctttgg tggtggttgt      240
gttggtttat ctgttatcca aggttgtaaa gaaagaaaag tcaacaagat cattttggtt      300
gatataaacg acaaaaaga gaatggggt aaacaatttg gtgccactga ttttgtcaac       360
tcaactaaat tgccagaggg gactaccatt gtcgataaat taattgaaat gaccgatggt      420
ggttgtgact acacttttga ttgtactggt aacgtcaacg tcatgagaaa tgcattagaa      480
gcttgtcaca aaggttgggg tacttctatt atcattgggg ttgctgctgc tggtaaagaa      540
atctctacca gaccatttca attagttacc ggtagggtgt ggaaaggtgc tgcctttggt      600
ggtgttaaag gtagatctca attgccaggt atagttgaag attacttgga tggtaaactc      660
aaggttgaag aattcatcac ccacagagaa ccattggaca agatcaacac tgctttcgat      720
gaaatgcacg gaggcgactg tattagagct gttgtttctt tatggtga                  768
```

<210> SEQ ID NO 36
<211> LENGTH: 255
<212> TYPE: PRT
<213> ORGANISM: Candida albicans
<220> FEATURE:
<221> NAME/KEY: MISC_FEATURE
<223> OTHER INFORMATION: fatty aldehyde hydrogenase

<400> SEQUENCE: 36

```
Met Pro Asp Gly Thr Pro Arg Phe Thr Cys Lys Gly Lys Glu Ile Leu
1               5                   10                  15

His Phe Met Gly Cys Ser Thr Phe Ser Gln Tyr Thr Val Val Ala Asp
            20                  25                  30

Ile Ser Val Val Ala Ile Asn Glu Lys Ala Glu Phe Glu Lys Ala Cys
        35                  40                  45

Leu Leu Gly Cys Gly Ile Thr Thr Gly Tyr Gly Ala Ala Thr Ile Thr
    50                  55                  60

Ala Asn Val Gln Glu Gly Asp Asn Val Ala Val Phe Gly Gly Gly Cys
65                  70                  75                  80
```

```
Val Gly Leu Ser Val Ile Gln Gly Cys Lys Glu Arg Lys Val Asn Lys
            85                  90                  95

Ile Ile Leu Val Asp Ile Asn Asp Lys Lys Glu Glu Trp Gly Lys Gln
            100                 105                 110

Phe Gly Ala Thr Asp Phe Val Asn Ser Thr Lys Leu Pro Glu Gly Thr
            115                 120                 125

Thr Ile Val Asp Lys Leu Ile Glu Met Thr Asp Gly Gly Cys Asp Tyr
130                 135                 140

Thr Phe Asp Cys Thr Gly Asn Val Asn Val Met Arg Asn Ala Leu Glu
145                 150                 155                 160

Ala Cys His Lys Gly Trp Gly Thr Ser Ile Ile Gly Val Ala Ala
            165                 170                 175

Ala Gly Lys Glu Ile Ser Thr Arg Pro Phe Gln Leu Val Thr Gly Arg
            180                 185                 190

Val Trp Lys Gly Ala Ala Phe Gly Gly Val Lys Gly Arg Ser Gln Leu
            195                 200                 205

Pro Gly Ile Val Glu Asp Tyr Leu Asp Gly Lys Leu Lys Val Glu Glu
            210                 215                 220

Phe Ile Thr His Arg Glu Pro Leu Asp Lys Ile Asn Thr Ala Phe Asp
225                 230                 235                 240

Glu Met His Gly Gly Asp Cys Ile Arg Ala Val Val Ser Leu Trp
            245                 250                 255

<210> SEQ ID NO 37
<211> LENGTH: 768
<212> TYPE: DNA
<213> ORGANISM: Artificial sequence
<220> FEATURE:
<223> OTHER INFORMATION: Synthetic polynucleotide

<400> SEQUENCE: 37
atgccggacg gtacgccgcg cttcacctgt aaaggcaaag aaatcctgca cttcatgggc      60
tgtagcacgt tcagtcaata tacggttgtt gcagacatca gcgtggttgc catcaacgaa     120
aaagcagaat tcgaaaaagc ttgcctgctg ggttgtggca tcaccacggg ttatggcgcg     180
gccaccatta cggcgaacgt gcaggaaggt gataatgttg cggtgtttgg cggtggctgc     240
gtgggtctga gtgttatcca aggctgtaaa gaacgtaaag ttaacaaaat catcctggtc     300
gatattaatg acaagaaaga agaatggggt aaacagtttg gcgccaccga cttcgttaac     360
tccacgaaac tgccggaagg taccacgatc gtggataaac tgattgaaat gaccgatggt     420
ggctgcgact atacctttga ttgtacgggc aacgttaatg tcatgcgcaa tgctctggaa     480
gcgtgccata aaggttgggg caccagcatt atcattggtg tggcagctgc gggcaaagaa     540
atctctaccc gtccgtttca gctggtcacc ggtcgtgtgt ggaaaggtgc agcattcggt     600
ggcgtgaaag tcgtagcca actgccgggc attgttgaag attacctgga cggcaaactg     660
aaagtcgaag aattcatcac ccaccgcgaa ccgctggata aaattaatac ggcgtttgat     720
gaaatgcacg gtggtgattg tatccgcgca gtcgttagcc tgtggtaa                  768

<210> SEQ ID NO 38
<211> LENGTH: 2103
<212> TYPE: DNA
<213> ORGANISM: Yarrowia lipolytica
<220> FEATURE:
<221> NAME/KEY: misc_feature
<223> OTHER INFORMATION: acyl-coenzyme A oxidase POX2
```

<400> SEQUENCE: 38

```
atgaacccca acaacactgg caccattgaa atcaacggta aggagtacaa caccttcacc      60
gagcccccg tggccatggc tcaggagcga gccaagacct ccttcccgt gcgagagatg       120
acctacttcc tcgacggtgg cgagaagaac accctcaaaa acgagcagat catggaggag     180
attgagcgag accctctttt caacaacgac aactactacg atctcaacaa ggagcagatc     240
cgagagctca ccatggagcg agtcgccaag ctgtctctgt tgtgcgtga tcagcccgag      300
gacgacatca agaagcgatt tgctctcatt ggtatcgccg atatgggaac ctacacccga     360
cttggtgtcc actacggcct cttctttggc gccgtccgag gtaccggaac tgccgagcag     420
tttggccact ggatctccaa gggagccgga gacctgcgaa agttctacgg atgtttctcc     480
atgaccgagc tgggccatgg ctccaacctg gctggtctcg agaccaccgc catctacgat     540
gaggagaccg acgagttcat catcaacacc cctcacattg ccgccaccaa gtggtggatt     600
ggaggagccg cccacaccgc cacccacact gtcgtgttcg cccgactcat tgtcaagggc     660
aaggactacg gtgtcaagac ctttgttgtc cagctgcgaa acatcaacga ccacagcctc     720
aaggtcggta tctctattgg tgatatcgga agaagatgg gccgagacgg tatcgataac      780
ggatggatcc agttccaccaa cgtgcgaatc ccccgacaga acctgctcat gaagtacaca    840
aaggtcgacc gagagggtaa cgtgacccag cctcctctgg ctcagcttac ctacggttct    900
cttatcactg tcgagtctc catggcctct gattctcacc aggtcggaaa gcgattcatc     960
accattgctc tgcgatacgc ctgcattcga cgacagttct ccaccacccc cggccagccc   1020
gagaccaaga tcatcgacta ccctaccat cagcgacgac ttctgcctct tctggcctat     1080
gtctatgctc ttaagatgac tgccgatgag gttggagctc tcttctcccg aaccatgctt   1140
aagatggacg acctcaagcc cgacgacaag gccggcctca tgaggttgt ttccgacgtc    1200
aaggagctct ctccgtctc cgccggtctc aaggccttct ccacctgggc ttgtgccgac    1260
gtcattgaca agacccgaca ggcttgcggt ggccacggtt actctggata caacggtttc    1320
ggccaggcct acgccgactg ggttgtccag tgcacctggg agggtgacaa caacattctc    1380
accctttctg ccgccgagc tcttatccag tctgccgttg ctctgcgaaa gggcgagcct    1440
gttggtaacg ccgtttctta cctgaagcga tacaaggatc tggccaacgc taagctcaat   1500
ggccgatctc tcaccgaccc caaggtcctc gtcgaggcct gggaggttgc tgccggtaac   1560
atcatcaacc gagccaccga ccagtacgag aagctcattg gcgagggtct taacgccgac   1620
caggcctttg aggttctgtc tcagcagcga ttccaggccg ccaaggtcca cacgacga     1680
cacctcattg ccgctttctt ctcccgaatt gacaccgagg ctggcgaggc catcaagcag   1740
cccctgctta acctggctct gctgtttgcc ctgtggtcca tcgaagagga ctctggtctg   1800
ttcctgcgag agggcttcct cgagcccaag gatatcgaca ccgtcaccga gctcgtcaac    1860
aagtactgca ccactgtgcg agaggaggtc attggctaca ccgatgcctt caacctgtcc   1920
gactacttca tcaacgctcc tattggatgc tacgatggtg acgcttaccg acactacttc   1980
cagaaggtca acgagcagaa ccctgcccga ccccgac ctccttacta cgcctctact      2040
ctcaagccct ccttttccg agaggaggag gatgatgaca tttgcgagct tgatgaggaa    2100
tag                                                                  2103
```

<210> SEQ ID NO 39
<211> LENGTH: 700
<212> TYPE: PRT
<213> ORGANISM: Yarrowia lipolytica

```
<220> FEATURE:
<221> NAME/KEY: MISC_FEATURE
<223> OTHER INFORMATION: acyl-coenzyme A oxidase POX2

<400> SEQUENCE: 39
```

| | | | | | | | | | | | | | | |
|---|---|---|---|---|---|---|---|---|---|---|---|---|---|---|
| Met | Asn | Pro | Asn | Asn | Thr | Gly | Thr | Ile | Glu | Ile | Asn | Gly | Lys | Glu | Tyr |
| 1 | | | | 5 | | | | | 10 | | | | | 15 | |
| Asn | Thr | Phe | Thr | Glu | Pro | Pro | Val | Ala | Met | Ala | Gln | Glu | Arg | Ala | Lys |
| | | | 20 | | | | | 25 | | | | | 30 | | |
| Thr | Ser | Phe | Pro | Val | Arg | Glu | Met | Thr | Tyr | Phe | Leu | Asp | Gly | Gly | Glu |
| | | 35 | | | | | 40 | | | | | 45 | | | |
| Lys | Asn | Thr | Leu | Lys | Asn | Glu | Gln | Ile | Met | Glu | Glu | Ile | Glu | Arg | Asp |
| | 50 | | | | | 55 | | | | | 60 | | | | |
| Pro | Leu | Phe | Asn | Asn | Asp | Asn | Tyr | Tyr | Asp | Leu | Asn | Lys | Glu | Gln | Ile |
| 65 | | | | | 70 | | | | | 75 | | | | | 80 |
| Arg | Glu | Leu | Thr | Met | Glu | Arg | Val | Ala | Lys | Leu | Ser | Leu | Phe | Val | Arg |
| | | | | 85 | | | | | 90 | | | | | 95 | |
| Asp | Gln | Pro | Glu | Asp | Asp | Ile | Lys | Lys | Arg | Phe | Ala | Leu | Ile | Gly | Ile |
| | | | 100 | | | | | 105 | | | | | 110 | | |
| Ala | Asp | Met | Gly | Thr | Tyr | Thr | Arg | Leu | Gly | Val | His | Tyr | Gly | Leu | Phe |
| | | 115 | | | | | 120 | | | | | 125 | | | |
| Phe | Gly | Ala | Val | Arg | Gly | Thr | Gly | Thr | Ala | Glu | Gln | Phe | Gly | His | Trp |
| | 130 | | | | | 135 | | | | | 140 | | | | |
| Ile | Ser | Lys | Gly | Ala | Gly | Asp | Leu | Arg | Lys | Phe | Tyr | Gly | Cys | Phe | Ser |
| 145 | | | | | 150 | | | | | 155 | | | | | 160 |
| Met | Thr | Glu | Leu | Gly | His | Gly | Ser | Asn | Leu | Ala | Gly | Leu | Glu | Thr | Thr |
| | | | | 165 | | | | | 170 | | | | | 175 | |
| Ala | Ile | Tyr | Asp | Glu | Glu | Thr | Asp | Glu | Phe | Ile | Ile | Asn | Thr | Pro | His |
| | | | 180 | | | | | 185 | | | | | 190 | | |
| Ile | Ala | Ala | Thr | Lys | Trp | Trp | Ile | Gly | Gly | Ala | Ala | His | Thr | Ala | Thr |
| | | 195 | | | | | 200 | | | | | 205 | | | |
| His | Thr | Val | Val | Phe | Ala | Arg | Leu | Ile | Val | Lys | Gly | Lys | Asp | Tyr | Gly |
| | 210 | | | | | 215 | | | | | 220 | | | | |
| Val | Lys | Thr | Phe | Val | Val | Gln | Leu | Arg | Asn | Ile | Asn | Asp | His | Ser | Leu |
| 225 | | | | | 230 | | | | | 235 | | | | | 240 |
| Lys | Val | Gly | Ile | Ser | Ile | Gly | Asp | Ile | Gly | Lys | Lys | Met | Gly | Arg | Asp |
| | | | | 245 | | | | | 250 | | | | | 255 | |
| Gly | Ile | Asp | Asn | Gly | Trp | Ile | Gln | Phe | Thr | Asn | Val | Arg | Ile | Pro | Arg |
| | | | 260 | | | | | 265 | | | | | 270 | | |
| Gln | Asn | Leu | Leu | Met | Lys | Tyr | Thr | Lys | Val | Asp | Arg | Glu | Gly | Asn | Val |
| | | 275 | | | | | 280 | | | | | 285 | | | |
| Thr | Gln | Pro | Pro | Leu | Ala | Gln | Leu | Thr | Tyr | Gly | Ser | Leu | Ile | Thr | Gly |
| | 290 | | | | | 295 | | | | | 300 | | | | |
| Arg | Val | Ser | Met | Ala | Ser | Asp | Ser | His | Gln | Val | Gly | Lys | Arg | Phe | Ile |
| 305 | | | | | 310 | | | | | 315 | | | | | 320 |
| Thr | Ile | Ala | Leu | Arg | Tyr | Ala | Cys | Ile | Arg | Arg | Gln | Phe | Ser | Thr | Thr |
| | | | | 325 | | | | | 330 | | | | | 335 | |
| Pro | Gly | Gln | Pro | Glu | Thr | Lys | Ile | Ile | Asp | Tyr | Pro | Tyr | His | Gln | Arg |
| | | | 340 | | | | | 345 | | | | | 350 | | |
| Arg | Leu | Leu | Pro | Leu | Leu | Ala | Tyr | Val | Tyr | Ala | Leu | Lys | Met | Thr | Ala |
| | | 355 | | | | | 360 | | | | | 365 | | | |
| Asp | Glu | Val | Gly | Ala | Leu | Phe | Ser | Arg | Thr | Met | Leu | Lys | Met | Asp | Asp |
| | 370 | | | | | 375 | | | | | 380 | | | | |
| Leu | Lys | Pro | Asp | Asp | Lys | Ala | Gly | Leu | Asn | Glu | Val | Val | Ser | Asp | Val |

```
                385                 390                 395                 400
Lys Glu Leu Phe Ser Val Ser Ala Gly Leu Lys Ala Phe Ser Thr Trp
                    405                 410                 415

Ala Cys Ala Asp Val Ile Asp Lys Thr Arg Gln Ala Cys Gly Gly His
                420                 425                 430

Gly Tyr Ser Gly Tyr Asn Gly Phe Gly Gln Ala Tyr Ala Asp Trp Val
            435                 440                 445

Val Gln Cys Thr Trp Glu Gly Asp Asn Asn Ile Leu Thr Leu Ser Ala
    450                 455                 460

Gly Arg Ala Leu Ile Gln Ser Ala Val Ala Leu Arg Lys Gly Glu Pro
465                 470                 475                 480

Val Gly Asn Ala Val Ser Tyr Leu Lys Arg Tyr Lys Asp Leu Ala Asn
                485                 490                 495

Ala Lys Leu Asn Gly Arg Ser Leu Thr Asp Pro Lys Val Leu Val Glu
                500                 505                 510

Ala Trp Glu Val Ala Ala Gly Asn Ile Ile Asn Arg Ala Thr Asp Gln
            515                 520                 525

Tyr Glu Lys Leu Ile Gly Glu Gly Leu Asn Ala Asp Gln Ala Phe Glu
    530                 535                 540

Val Leu Ser Gln Gln Arg Phe Gln Ala Ala Lys Val His Thr Arg Arg
545                 550                 555                 560

His Leu Ile Ala Ala Phe Phe Ser Arg Ile Asp Thr Glu Ala Gly Glu
                565                 570                 575

Ala Ile Lys Gln Pro Leu Leu Asn Leu Ala Leu Leu Phe Ala Leu Trp
                580                 585                 590

Ser Ile Glu Glu Asp Ser Gly Leu Phe Leu Arg Glu Gly Phe Leu Glu
            595                 600                 605

Pro Lys Asp Ile Asp Thr Val Thr Glu Leu Val Asn Lys Tyr Cys Thr
    610                 615                 620

Thr Val Arg Glu Glu Val Ile Gly Tyr Thr Asp Ala Phe Asn Leu Ser
625                 630                 635                 640

Asp Tyr Phe Ile Asn Ala Pro Ile Gly Cys Tyr Asp Gly Asp Ala Tyr
                645                 650                 655

Arg His Tyr Phe Gln Lys Val Asn Glu Gln Asn Pro Ala Arg Asp Pro
                660                 665                 670

Arg Pro Pro Tyr Tyr Ala Ser Thr Leu Lys Pro Phe Leu Phe Arg Glu
    675                 680                 685

Glu Glu Asp Asp Asp Ile Cys Glu Leu Asp Glu Glu
690                 695                 700

<210> SEQ ID NO 40
<211> LENGTH: 2100
<212> TYPE: DNA
<213> ORGANISM: Yarrowia lipolytica
<220> FEATURE:
<221> NAME/KEY: misc_feature
<223> OTHER INFORMATION: acyl-coenzyme A oxidase POX 5

<400> SEQUENCE: 40
atgaacaaca accccaccaa cgtgatcctt ggaggcaagg agtacgacac cttcaccgag      60
cctccggccc agatggagct ggagcgagcc aagacacaat tcaaggtccg agacgtgacc     120
aacttcctca caggcagcga gcaggagaca ctgctgaccg agcgaatcat gcgggagatt     180
gagcgagatc ccgttctcaa cgtcgccggc gactacgacg ccgatcttcc caccaagcga     240
cgacaagctg ttgagcgaat cggggctctg gcccgatacc tgcccaagga ttccgagaag     300
```

```
gaggccattt tgcgaggcca gctgcatggt attgtggaca tgggtacccg aacccgaatc    360
gccgttcact acggtctgtt tatgggcgcc attcgtggct caggaaccaa ggagcagtac    420
gattactggg tcgccaaggg cgccgctact ctgcacaaat tctatggctg ctttgccatg    480
actgagctgg tcacggatc taacgtggcc ggtctcgaga ccaccgccac ccttgataag    540
gacaccgacg agttcatcat caacaccccc aactcgggag ccacaaagtg gtggattgga    600
ggagctgccc actctgctac ccacacggct tgtcttgccc gactcattgt tgatggcaag    660
gactatggtg ttaagatctt cattgttcag ctgcgagacc tcaactccca ctctctactc    720
aacggtattg ccattggaga tatcggcaag aagatgggcc gagatgccat tgataatggt    780
tggatccagt tcacagacgt ccgaattccc cgacagaaca tgctcatgcg atacgaccgg    840
gtgtctcgag acggcgaggt taccacctcc gagcttgccc agctcaccta cggagcactt    900
ctgtctggcc gagtgaccat gattgccgag tctcacctcc tgtctgctcg gttcctcacc    960
attgctcttc ggtacgcctg tatccgtcga cagttcggag ctgtgcctga caagcccgag   1020
actaagctca tcgactaccc ctaccaccaa cgacgtctgc tgcctcttct ggcctacacc   1080
tacgccatga agatgggcgc cgacgaggcc cagcagcagt acaactcctc ctttggcgct   1140
cttctcaagc tcaaccccgt caaggacgct gagaagtttg ctgtcgccac tgccgacctc   1200
aaggctctgt ttgcctcttc tgccggaatg aaggccttca ccacctgggc tgccgccaag   1260
atcattgacg agtgccgaca ggcctgtggt ggccatggct actccggcta caacggtttc   1320
ggtcaggctt acgccgactg ggtcgtccaa tgcacttggg agggtgacaa caacgtgctg   1380
tgtctgtcca tgggtcgatc gctcatccag tcgtgcattg ccatgagaaa gaagaagggc   1440
catgtcggca gtcggtcga gtacctgcag cgacgagacg agctgcagaa tgcccgagtt   1500
gacaacaagc ctctcactga ccctgctgtg ctcatcactg catgggagaa ggttgcctgc   1560
gaggccatca acagagccac tgactccttc atcaagctca cccaggaggg tctgtctcct   1620
gaccaggcct ttgaggagct gtctcaacag agatttgagt gtgcgcgaat ccacacccga   1680
aagcatctga tcacctcgtt ctacgctcga atctccaagg ccaaggcccg agtcaagccc   1740
caccttactg ttcttgccaa cctctttgcc gtctggtcca tcgaggagga ctctggtctc   1800
ttccttcggg agggctgctt cgagcctgcc gagatggacg agatcaccgc tctggtcgac   1860
gagctgtgct gcgaggctcg agagcaggtc attggattca ccgacgcctt caacctgtcc   1920
gacttcttca ttaacgcccc cattggccga ttcgacggag acgcctacaa gcactacatg   1980
gacgaggtca aggctgccaa caaccctcgt aacacccatg ctccttacta cgagaccaag   2040
ctgcgaccct tcctgttccg acccgatgag gacgaggaga tttgcgacct ggacgagtag   2100
```

<210> SEQ ID NO 41
<211> LENGTH: 699
<212> TYPE: PRT
<213> ORGANISM: Yarrowia lipolytica
<220> FEATURE:
<221> NAME/KEY: MISC_FEATURE
<223> OTHER INFORMATION: acyl-coenzyme A oxidase POX5

<400> SEQUENCE: 41

Met Asn Asn Asn Pro Thr Asn Val Ile Leu Gly Gly Lys Glu Tyr Asp
1               5                   10                  15

Thr Phe Thr Glu Pro Pro Ala Gln Met Glu Leu Glu Arg Ala Lys Thr
            20                  25                  30

Gln Phe Lys Val Arg Asp Val Thr Asn Phe Leu Thr Gly Ser Glu Gln

-continued

```
                35                  40                  45
Glu Thr Leu Leu Thr Glu Arg Ile Met Arg Glu Ile Glu Arg Asp Pro
 50                  55                  60

Val Leu Asn Val Ala Gly Asp Tyr Asp Ala Asp Leu Pro Thr Lys Arg
 65                  70                  75                  80

Arg Gln Ala Val Glu Arg Ile Gly Ala Leu Ala Arg Tyr Leu Pro Lys
                 85                  90                  95

Asp Ser Glu Lys Glu Ala Ile Leu Arg Gly Gln Leu His Gly Ile Val
                100                 105                 110

Asp Met Gly Thr Arg Thr Arg Ile Ala Val His Tyr Gly Leu Phe Met
                115                 120                 125

Gly Ala Ile Arg Gly Ser Gly Thr Lys Glu Gln Tyr Asp Tyr Trp Val
                130                 135                 140

Ala Lys Gly Ala Ala Thr Leu His Lys Phe Tyr Gly Cys Phe Ala Met
145                 150                 155                 160

Thr Glu Leu Gly His Gly Ser Asn Val Ala Gly Leu Glu Thr Thr Ala
                165                 170                 175

Thr Leu Asp Lys Asp Thr Asp Glu Phe Ile Ile Asn Thr Pro Asn Ser
                180                 185                 190

Gly Ala Thr Lys Trp Trp Ile Gly Gly Ala Ala His Ser Ala Thr His
                195                 200                 205

Thr Ala Cys Leu Ala Arg Leu Ile Val Asp Gly Lys Asp Tyr Gly Val
210                 215                 220

Lys Ile Phe Ile Val Gln Leu Arg Asp Leu Asn Ser His Ser Leu Leu
225                 230                 235                 240

Asn Gly Ile Ala Ile Gly Asp Ile Gly Lys Lys Met Gly Arg Asp Ala
                245                 250                 255

Ile Asp Asn Gly Trp Ile Gln Phe Thr Asp Val Arg Ile Pro Arg Gln
                260                 265                 270

Asn Met Leu Met Arg Tyr Asp Arg Val Ser Arg Asp Gly Glu Val Thr
                275                 280                 285

Thr Ser Glu Leu Ala Gln Leu Thr Tyr Gly Ala Leu Leu Ser Gly Arg
                290                 295                 300

Val Thr Met Ile Ala Glu Ser His Leu Leu Ser Ala Arg Phe Leu Thr
305                 310                 315                 320

Ile Ala Leu Arg Tyr Ala Cys Ile Arg Arg Gln Phe Gly Ala Val Pro
                325                 330                 335

Asp Lys Pro Glu Thr Lys Leu Ile Asp Tyr Pro Tyr His Gln Arg Arg
                340                 345                 350

Leu Leu Pro Leu Leu Ala Tyr Thr Tyr Ala Met Lys Met Gly Ala Asp
                355                 360                 365

Glu Ala Gln Gln Gln Tyr Asn Ser Ser Phe Gly Ala Leu Leu Lys Leu
                370                 375                 380

Asn Pro Val Lys Asp Ala Glu Lys Phe Ala Val Ala Thr Ala Asp Leu
385                 390                 395                 400

Lys Ala Leu Phe Ala Ser Ser Ala Gly Met Lys Ala Phe Thr Thr Trp
                405                 410                 415

Ala Ala Ala Lys Ile Ile Asp Glu Cys Arg Gln Ala Cys Gly Gly His
                420                 425                 430

Gly Tyr Ser Gly Tyr Asn Gly Phe Gly Gln Ala Tyr Ala Asp Trp Val
                435                 440                 445

Val Gln Cys Thr Trp Glu Gly Asp Asn Asn Val Leu Cys Leu Ser Met
                450                 455                 460
```

Gly Arg Ser Leu Ile Gln Ser Cys Ile Ala Met Arg Lys Lys Gly
465                 470                 475                 480

His Val Gly Lys Ser Val Glu Tyr Leu Gln Arg Arg Asp Glu Leu Gln
            485                 490                 495

Asn Ala Arg Val Asp Asn Lys Pro Leu Thr Asp Pro Val Leu Ile
        500                 505                 510

Thr Ala Trp Glu Lys Val Ala Cys Glu Ala Ile Asn Arg Ala Thr Asp
    515                 520                 525

Ser Phe Ile Lys Leu Thr Gln Glu Gly Leu Ser Pro Asp Gln Ala Phe
    530                 535                 540

Glu Glu Leu Ser Gln Gln Arg Phe Glu Cys Ala Arg Ile His Thr Arg
545                 550                 555                 560

Lys His Leu Ile Thr Ser Phe Tyr Ala Arg Ile Ser Lys Ala Lys Ala
                565                 570                 575

Arg Val Lys Pro His Leu Thr Val Leu Ala Asn Leu Phe Ala Val Trp
            580                 585                 590

Ser Ile Glu Glu Asp Ser Gly Leu Phe Leu Arg Glu Gly Cys Phe Glu
        595                 600                 605

Pro Ala Glu Met Asp Glu Ile Thr Ala Leu Val Asp Glu Leu Cys Cys
    610                 615                 620

Glu Ala Arg Glu Gln Val Ile Gly Phe Thr Asp Ala Phe Asn Leu Ser
625                 630                 635                 640

Asp Phe Phe Ile Asn Ala Pro Ile Gly Arg Phe Asp Gly Asp Ala Tyr
                645                 650                 655

Lys His Tyr Met Asp Glu Val Lys Ala Ala Asn Pro Arg Asn Thr
            660                 665                 670

His Ala Pro Tyr Tyr Glu Thr Lys Leu Arg Pro Phe Leu Phe Arg Pro
        675                 680                 685

Asp Glu Asp Glu Glu Ile Cys Asp Leu Asp Glu
    690                 695

<210> SEQ ID NO 42
<211> LENGTH: 1752
<212> TYPE: DNA
<213> ORGANISM: Escherichia coli
<220> FEATURE:
<221> NAME/KEY: misc_feature
<223> OTHER INFORMATION: acyl-coenzyme A oxidase, FadD

<400> SEQUENCE: 42
atgttaacag tatgtttatc acttggggtt gcgatgacga cgaacgcgca ttttagaggt        60
gaagaattga agaaggtttg gcttaaccgt tatcccgcgg acgttccgac ggagatcaac       120
cctgaccgtt atcaatctct ggtagatatg tttgagcagt cggtcgcgcg ctacgccgat       180
caacccgcgt ttgtgaatat gggggaggtg atgaccttcc gcaaactgga gaacgcagt       240 cgcgcgtttg ccgcttattt gcaacaaggg ttggggctga agaaggcga tcgcgttgcg       300 ttgatgatgc taacttatt gcaatatccg gtggcgctgt ttggcatttt gcgtgccggg       360
atgatcgtcg taaacgttaa cccgttgtat accccgcgtg agcttgagca tcagcttaac       420
gatagcggcg catcggcgat tgttatcgtg tctaactttg cccacactct ggaaaaagtg       480
gttgataaaa ccgccgttca gcacgttatt ctgacccgta tgggcgatca gctatctacg       540
gcaaaaggca cggtagtcaa tttcgttgtt aaatacatca agcgtctggt gccgaaatac       600
catctgccag atgccatttc atttcgtagc gccctgcaca acggctaccg gatgcagtac       660

-continued

```
gtcaaaccag aactggtgcc ggaagattta gctttcctgc aatacaccgg cggcaccact    720
ggtgtggcga aggcgcgat  gctgactcac cgcaatatgc tggcgaacct ggaacaggtt    780
aacgcgacct atggtccgct gttgcatccg ggcaaagagc tggtggtgac ggcgctgccg    840
ctgtatcaca tttttgcact gaccattaac tgcctgctgt ttatcgaact gggggggcag    900
aacctgctta tcactaaccc cgcgcgatatt ccagggctgg taaaagagtt agcgaaatat   960
ccgtttaccg ctatcactgg cgttaacacc ttgttcaatg cgttgctgaa caataaagag   1020
ttccagcagc tggatttctc cagtctgcat ctttccgcag gcggtgggat gcctgttcag   1080
caagtggttg cagaacgttg ggttaaactg actggacagt atctgctgga aggttatggc   1140
ctgaccgagt gcgcgccgct ggtcagcgtt aacccgtatg atattgatta tcatagtggt   1200
agcatcggtt taccggtgcc gtcgacggaa gccaaactgg tggatgatga tgataatgaa   1260
gtaccacctg gtcaaccagg tgagctttgt gtcaaaggac cgcaggtgat gctgggttac   1320
tggcagcgtc cggatgctac cgatgaaatc atcaaaaatg ctggttaca  caccggcgac   1380
atcgcggtga tggatgaaga aggattcctg cgcattgtcg atcgtaaaaa agacatgatt   1440
ctggtttccg gttttaacgt ttatcccaac gagattgaag atgtcgtcat gcagcatcct   1500
ggcgtacagg aagtcgcggc tgttggcgta ccttccggct ccagtggtga agcggtgaaa   1560
atcttcgtag tgaaaaaga tccatcgctt accgaagagt cactggtgac cttttgccgc   1620
cgtcagctca cgggctacaa agtaccgaag ctggtggagt ttcgtgatga gttaccgaaa   1680
tctaacgtcg gaaaaatttt gcgacgagaa ttacgtgacg aagcgcgcgg caaagtggac   1740
aataaagcct ga                                                       1752
```

<210> SEQ ID NO 43
<211> LENGTH: 583
<212> TYPE: PRT
<213> ORGANISM: Escherichia coli
<220> FEATURE:
<221> NAME/KEY: MISC_FEATURE
<223> OTHER INFORMATION: acyl-coenzyme A oxidase, FadD

<400> SEQUENCE: 43

```
Met Leu Thr Val Cys Leu Ser Leu Gly Val Ala Met Thr Thr Asn Ala
1               5                   10                  15

His Phe Arg Gly Glu Glu Leu Lys Lys Val Trp Leu Asn Arg Tyr Pro
            20                  25                  30

Ala Asp Val Pro Thr Glu Ile Asn Pro Asp Arg Tyr Gln Ser Leu Val
        35                  40                  45

Asp Met Phe Glu Gln Ser Val Ala Arg Tyr Ala Asp Gln Pro Ala Phe
    50                  55                  60

Val Asn Met Gly Glu Val Met Thr Phe Arg Lys Leu Glu Glu Arg Ser
65                  70                  75                  80

Arg Ala Phe Ala Ala Tyr Leu Gln Gln Gly Leu Gly Leu Lys Lys Gly
                85                  90                  95

Asp Arg Val Ala Leu Met Met Pro Asn Leu Leu Gln Tyr Pro Val Ala
            100                 105                 110

Leu Phe Gly Ile Leu Arg Ala Gly Met Ile Val Val Asn Val Asn Pro
        115                 120                 125

Leu Tyr Thr Pro Arg Glu Leu Glu His Gln Leu Asn Asp Ser Gly Ala
    130                 135                 140

Ser Ala Ile Val Ile Val Ser Asn Phe Ala His Thr Leu Glu Lys Val
145                 150                 155                 160
```

-continued

Val Asp Lys Thr Ala Val Gln His Val Ile Leu Thr Arg Met Gly Asp
            165                 170                 175
Gln Leu Ser Thr Ala Lys Gly Thr Val Asn Phe Val Lys Tyr
        180                 185                 190
Ile Lys Arg Leu Val Pro Lys Tyr His Leu Pro Asp Ala Ile Ser Phe
        195                 200                 205
Arg Ser Ala Leu His Asn Gly Tyr Arg Met Gln Tyr Val Lys Pro Glu
    210                 215                 220
Leu Val Pro Glu Asp Leu Ala Phe Leu Gln Tyr Thr Gly Gly Thr Thr
225                 230                 235                 240
Gly Val Ala Lys Gly Ala Met Leu Thr His Arg Asn Met Leu Ala Asn
                245                 250                 255
Leu Glu Gln Val Asn Ala Thr Tyr Gly Pro Leu Leu His Pro Gly Lys
        260                 265                 270
Glu Leu Val Val Thr Ala Leu Pro Leu Tyr His Ile Phe Ala Leu Thr
        275                 280                 285
Ile Asn Cys Leu Leu Phe Ile Glu Leu Gly Gly Gln Asn Leu Leu Ile
        290                 295                 300
Thr Asn Pro Arg Asp Ile Pro Gly Leu Val Lys Glu Leu Ala Lys Tyr
305                 310                 315                 320
Pro Phe Thr Ala Ile Thr Gly Val Asn Thr Leu Phe Asn Ala Leu Leu
                325                 330                 335
Asn Asn Lys Glu Phe Gln Gln Leu Asp Phe Ser Ser Leu His Leu Ser
            340                 345                 350
Ala Gly Gly Gly Met Pro Val Gln Gln Val Val Ala Glu Arg Trp Val
            355                 360                 365
Lys Leu Thr Gly Gln Tyr Leu Leu Glu Gly Tyr Gly Leu Thr Glu Cys
    370                 375                 380
Ala Pro Leu Val Ser Val Asn Pro Tyr Asp Ile Asp Tyr His Ser Gly
385                 390                 395                 400
Ser Ile Gly Leu Pro Val Pro Ser Thr Glu Ala Lys Leu Val Asp Asp
                405                 410                 415
Asp Asp Asn Glu Val Pro Pro Gly Gln Pro Gly Glu Leu Cys Val Lys
            420                 425                 430
Gly Pro Gln Val Met Leu Gly Tyr Trp Gln Arg Pro Asp Ala Thr Asp
            435                 440                 445
Glu Ile Ile Lys Asn Gly Trp Leu His Thr Gly Asp Ile Ala Val Met
    450                 455                 460
Asp Glu Glu Gly Phe Leu Arg Ile Val Asp Arg Lys Lys Asp Met Ile
465                 470                 475                 480
Leu Val Ser Gly Phe Asn Val Tyr Pro Asn Glu Ile Glu Asp Val Val
                485                 490                 495
Met Gln His Pro Gly Val Gln Glu Val Ala Ala Val Gly Val Pro Ser
            500                 505                 510
Gly Ser Ser Gly Glu Ala Val Lys Ile Phe Val Val Lys Lys Asp Pro
            515                 520                 525
Ser Leu Thr Glu Glu Ser Leu Val Thr Phe Cys Arg Arg Gln Leu Thr
    530                 535                 540
Gly Tyr Lys Val Pro Lys Leu Val Glu Phe Arg Asp Glu Leu Pro Lys
545                 550                 555                 560
Ser Asn Val Gly Lys Ile Leu Arg Arg Glu Leu Arg Asp Glu Ala Arg
                565                 570                 575
Gly Lys Val Asp Asn Lys Ala

<210> SEQ ID NO 44
<211> LENGTH: 1959
<212> TYPE: DNA
<213> ORGANISM: Escherichia coli
<220> FEATURE:
<221> NAME/KEY: misc_feature
<223> OTHER INFORMATION: Adenosine monophosphate (AMP)-forming acetyl-CoA synthetase

<400> SEQUENCE: 44

```
atgagccaaa ttcacaaaca caccattcct gccaacatcg cagaccgttg cctgataaac      60
cctcagcagt acgaggcgat gtatcaacaa tctattaacg tacctgatac cttctggggc     120
gaacagggaa aaattcttga ctggatcaaa ccttaccaga aggtgaaaaa cacctccttt     180
gcccccggta atgtgtccat aaatggtac gaggacggca cgctgaatct gcggcaaac      240
tgccttgacc gccatctgca agaaaacggc gatcgtaccg ccatcatctg ggaaggcgac     300
gacgccagcc agagcaaaca tatcagctat aaagagctgc accgcgacgt ctgccgcttc     360
gccaataccc tgctcgagct gggcattaaa aaggtgatg tggtggcgat ttatatgccg     420
atggtgccgg aagccgcggt tgcgatgctg gcctgcgccc gcattggcgc ggtgcattcg     480
gtgatttcg cggcttctc gccggaagcc gttgccgggc gcattattga ttccaactca     540
cgactggtga tcacttccga cgaaggtgtg cgtgccgggc gcagtattcc gctgaagaaa     600
aacgttgatg acgcgctgaa aaacccgaac gtcaccagcg tagagcatgt ggtggtactg     660
aagcgtactg gcgggaaaat tgactggcag gaagggcgcg acctgtggtg gcacgacctg     720
gttgagcaag cgagcgatca gcaccaggcg gaagagatga acgccgaaga tccgctgttt     780
attctctaca cctccggttc taccggtaag ccaaaaggtg tgctgcatac taccggcggt     840
tatctggtgt acgcggcgct gaccttaaa tatgtctttg attatcatcc gggtgatatc     900
tactggtgca ccgccgatgt gggctgggtg accggacaca gttacttgct gtacggcccg     960
ctggcctgcg gtgcgaccac gctgatgttt gaaggcgtac cgaactggcc gacgcctgcc    1020
cgtatggcgc aggtggtgga caagcatcag gtcaatattc tctataccgc gcccacgcg     1080
attcgcgcgc tgatggcgga aggggataaa gcgattgaag caccgaccg atcgtcgctg    1140
cgcattctcg gttccgtggg cgagccaatc aacccggaag cgtgggagtg gtactggaaa    1200
aaaatcggca acgagaaatg tccggtggtc gatacctggt ggcagaccga actggcggt     1260
ttcatgatca cgccgctgcc tggcgctacc gagctgaaag ccggttcggc aacacgtccg    1320
ttcttcggcg tgcaaccggc gctggtcgat aacgaaggta cccgctgga aggcgctacc     1380
gaaggcagcc tggtgatcac cgactcctgg ccgggtcagg cgcgtacgct gtttggcgat    1440
cacgaacgtt ttgaacagac ctacttctcc accttcaaaa atatgtattt cagcggcgac    1500
ggcgcgcgtc gcgatgaaga tggctattac tggataaccg gcgtgtgga cgatgtgctg    1560
aacgtctccg gtcaccgtct gggaacggcg gagattgagt cggcgctggt ggcgcatccg    1620
aagattgccg aagccgccgt agtaggtatt ccgcacaata ttaaaggtca ggcgatctac    1680
gcctacgtca cgcttaatca cggggaggaa ccgtcaccag aactgtacgc agaagtccgc    1740
aactgggtgc gtaaagagat tggcccgctg gcgacgccag acgtgctgca ctggaccgac    1800
tccctgccta aaacccgctc cggcaaaatt atgcgccgta ttctgcgcaa aattgcggcg    1860
ggcgatacca gcaacctggg cgatacctcg acgcttgccg atcctggcgt agtcgagaag    1920
ctgcttgaag agaagcaggc tatcgcgatg ccatcgtaa                           1959
```

<210> SEQ ID NO 45
<211> LENGTH: 652
<212> TYPE: PRT
<213> ORGANISM: Escherichia coli
<220> FEATURE:
<221> NAME/KEY: MISC_FEATURE
<223> OTHER INFORMATION: Adenosine monophosphate (AMP)-forming acetyl-CoA synthetase

<400> SEQUENCE: 45

```
Met Ser Gln Ile His Lys His Thr Ile Pro Ala Asn Ile Ala Asp Arg
1               5                   10                  15

Cys Leu Ile Asn Pro Gln Gln Tyr Glu Ala Met Tyr Gln Gln Ser Ile
            20                  25                  30

Asn Val Pro Asp Thr Phe Trp Gly Glu Gln Gly Lys Ile Leu Asp Trp
        35                  40                  45

Ile Lys Pro Tyr Gln Lys Val Lys Asn Thr Ser Phe Ala Pro Gly Asn
50                  55                  60

Val Ser Ile Lys Trp Tyr Glu Asp Gly Thr Leu Asn Leu Ala Ala Asn
65                  70                  75                  80

Cys Leu Asp Arg His Leu Gln Glu Asn Gly Asp Arg Thr Ala Ile Ile
            85                  90                  95

Trp Glu Gly Asp Asp Ala Ser Gln Ser Lys His Ile Ser Tyr Lys Glu
            100                 105                 110

Leu His Arg Asp Val Cys Arg Phe Ala Asn Thr Leu Leu Glu Leu Gly
        115                 120                 125

Ile Lys Lys Gly Asp Val Val Ala Ile Tyr Met Pro Met Val Pro Glu
130                 135                 140

Ala Ala Val Ala Met Leu Ala Cys Ala Arg Ile Gly Ala Val His Ser
145                 150                 155                 160

Val Ile Phe Gly Gly Phe Ser Pro Glu Ala Val Ala Gly Arg Ile Ile
            165                 170                 175

Asp Ser Asn Ser Arg Leu Val Ile Thr Ser Asp Glu Gly Val Arg Ala
        180                 185                 190

Gly Arg Ser Ile Pro Leu Lys Lys Asn Val Asp Ala Leu Lys Asn
            195                 200                 205

Pro Asn Val Thr Ser Val Glu His Val Val Val Leu Lys Arg Thr Gly
210                 215                 220

Gly Lys Ile Asp Trp Gln Glu Gly Arg Asp Leu Trp Trp His Asp Leu
225                 230                 235                 240

Val Glu Gln Ala Ser Asp Gln His Gln Ala Glu Met Asn Ala Glu
            245                 250                 255

Asp Pro Leu Phe Ile Leu Tyr Thr Ser Gly Ser Thr Gly Lys Pro Lys
            260                 265                 270

Gly Val Leu His Thr Thr Gly Gly Tyr Leu Val Tyr Ala Ala Leu Thr
        275                 280                 285

Phe Lys Tyr Val Phe Asp Tyr His Pro Gly Asp Ile Tyr Trp Cys Thr
290                 295                 300

Ala Asp Val Gly Trp Val Thr Gly His Ser Tyr Leu Leu Tyr Gly Pro
305                 310                 315                 320

Leu Ala Cys Gly Ala Thr Thr Leu Met Phe Glu Gly Val Pro Asn Trp
            325                 330                 335

Pro Thr Pro Ala Arg Met Ala Gln Val Val Asp Lys His Gln Val Asn
        340                 345                 350
```

```
Ile Leu Tyr Thr Ala Pro Thr Ala Ile Arg Ala Leu Met Ala Glu Gly
            355                 360                 365
Asp Lys Ala Ile Glu Gly Thr Asp Arg Ser Ser Leu Arg Ile Leu Gly
        370                 375                 380
Ser Val Gly Glu Pro Ile Asn Pro Glu Ala Trp Glu Trp Tyr Trp Lys
385                 390                 395                 400
Lys Ile Gly Asn Glu Lys Cys Pro Val Val Asp Thr Trp Trp Gln Thr
                405                 410                 415
Glu Thr Gly Gly Phe Met Ile Thr Pro Leu Pro Gly Ala Thr Glu Leu
            420                 425                 430
Lys Ala Gly Ser Ala Thr Arg Pro Phe Phe Gly Val Gln Pro Ala Leu
        435                 440                 445
Val Asp Asn Glu Gly Asn Pro Leu Glu Gly Ala Thr Glu Gly Ser Leu
    450                 455                 460
Val Ile Thr Asp Ser Trp Pro Gly Gln Ala Arg Thr Leu Phe Gly Asp
465                 470                 475                 480
His Glu Arg Phe Glu Gln Thr Tyr Phe Ser Thr Phe Lys Asn Met Tyr
                485                 490                 495
Phe Ser Gly Asp Gly Ala Arg Arg Asp Glu Asp Gly Tyr Tyr Trp Ile
            500                 505                 510
Thr Gly Arg Val Asp Asp Val Leu Asn Val Ser Gly His Arg Leu Gly
        515                 520                 525
Thr Ala Glu Ile Glu Ser Ala Leu Val Ala His Pro Lys Ile Ala Glu
    530                 535                 540
Ala Ala Val Val Gly Ile Pro His Asn Ile Lys Gly Gln Ala Ile Tyr
545                 550                 555                 560
Ala Tyr Val Thr Leu Asn His Gly Glu Glu Pro Ser Pro Glu Leu Tyr
                565                 570                 575
Ala Glu Val Arg Asn Trp Val Arg Lys Glu Ile Gly Pro Leu Ala Thr
            580                 585                 590
Pro Asp Val Leu His Trp Thr Asp Ser Leu Pro Lys Thr Arg Ser Gly
        595                 600                 605
Lys Ile Met Arg Arg Ile Leu Arg Lys Ile Ala Ala Gly Asp Thr Ser
    610                 615                 620
Asn Leu Gly Asp Thr Ser Thr Leu Ala Asp Pro Gly Val Val Glu Lys
625                 630                 635                 640
Leu Leu Glu Glu Lys Gln Ala Ile Ala Met Pro Ser
                645                 650

<210> SEQ ID NO 46
<211> LENGTH: 1689
<212> TYPE: DNA
<213> ORGANISM: Escherichia coli
<220> FEATURE:
<221> NAME/KEY: misc_feature
<223> OTHER INFORMATION: acyl-CoA synthetase

<400> SEQUENCE: 46
atgcgctatg ccgatttttcc aacgctggtt gatgctttgg actacgccgc tctgagtagc      60
gccggaatga ttttttatga cagacgttgc caacttgaag atcaactgga atatcagaca     120
ttaaaaacgc gtgccgaagc tggtgcgaag cggttgttat cgctgaacct gaaaaaaggc     180
gatcgcgtgg cactgattgc cgaaacaagt agcgggttcg tagaggcttt ttttgcctgc     240
cagtatgccg gctagtcgc cgtcccgttg gcgattccaa tgggcgttgg tcagcgggat     300
tcctggagcg ccaaattgca gggtttactg gcaagttgcc agcccgcagc cattatcact     360
```

```
ggtgatgagt ggttgccact ggtcaatgcc gcgacgcatg acaaccccga attacatgtt    420
ttaagccacg cctggtttaa ggcattaccg gaagccgatg ttgcgctcca gcgtccagtt    480
ccgaacgata tcgcctacct ccagtacacc tccggcagca cccgttttcc ccgtggcgtc    540
attatcaccc atcgcgaagt gatggctaat ctacgtgcta taagccacga cggcattaaa    600
ttacgccctg cgaccgctg cgtctcctgg ctgcctttct accatgatat gggactggtc    660
ggctttctcc tgacccccgt cgccacgcag ctttcagtag attatttgcg cactcaggat    720
tttgccatgc gtcctctgca atggcttaaa ttgatcagta aaatcgcgg caccgtttcc    780 gttgcgccgc cgtttggcta tgaattgtgc cagcgccgcg tgaatgaaaa agatctcgct    840
gaactggatc tttcctgctg gcgcgtcgct ggtattggtg cagaacccat ctccgcagaa    900
caactccatc aattcgctga atgtttccgt caggttaact ttgacaataa aactttcatg    960
ccgtgctacg gactggcaga aaatgcgctg gctgtcagct tctctgatga gcctccggg    1020 gttgtggtta acgaagtgga tcgcgacatc ctcgaatatc agggtaaagc cgtcgcgccg    1080
ggtgcagaga cacgcgccgt atcgactttc gtcaactgcg gcaaagcgtt gccggaacat    1140
ggtattgaaa tccgcaatga agcaggtatg ccggtcgcgg aacgtgtggt aggccatatt    1200
tgcatctccg gtcccagtct gatgagcggt tactttggcg accaggcttc gcaagacgag    1260
attgccgcga cgggctggtt agacaccggc gacctcggtt atctgctgga cggttatctg    1320
tatgtcaccg gacgcattaa agatctgatt attattcgtg gccgtaatat ctggccgcag    1380
gatattgaat atattgcgga caagaaccg gaaattcatt ctggcgatgc gattgctttt    1440
gttaccgccc aggaaaaaat cattttgcag atccagtgtc ggatcagcga cgaagaacgt    1500
cgcgggcagc ttatccacgc gctggcggca cggatccaaa gcgaatttgg cgtgaccgcg    1560
gctatcgagc tgttgccgcc ccacagtatt ccccgaacgt cctccggcaa gcctgcccgt    1620
gcggaagcga aaaacgttta tcagaaggct tatgctgcca gtcttcatgt gcaggaatcc    1680
ctggcatga                                                            1689
```

<210> SEQ ID NO 47
<211> LENGTH: 562
<212> TYPE: PRT
<213> ORGANISM: Escherichia coli
<220> FEATURE:
<221> NAME/KEY: MISC_FEATURE
<223> OTHER INFORMATION: acyl-CoA synthetase

<400> SEQUENCE: 47

```
Met Arg Tyr Ala Asp Phe Pro Thr Leu Val Asp Ala Leu Asp Tyr Ala
1               5                   10                  15

Ala Leu Ser Ser Ala Gly Met Asn Phe Tyr Asp Arg Arg Cys Gln Leu
            20                  25                  30

Glu Asp Gln Leu Glu Tyr Gln Thr Leu Lys Thr Arg Ala Glu Ala Gly
        35                  40                  45

Ala Lys Arg Leu Leu Ser Leu Asn Leu Lys Lys Gly Asp Arg Val Ala
    50                  55                  60

Leu Ile Ala Glu Thr Ser Ser Gly Phe Val Glu Ala Phe Phe Ala Cys
65                  70                  75                  80

Gln Tyr Ala Gly Leu Val Ala Val Pro Leu Ala Ile Pro Met Gly Val
                85                  90                  95

Gly Gln Arg Asp Ser Trp Ser Ala Lys Leu Gln Gly Leu Leu Ala Ser
            100                 105                 110
```

-continued

Cys Gln Pro Ala Ala Ile Ile Thr Gly Asp Glu Trp Leu Pro Leu Val
            115                 120                 125

Asn Ala Ala Thr His Asp Asn Pro Glu Leu His Val Leu Ser His Ala
        130                 135                 140

Trp Phe Lys Ala Leu Pro Glu Ala Asp Val Ala Leu Gln Arg Pro Val
145                 150                 155                 160

Pro Asn Asp Ile Ala Tyr Leu Gln Tyr Thr Ser Gly Ser Thr Arg Phe
                165                 170                 175

Pro Arg Gly Val Ile Ile Thr His Arg Glu Val Met Ala Asn Leu Arg
            180                 185                 190

Ala Ile Ser His Asp Gly Ile Lys Leu Arg Pro Gly Asp Arg Cys Val
        195                 200                 205

Ser Trp Leu Pro Phe Tyr His Asp Met Gly Leu Val Gly Phe Leu Leu
    210                 215                 220

Thr Pro Val Ala Thr Gln Leu Ser Val Asp Tyr Leu Arg Thr Gln Asp
225                 230                 235                 240

Phe Ala Met Arg Pro Leu Gln Trp Leu Lys Leu Ile Ser Lys Asn Arg
                245                 250                 255

Gly Thr Val Ser Val Ala Pro Pro Phe Gly Tyr Glu Leu Cys Gln Arg
            260                 265                 270

Arg Val Asn Glu Lys Asp Leu Ala Glu Leu Asp Leu Ser Cys Trp Arg
        275                 280                 285

Val Ala Gly Ile Gly Ala Glu Pro Ile Ser Ala Glu Gln Leu His Gln
    290                 295                 300

Phe Ala Glu Cys Phe Arg Gln Val Asn Phe Asp Asn Lys Thr Phe Met
305                 310                 315                 320

Pro Cys Tyr Gly Leu Ala Glu Asn Ala Leu Ala Val Ser Phe Ser Asp
                325                 330                 335

Glu Ala Ser Gly Val Val Asn Glu Val Asp Arg Asp Ile Leu Glu
            340                 345                 350

Tyr Gln Gly Lys Ala Val Ala Pro Gly Ala Glu Thr Arg Ala Val Ser
        355                 360                 365

Thr Phe Val Asn Cys Gly Lys Ala Leu Pro Glu His Gly Ile Glu Ile
    370                 375                 380

Arg Asn Glu Ala Gly Met Pro Val Ala Glu Arg Val Val Gly His Ile
385                 390                 395                 400

Cys Ile Ser Gly Pro Ser Leu Met Ser Gly Tyr Phe Gly Asp Gln Ala
                405                 410                 415

Ser Gln Asp Glu Ile Ala Ala Thr Gly Trp Leu Asp Thr Gly Asp Leu
            420                 425                 430

Gly Tyr Leu Leu Asp Gly Tyr Leu Tyr Val Thr Gly Arg Ile Lys Asp
        435                 440                 445

Leu Ile Ile Ile Arg Gly Arg Asn Ile Trp Pro Gln Asp Ile Glu Tyr
    450                 455                 460

Ile Ala Glu Gln Glu Pro Glu Ile His Ser Gly Asp Ala Ile Ala Phe
465                 470                 475                 480

Val Thr Ala Gln Glu Lys Ile Ile Leu Gln Ile Gln Cys Arg Ile Ser
                485                 490                 495

Asp Glu Glu Arg Arg Gly Gln Leu Ile His Ala Leu Ala Ala Arg Ile
            500                 505                 510

Gln Ser Glu Phe Gly Val Thr Ala Ala Ile Glu Leu Leu Pro Pro His
        515                 520                 525

Ser Ile Pro Arg Thr Ser Ser Gly Lys Pro Ala Arg Ala Glu Ala Lys

```
                    530                535                540
Lys Arg Tyr Gln Lys Ala Tyr Ala Ala Ser Leu His Val Gln Glu Ser
545                550                555                560

Leu Ala

<210> SEQ ID NO 48
<211> LENGTH: 1284
<212> TYPE: DNA
<213> ORGANISM: Escherichia coli
<220> FEATURE:
<221> NAME/KEY: misc_feature
<223> OTHER INFORMATION: citric synthetase

<400> SEQUENCE: 48
atggctgata caaaagcaaa actcaccctc aacggggata cagctgttga actggatgtg      60
ctgaaaggca cgctgggtca agatgttatt gatatccgta ctctcggttc aaaaggtgtg     120
ttcacctttg acccaggctt cacttcaacc gcatcctgcg aatctaaaat tacttttatt     180
gatggtgatg aaggtatttt gctgcaccgc ggtttcccga tcgatcagct ggcgaccgat     240
tctaactacc tggaagtttg ttacatcctg ctgaatggtg aaaaaccgac tcaggaacag     300
tatgacgaat taaaactac ggtgacccgt cataccatga tccacgagca gattacccgt     360
ctgttccatg ctttccgtcg cgactcgcat ccaatggcag tcatgtgtgg tattaccggc     420
gcgctggcgg cgttctatca cgactcgctg atgttaaca atcctcgtca ccgtgaaatt     480
gccgcgttcc gcctgctgtc gaaaatgccg accatggccg cgatgtgtta caagtattcc     540
attggtcagc catttgttta cccgcgcaac gatctctcct acgccggtaa cttcctgaat     600
atgatgttct ccacgccgtg cgaaccgtat gaagttaatc cgattctgga acgtgctatg     660
gaccgtattc tgatcctgca cgctgaccat gaacagaacg cctctacctc caccgtgcgt     720
accgctggct cttcgggtgc gaacccgttt gcctgtatcg cagcaggtat tgcttcactg     780
tggggacctg cgcacggcgg tgctaacgaa gcggcgctga aatgctgga agaaatcagc     840 tccgttaaac acattccgga atttgttcgt cgtgcgaaag acaaaaatga ttctttccgc     900
ctgatgggct tcggtcaccg cgtgtacaaa aattacgacc cgcgcgccac cgtaatgcgt     960
gaaacctgcc atgaagtgct gaaagagctg ggcacgaagg atgacctgct ggaagtggct    1020
atggagctgg aaaacatcgc gctgaacgac ccgtacttta tcgagaagaa actgtacccg    1080
aacgtcgatt tctactctgg tatcatcctg aaagcgatgg gtattccgtc ttccatgttc    1140
accgtcattt tcgcaatggc acgtaccgtt ggctggatcg cccactggag cgaaatgcac    1200
agtgacggta tgaagattgc ccgtccgcgt cagctgtata caggatatga aaaacgcgac    1260
tttaaaagcg atatcaagcg ttaa                                           1284

<210> SEQ ID NO 49
<211> LENGTH: 427
<212> TYPE: PRT
<213> ORGANISM: Escherichia coli
<220> FEATURE:
<221> NAME/KEY: MISC_FEATURE
<223> OTHER INFORMATION: citric synthetase

<400> SEQUENCE: 49

Met Ala Asp Thr Lys Ala Lys Leu Thr Leu Asn Gly Asp Thr Ala Val
1               5                   10                  15

Glu Leu Asp Val Leu Lys Gly Thr Leu Gly Gln Asp Val Ile Asp Ile
                20                  25                  30
```

Arg Thr Leu Gly Ser Lys Gly Val Phe Thr Phe Asp Pro Gly Phe Thr
                35                  40                  45

Ser Thr Ala Ser Cys Glu Ser Lys Ile Thr Phe Ile Asp Gly Asp Glu
 50                  55                  60

Gly Ile Leu Leu His Arg Gly Phe Pro Ile Asp Gln Leu Ala Thr Asp
 65                  70                  75                  80

Ser Asn Tyr Leu Glu Val Cys Tyr Ile Leu Leu Asn Gly Glu Lys Pro
                 85                  90                  95

Thr Gln Glu Gln Tyr Asp Glu Phe Lys Thr Thr Val Thr Arg His Thr
            100                 105                 110

Met Ile His Glu Gln Ile Thr Arg Leu Phe His Ala Phe Arg Arg Asp
            115                 120                 125

Ser His Pro Met Ala Val Met Cys Gly Ile Thr Gly Ala Leu Ala Ala
130                 135                 140

Phe Tyr His Asp Ser Leu Asp Val Asn Asn Pro Arg His Arg Glu Ile
145                 150                 155                 160

Ala Ala Phe Arg Leu Leu Ser Lys Met Pro Thr Met Ala Met Cys
                165                 170                 175

Tyr Lys Tyr Ser Ile Gly Gln Pro Phe Val Tyr Pro Arg Asn Asp Leu
                180                 185                 190

Ser Tyr Ala Gly Asn Phe Leu Asn Met Met Phe Ser Thr Pro Cys Glu
            195                 200                 205

Pro Tyr Glu Val Asn Pro Ile Leu Glu Arg Ala Met Asp Arg Ile Leu
            210                 215                 220

Ile Leu His Ala Asp His Glu Gln Asn Ala Ser Thr Ser Thr Val Arg
225                 230                 235                 240

Thr Ala Gly Ser Ser Gly Ala Asn Pro Phe Ala Cys Ile Ala Ala Gly
                245                 250                 255

Ile Ala Ser Leu Trp Gly Pro Ala His Gly Gly Ala Asn Glu Ala Ala
                260                 265                 270

Leu Lys Met Leu Glu Glu Ile Ser Ser Val Lys His Ile Pro Glu Phe
            275                 280                 285

Val Arg Arg Ala Lys Asp Lys Asn Asp Ser Phe Arg Leu Met Gly Phe
            290                 295                 300

Gly His Arg Val Tyr Lys Asn Tyr Asp Pro Arg Ala Thr Val Met Arg
305                 310                 315                 320

Glu Thr Cys His Glu Val Leu Lys Glu Leu Gly Thr Lys Asp Asp Leu
                325                 330                 335

Leu Glu Val Ala Met Glu Leu Glu Asn Ile Ala Leu Asn Asp Pro Tyr
            340                 345                 350

Phe Ile Glu Lys Lys Leu Tyr Pro Asn Val Asp Phe Tyr Ser Gly Ile
            355                 360                 365

Ile Leu Lys Ala Met Gly Ile Pro Ser Ser Met Phe Thr Val Ile Phe
370                 375                 380

Ala Met Ala Arg Thr Val Gly Trp Ile Ala His Trp Ser Glu Met His
385                 390                 395                 400

Ser Asp Gly Met Lys Ile Ala Arg Pro Arg Gln Leu Tyr Thr Gly Tyr
                405                 410                 415

Glu Lys Arg Asp Phe Lys Ser Asp Ile Lys Arg
            420                 425

<210> SEQ ID NO 50
<211> LENGTH: 72
<212> TYPE: DNA

```
<213> ORGANISM: Artificial sequence
<220> FEATURE:
<223> OTHER INFORMATION: Synthetic oligonucleotide

<400> SEQUENCE: 50
atgcgctatg ccgattttcc aacgctggtt gatgctttgg actacgccgc aattaaccct    60
cactaaaggg cg                                                        72

<210> SEQ ID NO 51
<211> LENGTH: 73
<212> TYPE: DNA
<213> ORGANISM: Artificial sequence
<220> FEATURE:
<223> OTHER INFORMATION: Synthetic oligonucleotide

<400> SEQUENCE: 51
tcatgccagg gattcctgca catgaagact ggcagcataa gccttctgat taatacgact    60
cactataggg ctc                                                       73

<210> SEQ ID NO 52
<211> LENGTH: 72
<212> TYPE: DNA
<213> ORGANISM: Artificial sequence
<220> FEATURE:
<223> OTHER INFORMATION: Synthetic oligonucleotide

<400> SEQUENCE: 52
atggctgata caaaagcaaa actcaccctc aacggggata cagctgttga aattaaccct    60
cactaaaggg cg                                                        72

<210> SEQ ID NO 53
<211> LENGTH: 72
<212> TYPE: DNA
<213> ORGANISM: Artificial sequence
<220> FEATURE:
<223> OTHER INFORMATION: Synthetic oligonucleotide

<400> SEQUENCE: 53
taacgcttga tatcgctttt aaagtcgcgt ttttcatatc ctgtatacat aatacgactc    60
actatagggc tc                                                        72
```